US010927098B2

(12) United States Patent
Fuerstner et al.

(10) Patent No.: US 10,927,098 B2
(45) Date of Patent: Feb. 23, 2021

(54) HYDROXYALKYL-SUBSTITUTED TRIAZOLE DERIVATIVES AND USES THEREOF

(71) Applicant: Bayer Pharma Aktiengesellschaft, Berlin (DE)

(72) Inventors: Chantal Fuerstner, Muelheim an der Ruhr (DE); Marie-Pierre Collin-Kroepelin, Wuppertal (DE); Peter Kolkhof, Wuppertal (DE); Thomas Neubauer, Wuppertal (DE); Elisabeth Pook, Wuppertal (DE); Heiko Schirmer, Solingen (DE); Carsten Schmeck, Muelheim (DE); Pierre Wasnaire, Duesseldorf (DE); Matthias Beat Wittwer, Riehen (CH)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 16/343,150

(22) PCT Filed: Oct. 16, 2017

(86) PCT No.: PCT/EP2017/076280
§ 371 (c)(1),
(2) Date: Apr. 18, 2019

(87) PCT Pub. No.: WO2018/073144
PCT Pub. Date: Apr. 26, 2018

(65) Prior Publication Data
US 2019/0315720 A1 Oct. 17, 2019

(30) Foreign Application Priority Data
Oct. 20, 2016 (EP) ..................... 16194869

(51) Int. Cl.
*C07D 403/06* (2006.01)
*A61P 13/12* (2006.01)
*C07D 403/14* (2006.01)

(52) U.S. Cl.
CPC ............ *C07D 403/06* (2013.01); *A61P 13/12* (2018.01); *C07D 403/14* (2013.01)

(58) Field of Classification Search
CPC ...... C07D 403/14; C07D 403/06; A61P 13/12
See application file for complete search history.

(56) References Cited

U.S. PATENT DOCUMENTS

| | | | |
|---|---|---|---|
| 6,693,102 B2 | 2/2004 | Stasch et al. | |
| 6,743,798 B1 | 6/2004 | Straub et al. | |
| 6,833,364 B1 | 12/2004 | Straub et al. | |
| 6,864,287 B1 | 3/2005 | Alonso-Alija et al. | |
| 7,087,644 B1 | 8/2006 | Alonso-Alija et al. | |
| 7,173,037 B2 | 2/2007 | Alonso-Alija et al. | |
| 7,517,896 B2 | 4/2009 | Alonso-Alija et al. | |
| 7,674,825 B2 | 3/2010 | Alonso-Alija et al. | |
| 7,705,043 B2 | 4/2010 | Alonso-Alija et al. | |
| 7,781,470 B2 | 8/2010 | Alonso-Alija et al. | |
| 8,202,895 B2 | 6/2012 | Bruggemeier et al. | |
| 8,420,656 B2 | 4/2013 | Follmann et al. | |
| 8,796,324 B2 | 8/2014 | Brueggemeier | |
| 8,921,377 B2 | 12/2014 | Follmann et al. | |
| 9,096,592 B2 | 8/2015 | Follmann et al. | |
| 9,187,466 B2 | 11/2015 | Furstner et al. | |
| 9,216,978 B2 | 12/2015 | Follmann et al. | |
| 9,266,885 B2 | 2/2016 | Follmann et al. | |
| 9,687,476 B2 | 6/2017 | Furstner et al. | |
| 9,771,352 B2 | 9/2017 | Schmeck et al. | |
| 9,993,476 B2 | 6/2018 | Follmann et al. | |
| 2002/0173514 A1 | 11/2002 | Stasch et al. | |
| 2004/0082798 A1 | 4/2004 | Alonso-Alija et al. | |
| 2004/0176446 A1 | 9/2004 | Alonso-Alija et al. | |
| 2004/0224945 A1 | 11/2004 | Straub et al. | |
| 2006/0052397 A1 | 3/2006 | Alonso-Alija et al. | |
| 2007/0179139 A1 | 8/2007 | Alonso-Alija et al. | |
| 2008/0058314 A1 | 3/2008 | Alonso-Alija et al. | |
| 2010/0261771 A1 | 10/2010 | Bruggemeier et al. | |
| 2010/0317854 A1 | 12/2010 | Alonso-Alija et al. | |
| 2012/0022084 A1 | 1/2012 | Follmann et al. | |
| 2012/0238607 A1 | 9/2012 | Bruggemeier et al. | |
| 2013/0237551 A1 | 9/2013 | Follmann et al. | |
| 2014/0148433 A1 | 5/2014 | Follmann et al. | |
| 2014/0350020 A1 | 11/2014 | Follmann et al. | |
| 2015/0080414 A1 | 3/2015 | Follmann et al. | |

(Continued)

FOREIGN PATENT DOCUMENTS

WO 0006568 A1 2/2000
WO 0006569 A1 2/2000
(Continued)

OTHER PUBLICATIONS

International Search Report for PCT/EP2017/076280, dated Mar. 13, 2018.
R.Schrier et al. "Hormones And Hemodynamics In Heart Failure" The New England Journal of Medicine vol. 341 No. 8, Aug. 19, 1999, pp. 577-585.
De Luca et al. "Hyponatremia In Patients With Heart Failure" The American Journal of Cardiology, vol. 96, Dec. 19, 2005, pp. 19L-23L.
Francis et al. "Comparison Of Neuroendocrine Activation In Patients With Left Ventricular Dysfunction With And Without Congestive Heart Failure" American Heart Association Circulation vol. 82 No. 5, Nov. 5, 1990, pp. 1724-1729.

(Continued)

*Primary Examiner* — Alicia L Otton
(74) *Attorney, Agent, or Firm* — McBee Moore & Vanik IP, LLC

(57) ABSTRACT

The present invention relates to novel 3-(hydroxyalkyl)-1,2,4-triazole derivatives, to processes for the preparation of such compounds, to pharmaceutical compositions containing such compounds, and to the use of such compounds or compositions for the treatment and/or prevention of diseases, in particular for the treatment and/or prevention of renal and/or cardiovascular diseases.

11 Claims, No Drawings

(56) References Cited

U.S. PATENT DOCUMENTS

| | | | |
|---|---|---|---|
| 2016/0051518 | A1 | 2/2016 | Fuerstner et al. |
| 2016/0122325 | A1 | 5/2016 | Schmeck et al. |
| 2016/0129004 | A1 | 5/2016 | Follmann et al. |
| 2017/0273977 | A1 | 9/2017 | Follmann et al. |
| 2017/0313665 | A1 | 11/2017 | Schmeck et al. |
| 2018/0263981 | A1 | 9/2018 | Follmann et al. |

FOREIGN PATENT DOCUMENTS

| | | | |
|---|---|---|---|
| WO | 0119355 | A2 | 3/2001 |
| WO | 0119776 | A2 | 3/2001 |
| WO | 0119778 | A1 | 3/2001 |
| WO | 0119780 | A2 | 3/2001 |
| WO | 0242301 | A1 | 5/2002 |
| WO | 02070462 | A1 | 9/2002 |
| WO | 02070510 | A2 | 9/2002 |
| WO | 03095451 | A1 | 11/2003 |
| WO | 2005063754 | A1 | 7/2005 |
| WO | 2005105779 | A1 | 11/2005 |
| WO | 2010105770 | A1 | 9/2010 |
| WO | 2011104322 | A1 | 9/2011 |
| WO | 2011147809 | A1 | 12/2011 |
| WO | 2012004258 | A1 | 1/2012 |
| WO | 2012028647 | A1 | 3/2012 |
| WO | 2016071212 | A1 | 5/2016 |

OTHER PUBLICATIONS

Sanghi p et al. "Vasopressin Antagonism: A Future Treatment Option In Heart Failure", European Heart Journal vol. 26, Dec. 16, 2004, pp. 538-543.
Wasilewski et al "Arginine Vasopressin Receptor Signaling And Functional Outcomes In Heart Failure" Cellular Signalling Elsevier Journal vol. 28, 2016, pp. 224-233.
Li Xue et al. "Controlled And Cardiac-Restricted Overexpression Of The Arginine Vasopressin V1A Receptor Causes Reversible Left Ventricular Dysfunction Through Gxq-Mediated Cell Signaling" American Heart Association Journal Circulation, Aug. 2, 2011, pp. 574-581.
Thibonnier et al. "Characterization Of Human Platelet Vasopressin Receptors" The American Society for Journal of Clincal Investigations vol. 76, Nov. 1985, pp. 1857-1864.
Taveau et al. "Vasopressin And Hydration Play A Major Role In The Development Of Glucose Intolerance And Hepatic Steatosis In Obese Rats" Hypertension Diabetologia vol. 58, 2015, pp. 1081-1090.
Santillan et al. "Vasopress In Preeclampsia: A Novel Very Early Human Pregnancy Biomarker And Clinically Relevant Mouse Model" American Heart Association Journal vol. 64 No. 4, Oct. 2014, pp. 852-859.
Berge et al. "Pharmaceutical Salts" Journal of Pharmaceutical Sciences vol. 66 No. 1, Jan. 1977, pp. 1-19.
"Readily Accessible 12-I-5 Oxidant For The Conversion Of Primary And Secondary Alcohols To Aldehydes And Ketones" Journal of Organic Chemistry vol. 48, 1983, pp. 4155-4156.
Ward et al. "Synthesis Of (-) Bactobolin From D-Glucose And From (+)- Actinobolin" Tetrahedron Letters vol. 35 No. 21, 1994, pp. 3485-3488.
Lee et al. "The Aqueous Dichromate Oxidation Of Primary Alcohols" Journal of Organic Chemistry vol. 35 No. 10, Apr. 27, 1970, pp. 3589-3590.
Corey et al. "Useful Procedures For The Oxidation Of Alcohols Involving Pyridinium Dichromate In Aprotic Media" Tetrahedron Letters No. 5, 1979, pp. 399-402.
Omura et al. "Oxidation Of Alcohols By "Activated" Dimethyl Sulfoxide A Preparative Steric And Mechanistic Study" Tetrahedron Letters vol. 34, 1978, pp. 1651-1660.
Bianchi et al. "5-Oxo-1H-4,5 dihydro-1,2,4-Benzotriazepines Chemical Behavior Towards Alkylating Acidic And Alkaline Agents" Journal of Heterocyclic Chemistry vol. 16, pp. 1411-1416.
Chan et al. "Copper Promoted C-N and C-O Bond Cross-Coupling With Phenyl And Pyridylboronates" Tetrahedron Letters vol. 44, Feb. 2003, pp. 3863-3865.
Qiao et al. "Copper-Promoted Carbon-Heteroatom Bond Cross-Coupling With Boronic Acids And Derivatives" Synthesis No. 6, 2011, pp. 829-856.
Rao et al. "Chan-Lam Coupling Reactions: Synthesis Of Heterocycles" Tetrahedron vol. 68, 2012, pp. 7735-7754.
Kahn et al. "Management Of Cardiovascular Disease In Patients With Kidney Disease" Nature Reveiws| Cardiolgy vol. 10, May 2003, pp. 261-273.
Rizzuto et al. "Rapid Changes Of Mitochondrial Ca2+ Revealed By Specifically Targeted Recombinant Aequorin" Letters to Nature vol. 358, Jul. 23, 1992, pp. 325-327.
Illarionov et al. "Sequence Of The cDNA Encodding The Ca2+ Acitvated Photoprotein Obelin From The Hydroid Polyp Obelia Longissima" Gene vol. 153, 1995, pp. 273-274.
Milligan et al. "G16 As A Universal G Protein Adapter: Implications For Agonist Screening Strategies" Trends in Pharmacological Sciences vol. 17, 1996, pp. 235-237.
Cheng et al. "Relationship Between The Inhibition Constant (K1) And The Concentration Of Inhibitor Which Causes 50 Percent Inhibition (I50) Of An Enzymatic Reaction" Biochemical Pharmacology vol. 22, 1973, pp. 3099-3108.
Undeutsch et al. "Citation Of NMR Peaklist Data Within Patent Applications" Research Disclosure No. 564025, Aug. 1, 2014, pp. 1-5.

US 10,927,098 B2

HYDROXYALKYL-SUBSTITUTED TRIAZOLE DERIVATIVES AND USES THEREOF

CROSS-REFERENCE TO RELATED APPLICATIONS

This application is the National Stage entry of International Application No. PCT/EP2017/076280, filed 16 Oct. 2017, which claims priority to European Patent Application No. 16194869.0, filed 20 Oct. 2016.

BACKGROUND

Field

The present invention relates to novel 3-(hydroxyalkyl)-1,2,4-triazole derivatives, to processes for the preparation of such compounds, to pharmaceutical compositions containing such compounds, and to the use of such compounds or compositions for the treatment and/or prevention of diseases, in particular for the treatment and/or prevention of renal and/or cardiovascular diseases.

Description of Related Art

The liquid content of the human body is subject to various physiological control mechanisms, the purpose of which is to keep it constant (volume homeostasis). In the process, both the volume filling of the vascular system and also the osmolarity of the plasma are continuously recorded by appropriate sensors (baroreceptors and osmoreceptors). The information which these sensors supply to the relevant centers in the brain regulates drinking behaviour and controls fluid excretion via the kidneys by means of humoral and neural signals. The peptide hormone vasopressin is of central importance in this [Schrier R. W., Abraham W. T., New Engl. J. Med. 341, 577-585 (1999)].

Vasopressin is produced in specialized endocrine neurons in the Nucleus supraopticus and N. paraventricularis in the wall of the third ventricle (hypothalamus) and is transported from there along the neural processes into the posterior lobes of the hypophysis (neurohypophysis). There the hormone is released into the bloodstream in response to stimulus. A loss of volume, e.g. as a result of acute bleeding, heavy sweating, prolonged thirst or diarrhoea, is a stimulus for intensified release of the hormone. Conversely, the secretion of vasopressin is inhibited by an increase in the intravascular volume, e.g. as a result of increased fluid intake.

Vasopressin exerts its action mainly via binding to three receptors, which are classified as V1a, V1b and V2 receptors and which belong to the family of G protein-coupled receptors. V1a receptors are mainly located on the cells of the vascular smooth musculature. Their activation gives rise to vasoconstriction, as a result of which the peripheral resistance and blood pressure rise. Apart from this, V1a receptors are also detectable in the liver. V1b receptors (also named V3 receptors) are detectable in the central nervous system. Together with corticotropin-releasing hormone (CRH), vasopressin regulates the basal and stress-induced secretion of adrenocorticotropic hormone (ACTH) via the V1b receptor. V2 receptors are located in the distal tubular epithelium and the epithelium of the collecting tubules in the kidney. Their activation renders these epithelia permeable to water. This phenomenon is due to the incorporation of aquaporins (special water channels) in the luminal membrane of the epithelial cells.

The importance of vasopressin for the reabsorption of water from the urine in the kidney becomes clear from the clinical picture of diabetes insipidus, which is caused by a deficiency of the hormone, e.g. owing to hypophysis damage. Patients who suffer from this disease excrete up to 20 liters of urine per 24 hours if they are not given replacement hormone. This volume corresponds to about 10% of the primary urine. Because of its great importance for the reabsorption of water from the urine, vasopressin is also synonymously referred to as antidiuretic hormone (ADH). Consequently, pharmacological inhibition of the action of vasopressin/ADH on the V2 receptor results in increased urine excretion. In contrast to the action of other diuretics (thiazides and loop diuretics), however, V2 receptor antagonists cause increased water excretion, without substantially increasing the excretion of electrolytes. This means that with V2 antagonist drugs, volume homeostasis can be restored without affecting electrolyte homeostasis. Hence, drugs with V2 antagonistic activity appear particularly suitable for the treatment of all disease conditions which are associated with an overloading of the body with water, without the electrolytes being adequately increased in parallel.

A significant electrolyte abnormality is measurable in clinical chemistry as hyponatremia (sodium concentration <135 mmol/L); it is the most important electrolyte abnormality in hospital patients, with an incidence of about 5% or 250 000 cases per year in the US alone. If the plasma sodium concentration falls below 115 mmol/L, comatose states and death are imminent. Depending on the underlying cause, a distinction is made between hypovolemic, euvolemic and hypervolemic hyponatremia. The forms of hypervolemia with edema formation are clinically significant. Typical examples of these are the syndrome of inappropriate ADH/vasopressin secretion (SIADH) (e.g. after craniocerebral trauma or as paraneoplasia in carcinomas) and hypervolemic hyponatremia in liver cirrhosis, various renal diseases and heart failure [De Luca L. et al., Am. J. Cardiol. 96 (suppl.), 19 L-23 L (2005)]. In particular, patients with heart failure, in spite of their relative hyponatremia and hypervolemia, often display elevated vasopressin levels, which are seen as the consequence of a generally disturbed neurohumoral regulation in heart failure [Francis G. S. et al., Circulation 82, 1724-1729 (1990)].

The disturbed neurohormonal regulation essentially manifests itself in an elevation of the sympathetic tone and inappropriate activation of the renin-angiotensin-aldosterone system. While the inhibition of these components by beta-receptor blockers on the one hand and by ACE inhibitors or angiotensin-receptor blockers on the other is now an inherent part of the pharmacological treatment of heart failure, the inappropriate elevation of vasopressin secretion in advanced heart failure is at present still not adequately treatable. Apart from the retention of water mediated by V2 receptors and the unfavourable hemodynamic consequences associated therewith in terms of increased backload, the emptying of the left ventricle, the pressure in the pulmonary blood vessels and cardiac output are also adversely affected by Via-mediated vasoconstriction. Furthermore, on the basis of experimental data in animals, a direct hypertrophy-promoting action on the heart muscle is also attributed to vasopressin. In contrast to the renal effect of volume expansion, which is mediated by activation of V2 receptors, the direct action on the heart muscle is triggered by activation of V1a receptors.

For these reasons, agents which inhibit the action of vasopressin on the V2 and/or the V1a receptor appear suitable for the treatment of heart failure. In particular, compounds with combined activity on both vasopressin receptors (V1a and V2) should have both desirable renal as well as hemodynamic effects and thus offer an especially ideal profile for the treatment of patients with heart failure. The provision of such combined vasopressin antagonists also appears to make sense inasmuch as a volume diminution mediated solely via V2 receptor blockade can entail the stimulation of osmoreceptors and, as a result, may lead to a further compensatory increase in vasopressin release. Through this, in the absence of a component simultaneously blocking the V1a receptor, the harmful effects of vasopressin, such as for example vasoconstriction and heart muscle hypertrophy, could be further intensified [Saghi P. et al., *Europ. Heart J.* 26, 538-543 (2005)].

V1a receptors are mainly located on vascular smooth muscle cells (VSMC) but also on cardiomyocytes, fibroblasts and specialized renal cells like glomerular mesangial cells or cells of the macula densa which control the release of renin [Wasilewski M A, Myers V D, Recchia F A, Feldman A M, Tilley D G, Cell Signal., 28(3), 224-233, (2016)]. The activation of VSMC V1a receptor by vasopressin gives rise to intracellular calcium release and according vasoconstriction. Therefore, stimulation of VSMC V1a receptors causes increased vascular resistance and increased cardiac afterload. Cardiac output is adversely affected by V1a-mediated vasoconstriction. The increase in afterload and direct stimulation of V1a receptors on cardiomyocytes can lead to cardiac hypertrophy and remodeling including fibrosis. Mice with cardiac-specific overexpression of V1a receptor develop cardiac hypertrophy leading to dilation and left ventricular dysfunction, suggesting an essential role for V1a receptor in the development of heart failure [Li X, Chan T O, Myers V, Chowdhury I, Zhang X Q, Song J, Zhang J, Andrel J, Funakoshi H, Robbins J, Koch W J, Hyslop T, Cheung J Y, Feldman A M, Circulation.; 124, 572-581 (2011)].

V1a receptor is also expressed in the renal cortical and medullary vasculature, where it mediates vasoconstriction of renal vessels and thus affecting overall renal blood flow. Thus, the activation of V1a receptor can decrease renal medullary blood flow inducing further pathological processes as tissue hypoxia, reduced oxygen and accordingly energy supply for tubular transport processes as well as direct damages of mesangial and macula densa cells. It has been demonstrated that mesangial V1a receptor activation mediates TGFβ signaling and causes an increase in production of collagen IV. While this signaling contributes extracellular matrix accumulation and remodeling in the kidney, similar signaling pathways are believed to occur in cardiac cells especially after myocardial infarction, which emphasizes the central role of V1a receptor in the development of hypertrophic and fibrotic processes in response to pathophysiological elevated vasopressin levels [Wasilewski M A, Myers V D, Recchia F A, Feldman A M, Tilley D G. Arginine vasopressin receptor signaling and functional outcomes in heart failure. Cell Signal., 28(3), 224-233 (2016)].

Since V1a receptors are mainly expressed on VSMCs and thus participate in vascular function, a link to vascular diseases as peripheral arterial disease (PAD) including claudication and critical limb ischemia as well as coronary microvascular dysfunction (CMD) is conceivable.

Apart from this, V1a receptors are also expressed on human platelets and in the liver. The meaning of platelet V1a receptors is not fully understood although vasopressin induces aggregation of human platelets via V1a receptor at high concentrations ex vivo. Therefore, inhibition of vasopressin-induced platelet aggregation by V1a receptor antagonists is a useful pharmacological ex vivo assay making use of human tissue endogenously expressing the V1a receptor [Thibonnier M, Roberts J M, J Clin Invest.; 76:1857-1864, (1985)].

Vasopressin stimulates gluconeogenesis and glycogenolysis via activation of the hepatic V1a receptor. Animal studies have shown that vasopressin impairs glucose tolerance which could be inhibited by a V1a receptor antagonist thereby providing a link of vasopressin receptor V1a to diabetes mellitus. [Taveau C, Chollet C, Waeckel L, Desposito D, Bichet D G, Arthus M F, Magnan C, Philippe E, Paradis V, Foufelle F, Hainault I, Enhorning S, Velho G, Roussel R, Bankir L, Melander O, Bouby N. Vasopressin and hydration play a major role in the development of glucose intolerance and hepatic steatosis in obese rats. Diabetologia., 58(5), 1081-1090, (2015)]. Vasopressin was shown to contribute to the development of albuminuria and to diabetes-induced nephropathy in animal models. This observation is consistent with epidemiological findings in humans.

It was found recently that vasopressin also seems to play a causal role in the development of preeclampsia. Chronic infusion of vasopressin during pregnancy in mice is sufficient to induce all of the major maternal and fetal phenotypes associated with human preeclampsia, including pregnancy-specific hypertension [Santillan M K, Santillan D A, Scroggins S M, Min J Y, Sandgren J A, Pearson N A, Leslie K K, Hunter S K, Zamba G K, Gibson-Corley K N, Grobe J L. Vasopressin in preeclampsia: a novel very early human pregnancy biomarker and clinically relevant mouse model. Hypertension. 64(4), 852-859, (2014)].

Vasopressin levels can be elevated in women with dysmenorrhea (a gynecological disorder which is characterized by cyclical cramping pelvic pain) during menstruation, which appear to increase myometrial smooth muscle contraction. It was found recently that a selective vasopressin V1a receptor antagonist (relcovaptan/SR-49059) can reduce intrauterine contractions elicited by vasopressin.

For these reasons, agents which inhibit the action of vasopressin on the V1a receptor appear suitable for the treatment of several cardiovascular diseases. In particular, agents which inhibit the action of vasopressin selectively on the V1a receptor offer an especially ideal profile for the treatment of otherwise normovolemic patients, i.e. those which are not eligible for decongestion by e.g. high doses of loop diuretics or V2 antagonists, and where induced aquaresis via V2 inhibition may be undesired.

Certain 4-phenyl-1,2,4-triazol-3-yl derivatives have been described in WO 2005/063754-A1 and WO 2005/105779-A1 to act as vasopressin V1a receptor antagonists that are useful for the treatment of gynecological disorders, notably menstrual disorders such as dysmenorrhea.

In WO 2011/104322-A1, a particular group of bis-aryl-bonded 1,2,4-triazol-3-ones, including 5-phenyl-1,2,4-triazol-3-yl and 1-phenyl-1,2,3-triazol-4-yl derivatives thereof, has been disclosed as antagonists of vasopressin V1a and/or V2 receptors being useful for the treatment and/or prevention of cardiovascular diseases.

In WO 2016/071212, a particular group of 5-(hydroxyalkyl)-1-phenyl-1,2,4-triazole derivatives have been disclosed as potent dual antagonists of vasopressin V1a and V2 receptors that are useful for the treatment and/or prevention of cardiovascular and renal diseases.

SUMMARY

It was an object of the present invention to provide novel compounds which act as potent selective or dual V1a/V2 receptor antagonists and as such are suitable for the treatment and/or prevention of diseases, more particularly for the treatment and/or prevention of renal and/or cardiovascular disorders.

The compounds of the present invention have valuable pharmacological properties and can be used for the prevention and/or treatment of various diseases and disease-induced states in humans and other mammals.

In one aspect, the present invention relates to 3-(hydroxyalkyl)-1,2,4-triazole derivatives of the general formula (I)

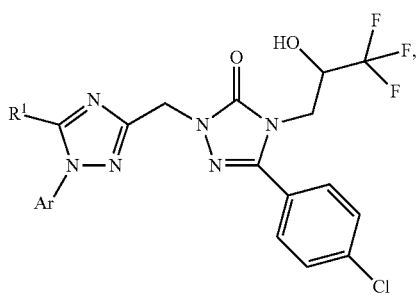

(I)

in which
R$^1$ represents a group of the formula

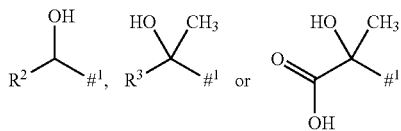

in which
$^1$ represents the point of attachment to the rest of the molecule,
R$^2$ represents a group selected from trifluoromethyl and (C$_2$-C$_4$)-alkyl, wherein any (C$_2$-C$_4$)-alkyl group is optionally substituted with up to three fluorine atoms,
R$^3$ represents (C$_1$-C$_4$)-alkyl,
wherein any (C$_1$-C$_4$)-alkyl group is optionally substituted with up to three fluorine atoms,
Ar represents a phenyl group or a 5- or 6-membered heteroaryl group attached via a ring carbon atom having one, two or three ring heteroatoms selected from N, O and S,
wherein any phenyl group and any 5- or 6-membered heteroaryl group are each optionally substituted, identically or differently, with one or two groups selected from halogen, nitro, cyano, (C$_1$-C$_4$)-alkyl, (C$_1$-C$_4$)-alkoxy, (C$_1$-C$_4$)-alkylsulfanyl, (C$_1$-C$_4$)-alkoxycarbonyl, aminocarbonyl and —S(=O)$_2$NH$_2$,
wherein said (C$_1$-C$_4$)-alkyl group, said (C$_1$-C$_4$)-alkoxy group and said (C$_1$-C$_4$)-alkylsulfanyl group are each optionally substituted with up to three fluorine atoms.

The compounds according to this invention can also be present in the form of their salts, solvates and/or solvates of the salts.

DETAILED DESCRIPTION OF A PREFERRED EMBODIMENT

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon atom or heteroatom.

When groups in the compounds according to the invention are substituted, it is possible for said groups to be mono-substituted or poly-substituted with substituent(s), unless otherwise specified. Within the scope of the present invention, the meanings of all groups which occur repeatedly are independent from one another. It is possible that groups in the compounds according to the invention are substituted with one, two or three identical or different substituents.

The term "comprising" when used in the specification includes "consisting of".

If within the present text any item is referred to as "as mentioned herein", it means that it may be mentioned anywhere in the present text.

The terms as mentioned in the present text have the following meanings:

The term "C$_1$-C$_4$", as used in the present text, e.g. in the context of the definition of "C$_1$-C$_4$-alkyl", "C$_1$-C$_4$-alkoxy", "or "C$_1$-C$_4$-alkylsulfanyl", means an alkyl group having a finite number of carbon atoms of 1 to 4, i.e. 1, 2, 3, or 4 carbon atoms.

The term "C$_1$-C$_4$-alkyl" means a linear or branched, saturated, monovalent hydrocarbon group having 1, 2, 3, or 4 carbon atoms, e.g. a methyl, ethyl, propyl, isopropyl, butyl, sec-butyl, isobutyl, tert-butyl, or an isomer thereof. Particularly, said group has 1, 2, 3 or 4 carbon atoms ("C$_1$-C$_4$-alkyl"), e.g. a methyl, ethyl, propyl, isopropyl, butyl, sec-butyl isobutyl, or tert-butyl group, more particularly 1, 2 or 3 carbon atoms ("C$_1$-C$_3$-alkyl"), e.g. a methyl, ethyl, n-propyl or isopropyl group, even more particularly a methyl group.

The term "C$_2$-C$_4$", as used in the present text, e.g. in the context of the definition of "C$_2$-C$_4$-alkyl", means an alkyl group having a finite number of carbon atoms of 2 to 4, i.e. 2, 3, or 4 carbon atoms.

The term "C$_2$-C$_4$-alkyl" means a linear or branched, saturated, monovalent hydrocarbon group having 2, 3, or 4 carbon atoms, e.g. an ethyl, propyl, isopropyl, butyl, sec-butyl, isobutyl, tert-butyl, or an isomer thereof. Particularly, said group has 2, 3 or 4 carbon atoms ("C$_2$-C$_4$-alkyl"), e.g. an ethyl, propyl, isopropyl, butyl, sec-butyl isobutyl, or tert-butyl group, more particularly 2 or 3 carbon atoms ("C$_2$-C$_3$-alkyl"), e.g. an ethyl, n-propyl or isopropyl group, even more particularly an ethyl group.

The term "5- to 6-membered heteroaryl" means a monovalent, monocyclic aromatic ring having 5 or 6 ring atoms, which contains at least one ring heteroatom and optionally one, two or three further ring heteroatoms selected from a nitrogen atom, an oxygen atom and a sulfur atom, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

Particularly, the heteroaryl group in substituent Ar in the general formula (I), supra, is a pyridinyl, a pyrazinyl, a pyridazinyl, an imidazolyl or a thiazolyl group.

The term "halogen" means a fluorine, chlorine, bromine or iodine atom, particularly a fluorine or chlorine atom.

The term "$C_1$-$C_4$-alkylsulfanyl" means a linear or branched, saturated, monovalent group of formula ($C_1$-$C_4$-alkyl)-S—, in which the term "$C_1$-$C_4$-alkyl" is as defined supra, e.g. a methylsulfanyl, ethylsulfanyl, propylsulfanyl, isopropylsulfanyl, butylsulfanyl, sec-butylsulfanyl, isobutylsulfanyl, tert-butylsulfanyl group.

The term "$C_1$-$C_4$-alkoxy" means a linear or branched, saturated, monovalent group of formula ($C_1$-$C_4$-alkyl)-O—, in which the term "$C_1$-$C_4$-alkyl" is as defined supra, e.g. a methoxy, ethoxy, n-propoxy, isopropoxy, n-butoxy, sec-butoxy, isobutoxy, tert-butoxy, or an isomer thereof.

The term "($C_1$-$C_4$)-alkoxycarbonyl" means a straight-chain or branched alkoxy group having 1, 2, 3 or 4 carbon atoms which is bound to the rest of the molecule via a carbonyl group [—C(=O)—], such as: methoxycarbonyl, ethoxycarbonyl, n-propoxycarbonyl, isopropoxycarbonyl, n-butoxycarbonyl, and tert-butoxycarbonyl, for example.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as process products and/or embodiment examples and their salts, solvates and solvates of the salts, where the compounds included in the formula (I) and mentioned in the following are not already salts, solvates and solvates of the salts.

Salts for the purposes of the present invention are preferably pharmaceutically acceptable salts of the compounds according to the invention (for example, see S. M. Berge et al., "Pharmaceutical Salts", *J. Pharm. Sci.* 1977, 66, 1-19). Salts which are not themselves suitable for pharmaceutical uses but can be used, for example, for isolation, purification or storage of the compounds according to the invention are also included.

Pharmaceutically acceptable salts include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, formic acid, acetic acid, trifluoroacetic acid, propionic acid, lactic acid, tartaric acid, malic acid, citric acid, fumaric acid, maleic acid, and benzoic acid.

Pharmaceutically acceptable salts also include salts of customary bases, such as for example alkali metal salts (for example sodium and potassium salts), alkaline earth metal salts (for example calcium and magnesium salts), and ammonium salts derived from ammonia or organic amines, such as illustratively and preferably ethylamine, diethylamine, triethylamine, N,N-diisopropylethylamine, monoethanolamine, diethanolamine, triethanolamine, dimethyloethanol, choline, diethylaminoethanol, procaine, dicyclohexylamine, dibenzylamine, N-methylmorpholine, N-methylpiperidine, arginine, lysine, and 1,2-ethylenediamine.

Solvates in the context of the invention are designated as those forms of the compounds according to the invention which form a complex in the solid or liquid state by stoichiometric coordination with solvent molecules. Hydrates are a specific form of solvates, in which the coordination takes place with water. Hydrates are preferred solvates in the context of the present invention.

The compounds of this invention may, either by nature of asymmetric centers or by restricted rotation, be present in the form of isomers (enantiomers, diastereomers). Any isomer may be present in which the asymmetric center is in the (R)-, (S)-, or (R,S)-configuration.

It will also be appreciated that when two or more asymmetric centers are present in the compounds of the invention, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the invention.

All isomers, whether separated, pure, partially pure, or in racemic mixture, of the compounds of this invention are encompassed within the scope of this invention. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by resolution.

In addition, all possible tautomeric forms of the compounds described above are included according to the present invention.

The present invention also encompasses all suitable isotopic variants of the compounds according to the invention. An isotopic variant of a compound according to the invention is understood to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, fluorine, chlorine, bromine and iodine, such as $^2$H (deuterium), $^3$H (tritium), $^{13}$C, $^{14}$C, $^{15}$N, $^{17}$O, $^{18}$O, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body. Due to comparatively easy preparability and detectability, especially compounds labelled with $^3$H, $^{14}$C and/or $^{18}$F isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required. Such modifications of the compounds according to the invention may therefore in some cases also constitute a preferred embodiment of the present invention. Isotopic variants of the compounds according to the invention can be prepared by processes known to those skilled in the art, for example by the methods described below and the methods described in the working examples, by using corresponding isotopic modifications of the particular reagents and/or starting compounds therein.

In a distinct embodiment, the present invention relates to compounds of formula (I), supra, wherein
$R^1$ represents a group of the formula

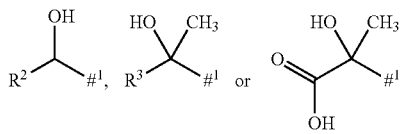

in which
$\#^1$ represents the point of attachment to the rest of the molecule,
$R^2$ represents a group selected from trifluoromethyl and $(C_2-C_4)$-alkyl, wherein any $(C_2-C_4)$-alkyl group is optionally substituted with up to three fluorine atoms,
$R^3$ represents $(C_1-C_4)$-alkyl,
wherein any $(C_1-C_4)$-alkyl group is optionally substituted with up to three fluorine atoms,
Ar represents a group selected from phenyl or pyridyl,
wherein any phenyl group and any pyridyl group is each optionally substituted, identically or differently, with one or two groups selected from halogen, cyano, $(C_1-C_4)$-alkyl, $(C_1-C_4)$-alkoxy and aminocarbonyl,
wherein said $(C_1-C_4)$-alkyl group or said $(C_1-C_4)$-alkoxy group are each optionally substituted with up to three fluorine atoms,
or a pharmaceutically acceptable salt, hydrate and/or solvate thereof.

In a preferred embodiment, the present invention relates to compounds of formula (I), supra, wherein
$R^1$ represents a group of the formula

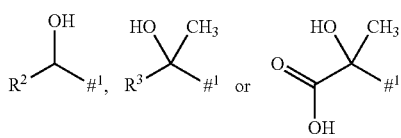

in which
$\#^1$ represents the point of attachment to the rest of the molecule,
$R^2$ represents an ethyl group,
$R^3$ represents a methyl group,
Ar represents a group of the formula

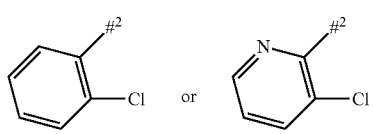

in which
$\#^2$ represents the point of attachment to the nitrogen atom,
or a pharmaceutically acceptable salt, hydrate and/or solvate thereof.

In a preferred embodiment, the present invention relates to compounds of formula (I), supra, wherein
$R^1$ represents a group of the formula

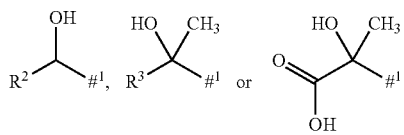

in which
$\#^1$ represents the point of attachment to the rest of the molecule,
$R^2$ represents a group selected from trifluoromethyl and ethyl,
$R^3$ represents a methyl group,
Ar represents a group of the formula

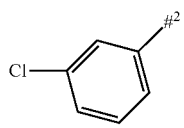

in which
$\#^2$ represents the point of attachment to the nitrogen atom,
or a pharmaceutically acceptable salt, hydrate and/or solvate thereof.

In accordance with a further preferred embodiment, the present invention covers compounds of general formula (I), supra, wherein
$R^1$ represents a group of the formula

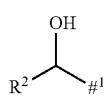

in which
$\#^1$ represents the point of attachment to the rest of the molecule,
$R^2$ represents an ethyl group,
or a pharmaceutically acceptable salt, hydrate and/or solvate thereof.

In accordance with a further preferred embodiment, the present invention covers compounds of general formula (I), supra, wherein
$R^1$ represents a group of the formula

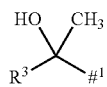

in which
$\#^1$ represents the point of attachment to the rest of the molecule,
$R^3$ represents a methyl group,
or a pharmaceutically acceptable salt, hydrate and/or solvate thereof.

In accordance with a further preferred embodiment, the present invention covers compounds of general formula (I), supra, wherein R¹ represents a group of the formula

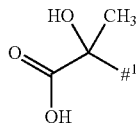

in which
¹ represents the point of attachment to the rest of the molecule,
or a pharmaceutically acceptable salt, hydrate and/or solvate thereof.

In accordance with a further preferred embodiment, the present invention covers compounds of general formula (I), supra, wherein
Ar represents a group of the formula

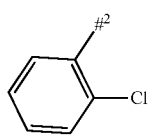

in which
² represents the point of attachment to the nitrogen atom,
or a pharmaceutically acceptable salt, hydrate and/or solvate thereof.

In accordance with a further preferred embodiment, the present invention covers compounds of general formula (I), supra, wherein
Ar represents a group of the formula

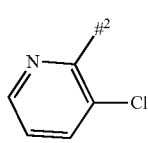

in which
² represents the point of attachment to the nitrogen atom,
or a pharmaceutically acceptable salt, hydrate and/or solvate thereof.

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of compounds of general formula (I), supra.

The present invention covers any sub-combination within any embodiment or aspect of the present invention of intermediate compounds of general formula (II), (III), (IV), (V), (VI), (VII), (XI), (XII), (XIII), (XV), (XVI), (XVIII), (XX), (XXI), (XXII), (XXIV), (XXV), (XXVI), (XXVII), (XXVIII), (XXIX), (XXX), (XXXI), (XXXII) and (XXXIII). The present invention covers the compounds of general formula (I) which are disclosed in the Example Section of this text, infra.

In accordance with a second aspect, the present invention covers methods of preparing compounds of general formula (I) as defined supra, said methods comprising the step [A] of allowing an intermediate compound of formula (II):

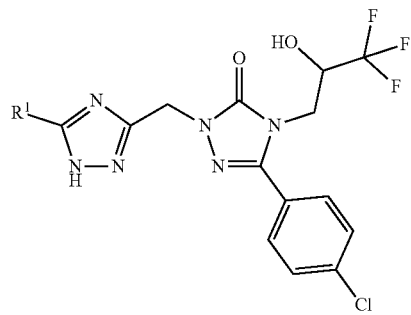

(II)

in which
R¹ represents a group of the formula

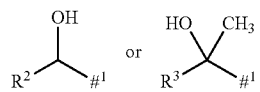

in which
¹, R² and R³ are as defined for the compound of general formula (I) as defined supra,
to react with a compound of general formula (III):

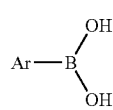

(III)

in which
Ar is as defined for the compound of general formula (I) as defined supra, in the presence of a copper catalyst and an amine base thereby giving a compound of general formula (I-A):

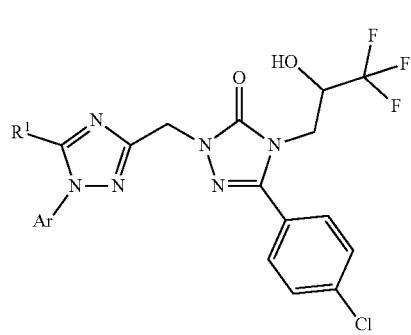

(I-A)

in which
R¹ represents a group of the formula

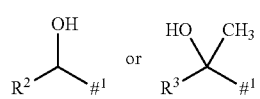

in which
¹, R² and R³ are as defined for the compound of general formula (I) as defined supra, Ar is as defined for the compound of general formula (I) as defined supra, or

[B] of allowing an intermediate compound of formula (IV):

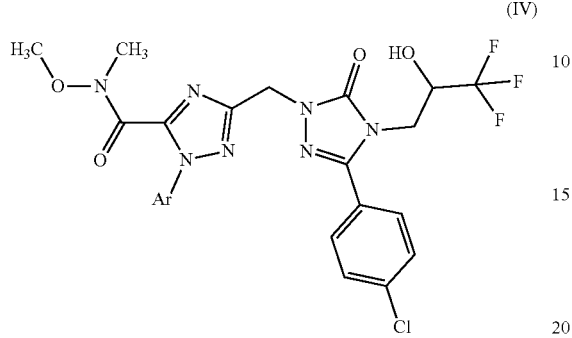
(IV)

in which

Ar is as defined for the compound of general formula (I) as defined supra, to react with a compound of general formula (V):

(V)

in which

R² is as defined for the compound of general formula (I) as defined supra,

X represents chloride, bromide or iodide, to give an intermediate compound of general formula (VI):

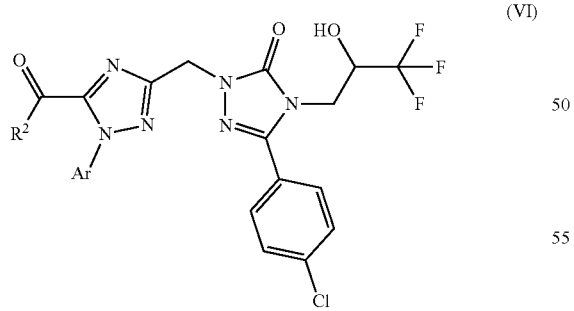
(VI)

in which

R² and Ar are as defined for the compound of general formula (I) as defined supra, which is then allowed to react in a second step with a suitable reduction reagent, such as sodium borohydride, thereby giving a compound of general formula (I-B):

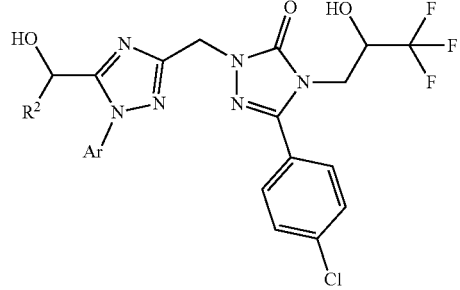
(I-B)

in which

R² and Ar are as defined for the compound of general formula (I) as defined supra, or

[C] of allowing an intermediate compound of formula (VII):

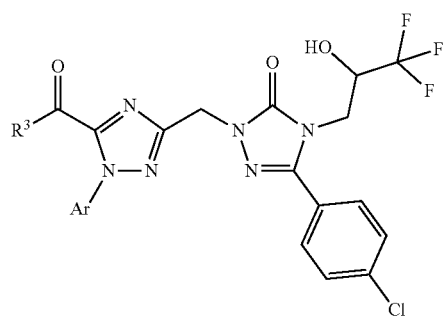
(VII)

in which

R³ and Ar are as defined for the compound of general formula (I) as defined supra, to react with a compound of general formula (VIII):

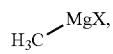
(VIII)

in which

X represents chloride, bromide or iodide, thereby giving a compound of general formula (I-C):

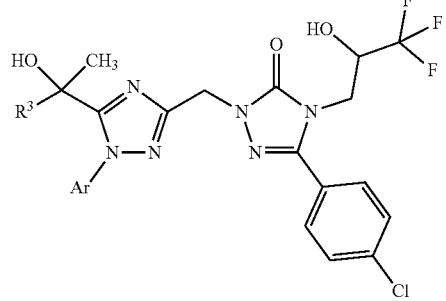
(I-C)

in which

R³ and Ar are as defined for the compound of general formula (I) as defined supra, each [A], [B] and [C] optionally followed, where appropriate, by (i) separating the compounds of formula (I) thus obtained into their respective enantiomers or diastereomers, and/or (ii) converting the compounds of formula (I) into their respective hydrates, solvates, salts and/or hydrates or solvates of the salts by treatment with the corresponding solvents and/or acids or bases.

The present invention covers methods of preparing compounds of the present invention of general formula (I), said methods comprising the steps as described in the Experimental Section herein.

The compounds of the formula (I-A), (I-B), (I-C) and (I-D) form a subset of compounds of the formula (I) according to the invention.

The schemes and procedures described below illustrate synthetic routes to the compounds of general formula (I) of the invention and are not intended to be limiting. It is clear to the person skilled in the art that the order of transformations as exemplified in schemes 1, 2, 3, 4 and 5 can be modified in various ways. The order of transformations exemplified in these schemes is therefore not intended to be limiting. In addition, interconversion of any of the substituents, $R^1$, $R^2$, $R^3$, $R^{3,4}$, $R^4$, $R^5$, Ar, X and PG can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3rd edition, Wiley 1999). Specific examples are described in the subsequent paragraphs.

The coupling reaction (II)+(III)→(I-A) is typically carried out with the aid of a copper catalyst and an amine base ["Chan-Lam coupling" conditions; see, for instance, D. M. T. Chan et al., *Tetrahedron Lett.* 44 (19), 3863-3865 (2003); J. X. Qiao and P. Y. S. Lam, *Synthesis*, 829-856 (2011); K. S. Rao and T.-S. Wu, *Tetrahedron* 68, 7735-7754 (2012)]. Copper catalysts suitable for this process are in particular copper(II) salts, such as copper(II) acetate, copper(II) trifluoromethane-sulfonate or copper(II) bromide. Practical amine bases include, for example, triethylamine, N,N-diisopropylethylamine, pyridine and 4-(N,N-dimethylamino) pyridine. The reaction is performed in an inert organic solvent, such as dichloromethane, 1,2-dichloroethane, methyl tert-butyl ether, tetrahydrofuran, 1,4-dioxane, 1,2-dimethoxyethane, toluene, pyridine, ethyl acetate, acetonitrile or N,N-dimethylformamide, or in a mixture of these solvents. Preferably, pyridine is used both as solvent and base. The coupling is generally carried out at a temperature in the range of +20° C. to +120° C., preferably at +20° C. to +70° C. Concomitant microwave irradiation may have a beneficial effect in this reaction as well.

The reaction (IV)+(V)→(VI) is carried out with the aid of an alkyl-magnesium halide (Grignard reagent). A Grignard reagent suitable for this process is in particular alkyl-magnesium bromide. The reaction is performed in an inert organic solvent, such as ethers or hydrocarbon solvents. Preferably, THF or diethylether or a mixture thereof is used. The coupling is generally carried out at a temperature in the range of −78° C. to +25° C., preferably at 0° C.

The subsequent reduction of the carbonyl group (VI)→(I-B) is carried out with a reduction reagent. Reduction reagents suitable for this process are in particular sodium borohydride, lithium aluminium hydride or lithium borohydride. Preferably, sodium borohydride is used. The reaction is performed in an organic solvent, such as ethanol, diethylether or THF. Preferably, ethanol is used. The reduction reaction is generally carried out at a temperature in the range of −20° C. to +25° C., preferably at 0° C.

The reaction (VII)+(VIII)→(I-C) is carried out with the aid of methylmagnesium halide (Grignard reagent). A Grignard reagent suitable for this process is in particular methylmagnesium bromide. The reaction is performed in an inert organic solvent, such as ethers or hydrocarbon solvents. Preferably, THF is used. The coupling is generally carried out at a temperature in the range of −20° C. to +25° C., preferably at 0° C.

Compounds of general formula (II) as defined supra, can be prepared by allowing compound of formula (IX):

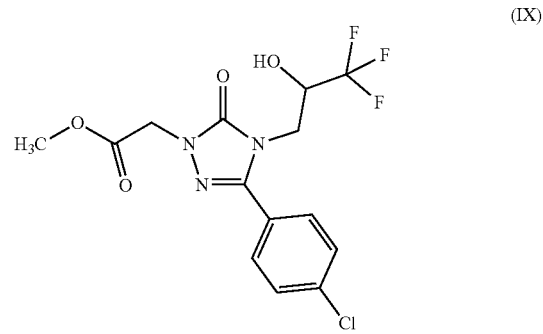

(IX)

to first react with hydrazine to give the hydrazide of formula (X):

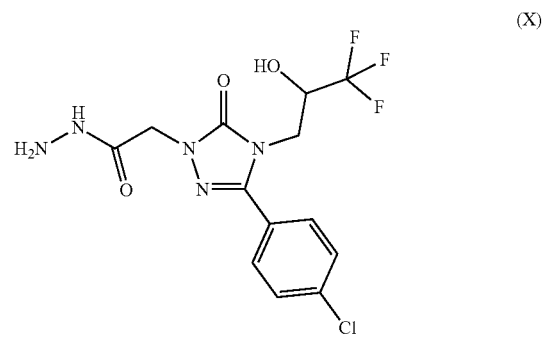 [SMILES: NNC(=O)Cn1nc(-c2ccc(Cl)cc2)n(CC(O)C(F)(F)F)c1=O]

(X)

which is then being condensed with an amidine of formula (XI) or (XII):

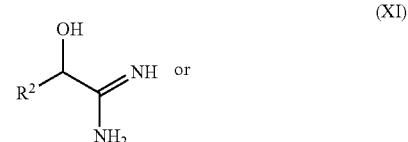

(XI)

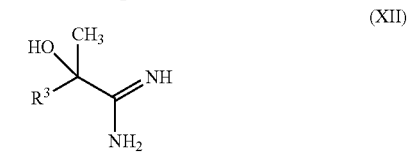

(XII)

or a salt thereof, in which

R² and R³ are as defined for the compound of general formula (I) as defined supra, in the presence of a base to give a 1,2,4-triazole derivative of formula (II)

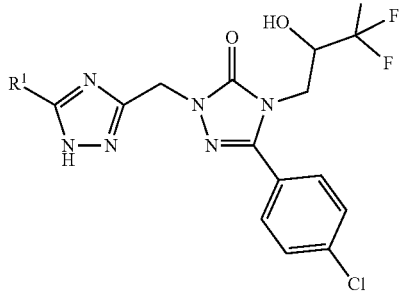

(II)

in which

R¹ is as defined for the compound of general formula (II) as defined supra.

The transformation (IX)→(X) is carried out in the usual way by treating the methyl ester of formula (IX) with hydrazine or hydrazine hydrate in an alcoholic solvent, such as methanol, ethanol, n-propanol, isopropanol or n-butanol, at a temperature in the range of +20° C. to +100° C.

The condensation reaction (X)→(II) is usually carried out in an inert dipolar-aprotic solvent, such as N,N-dimethylformamide (DMF), N,N-dimethylacetamide (DMA), dimethylsulfoxide (DMSO), N-methylpyrrolidinone (NMP) or N,N'-dimethylpropylene urea (DMPU), in the presence of a sufficiently strong base, such as sodium hydride or a sodium or potassium alkoxide, for example sodium or potassium methoxide, sodium or potassium ethoxide, or sodium or potassium tert-butoxide. The amidine of formula (XI) or (XII) may be employed as such in this reaction or in salt form, e.g. as the hydrochloride salt. In the latter case, a proportional excess of base is used. The reaction is generally performed at a temperature between +80° C. and +150° C. Heating by means of a microwave reactor device may have a beneficial effect for this condensation reaction.

The 1,2,4-triazole derivative of formula (II) produced by this reaction may also be present in other tautomeric forms, such as (II-A) or (II-B):

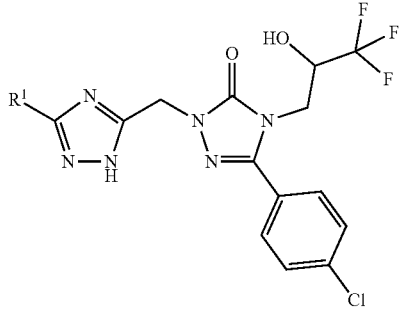

(II-A)

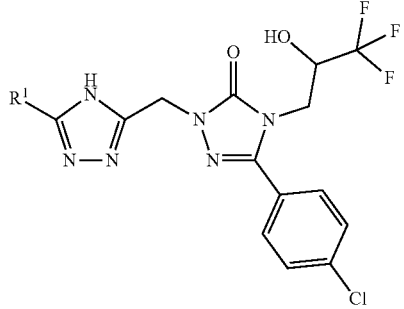

(II-B)

in which

R¹ is as defined for the compound of general formula (II) as defined supra, or as a mixture of tautomers.

Compounds of formula (II), can also be obtained in diastereomerically pure form by employing the appropriate enantiomer of amidine of formula (XI), i.e. (XI-A) or (XI-B):

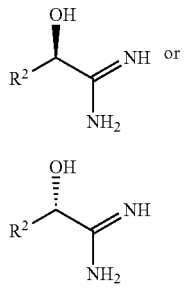

(XI-A)

(XI-B)

in which

R² is as defined for the compound of general formula (I) as defined supra, or by employing the appropriate enantiomer of amidine of formula (XII), i.e. (XII-A) or (XII-B):

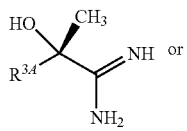

(XII-A)

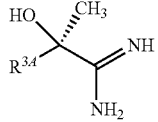

(XII-B)

in which

R³ᴬ represents a group selected from monofluoromethyl, difluoromethyl, trifluoromethyl and (C₂-C₄)-alkyl,
    wherein any (C₂-C₄)-alkyl group is optionally substituted with up to three fluorine atoms, or a salt thereof, in the condensation reaction described above.

Compounds of general formula (IV) as defined supra, can be prepared as shown in the synthetic scheme 1 below:

Scheme 1

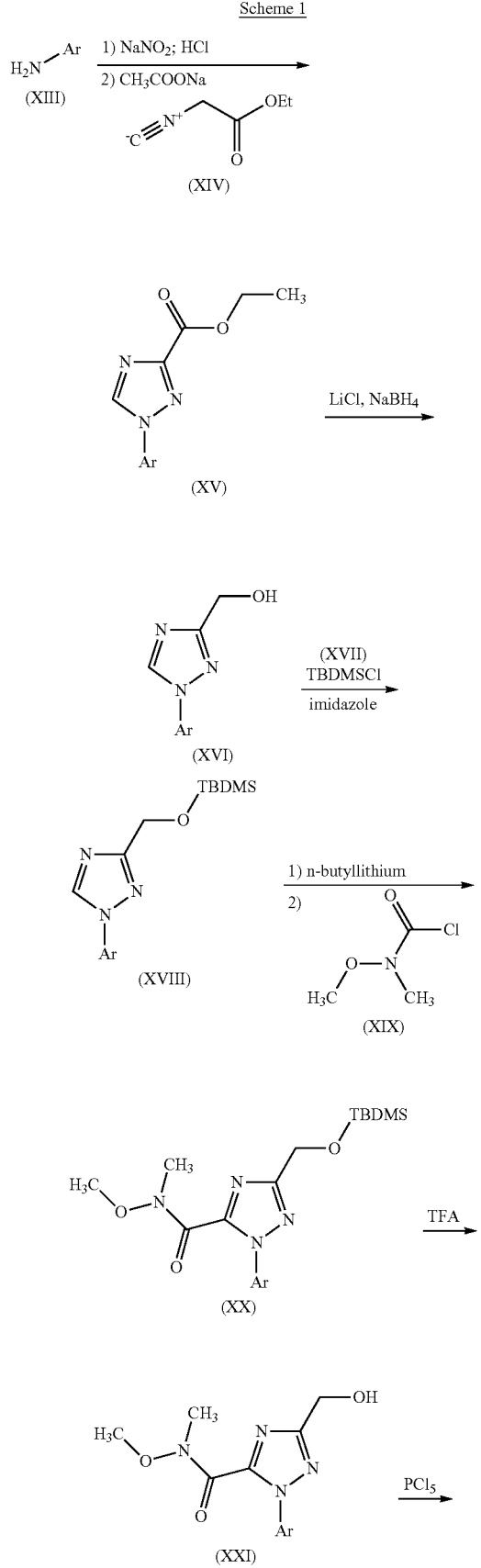

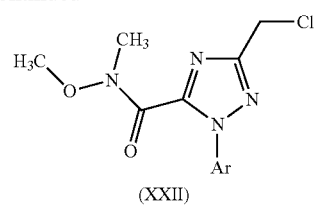

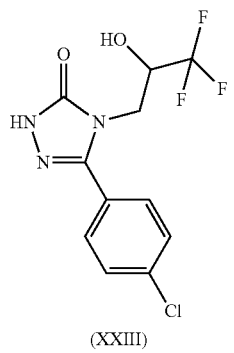

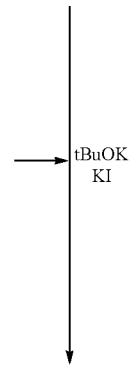

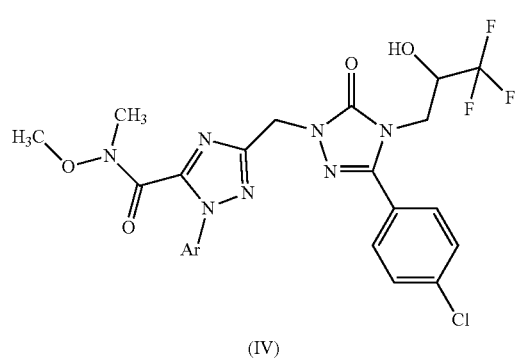

[TBDMSCl: tert-butyldimethylsilylchloride, TBDMS: tert-butyldimethylsilyl, TFA: trifluoroacetic acid, tBuOK, potassium tert-butoxide]

For the reaction (XIII)→(XV) the temperature is maintained between 0° C. and 5° C. and water is used as solvent. The following step (XV)→(XVI) is performed under an argon atmosphere at room temperature in a mixture of tetrahydrofuran and ethanol as solvent. Introduction of the TBDMS-group (XVI)→(XVIII) is carried out in DMF at room temperature. For the coupling reaction (XVIII)→(XX) n-butyl lithium and N-Methoxy-N-methylcarbamoyl chloride (XIX) are added successively to (XVIII) at −78° C. in tetrahydrofuran as solvent. Reactions (XX)→(XxI) and (XxI)→(XXII) are performed at room temperature in dichloromethane. Coupling reaction (XXII)+(XXIII)→(IV) is carried out under argon atmosphere at room temperature with a catalytic amount of potassium iodide in acetonitrile.

Compounds of general formula (VII) as defined supra, can be prepared as shown in the synthetic scheme 2 below:

Scheme 2

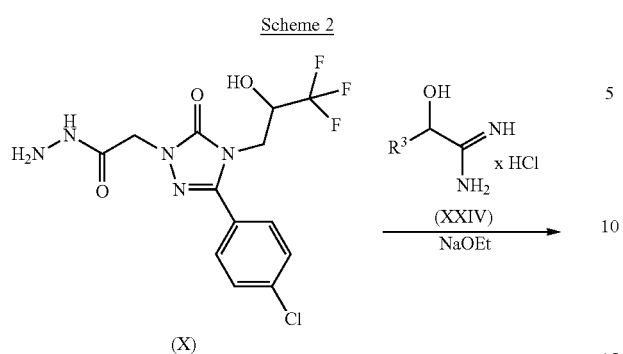

(X)

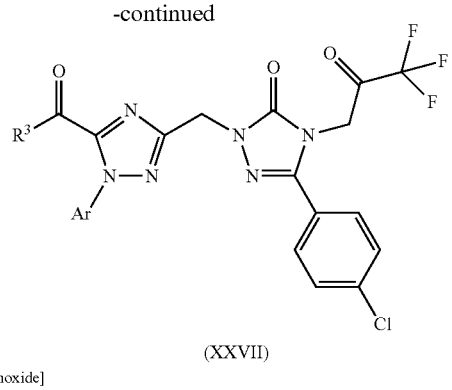

(XXIV)
NaOEt

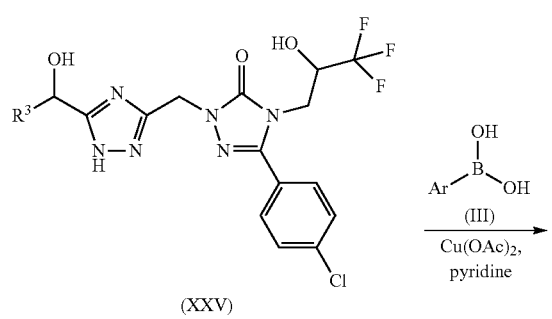

(XXV)

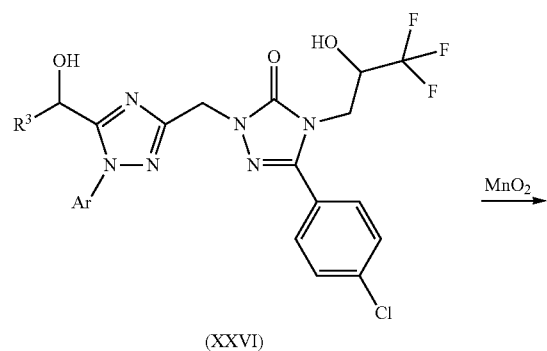

(XXVI)

MnO₂

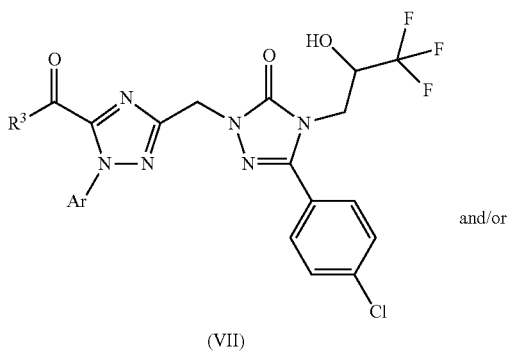

(VII)

and/or

-continued (XXVII)

[NaOEt: sodium ethoxide]

The condensation reaction (X)→(XXV) is carried out in a similar manner as described above for the transformations (X)→(II). Reaction conditions for the coupling reaction (XXV)→(XXVI) correspond to those described for reaction (II)+(III)→(I-A).

The oxidation reaction (XXVI)→(VII) is carried out using customary oxidation methods known from the literature [e.g. JOC, 1983, 48, 4155 (Dess Martin oxidation); Tet Lett, 1994, 35, 3485 (IBX oxidation); JOC, 1970, 35, 3589 (acid dichromate oxidation); Tet Lett, 1979, 399 (PDC oxidation); Tetrahedron, 1978, 34, 1651 (swern oxidation), Bulletin of the Chemical Society of Japan, 1990, vol. 63, 7, 1888 (manganese(IV) oxide oxidation)]. Thus, the alcohol group adjacent to R³ in the compounds of the general formula (XXVI) is preferably oxidized using Dess-Martin periodinane (DMP) or manganese(IV) oxide. In a typical procedure the reaction is carried out in dichloromethane at a temperature of 0° C. and subsequent warming up to room temperature. The selectivity towards monoketone (VII) or diketone (XXVII) may be controlled via the specific oxidation agent as apparent to the person skilled in the art and/or via the amount of oxidation agent added.

Analogous to the preparation of compounds of the formula (VI), compounds of general formula (VII) can be alternatively prepared by adding a Grignard reagent of general formula (V-I):

(V-I)

in which
R³ is as defined for the compound of general formula (I) as defined supra,
X represents chloride, bromide or iodide,
to a compound of general formula (II).
Compounds of general formula (I-D):

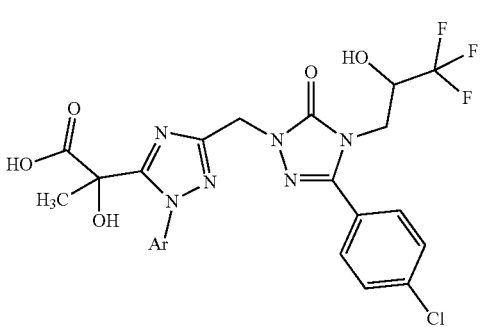

(I-D)

can be prepared by allowing compound of formula (XXVIII):

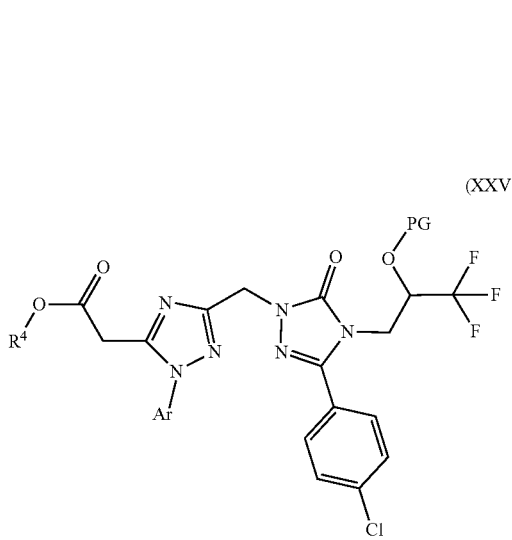

(XXVIII)

in which

Ar is as defined for the compound of general formula (I) as defined supra, $R^4$ represents a $(C_1-C_4)$-alkyl group, in particular a methyl group, PG represents a suitable alcohol protecting group, such as tert-butyldimethylsilyl, to react with sodium hydride, methyliodide and an oxygen source, thereby giving an intermediate compound of general formula (XXIX):

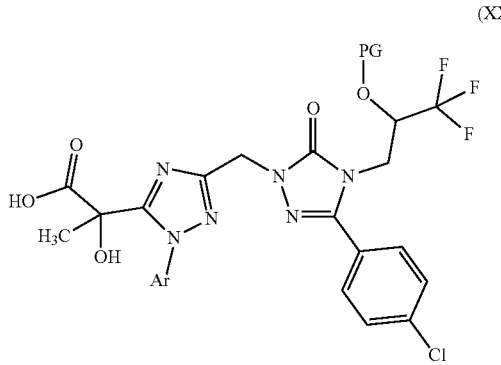

(XXIX)

in which

Ar is as defined for the compound of general formula (I) as defined supra,

PG represents a suitable alcohol protecting group, such as tert-butyldimethylsilyl, followed by alcohol deprotection of (XXIX) with a suitable deprotection agent thereby giving a compound of general formula (I-D):

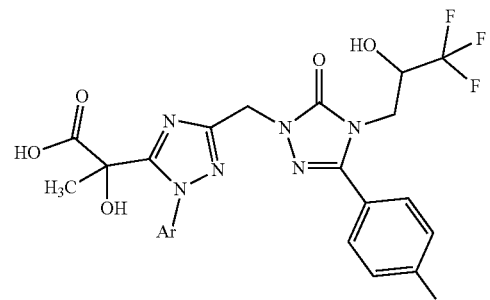

(I-D)

in which

Ar is as defined for the compound of general formula (I) as defined supra.

The reaction (XXVIII)→(XXIX) is carried out with the aid of a base and a methylating reagent. Bases suitable for this process are in particular sodium hydride, lithium hydride or potassium hydride. Preferably, sodium hydride is used as base. Methylating reagents suitable for this process are in particular methyliodide, methyl p-toluenesulfonate, methyltrifluoromethanesulfonate or dimethylsulfate. Preferably, methyliodide is used as methylating reagent. The oxygen for the simultaneous hydroxylation reaction presumably results from the atmospheric oxygen being present in the reaction vessel.

The saponification of the ester group within the transformation (XXVIII)→(XXIX) usually happens spontaneously in the reaction vessel, but may also be conducted subsequently by common saponification methods known to the person skilled in the art, such as treatment with an alkali base, for example aqueous lithium hydroxide or sodium hydroxide, in methanol as the solvent.

The removal of the protective group (PG) in the process step (XXIX)→(I-D) is carried out by customary methods known from the literature [see, for example, T. W. Greene and P. G. M. Wuts, *Protective Groups in Organic Synthesis*, Wiley, New York, 1999]. Thus, the tert-butyldimethylsilyl group is preferably removed with the aid of a solution containing fluoride ions, such as a tetra-n-butyl-ammonium fluoride (TBAF) solution.

Both steps are performed in an inert organic solvent, such as tetrahydrofuran or diethylether. Preferably tetrahydrofuran is used as solvent. Both steps are generally carried out at a temperature in the range of −10° C. to +60° C., preferably at 0° C.

Compounds of general formula (XXVIII) as defined supra, can be prepared by allowing an intermediate compound of formula (XXX):

(XXX)

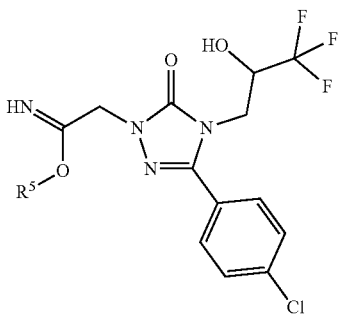

in which
R⁵ represents a (C₁-C₄)-alkyl group, in particular a methyl group,
to react in a first step in the presence of an at least stoichiometric amount of a base with a compound of general formula (XXXI):

(XXXI)

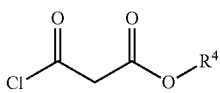

in which
R⁴ represents a (C₁-C₄)-alkyl group, in particular a methyl group,
to give an intermediate compound, which is then allowed to react in a second step with a hydrazine compound of general formula (XXXII):

(XXXII)

in which
Ar is as defined for the compound of general formula (I) as defined supra,
or a respective salt thereof,
thereby giving an intermediate compound of general formula (XXXIII):

(XXXIII)

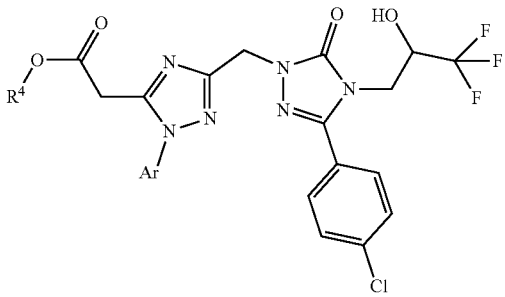

in which
R⁴ represents a (C₁-C₄)-alkyl group, in particular a methyl group,

Ar is as defined for the compound of general formula (I) as defined supra,
followed by alcohol protection of (XXXIII) with a suitable protection agent thereby giving a compound of general formula (XXVIII):

(XXVIII)

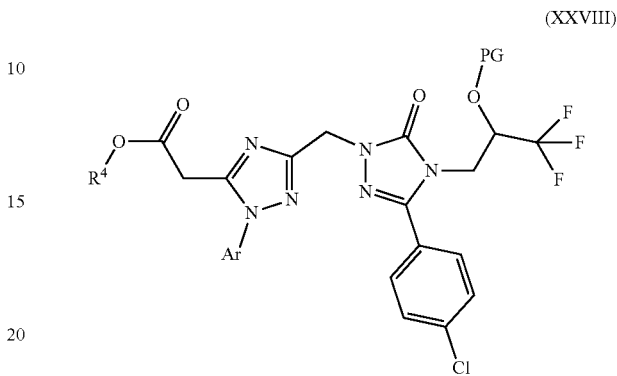

in which
R⁴ represents a (C₁-C₄)-alkyl group, in particular a methyl group,
Ar is as defined for the compound of general formula (I) as defined supra
PG represents a suitable alcohol protecting group, such as tert-butyldimethylsilyl.

The multicomponent cyclization (XXX)→(XXXIII) is carried out by first reacting imidate of formula (XXX) with an acid chloride of formula (XXXI) in the presence of a base to form an intermediate which is in a subsequent step reacted with the hydrazine compound of formula (XXXII). Typically the formed intermediate is not isolated and the transformation over the two steps is performed in one-pot. The hydrazine compound of formula (XXXII) may also be used in form of its salts, such as a hydrochloride salt or a toluenesulfonic acid salt. Under the alkaline reaction conditions, the hydrazine salt will be reconverted into the free base form. The amount of base added may then be adjusted in this respect. It may be beneficial in the second step to add a copper or zinc salt, such as copper(II) sulfate, copper(II) chloride, zinc(II) sulfate and zinc(II) chloride. Typically and preferably copper(II)sulfate is used.

Suitable bases for both steps of the cyclization are typically tertiary amine bases, such as N,N-diisopropylethylamine (DIPEA), triethylamine, triisopropylamine, N-methylimidazole, N-methylmorpholine, pyridine and 4-(N,N-dimethylamino)pyridine. Preferably, N,N-diisopropylethylamine (DIPEA) is used as base. The reaction is performed in an inert organic solvent, such as dichloromethane, 1,2-dichloroethane, methyl tert-butyl ether, tetrahydrofuran, 1,4-dioxane, 1,2-dimethoxyethane, toluene, pyridine, ethyl acetate, acetonitrile or N,N-dimethyl-formamide, or in a mixture of these solvents. Preferably tetrahydrofuran or dioxane or a mixture thereof are used as solvents. The first step is generally carried out at a temperature in the range of −10° C. to +120° C., preferably at 0° C. The second step is generally carried out at a temperature in the range of +20° C. to +120° C., preferably at room temperature. Concomitant microwave irradiation may have a beneficial effect in this reaction as well at a temperature in the range of +60° C. to +150° C., preferably at +120° C.

Introduction of the protective group (PG) (XXXIII)→(XXVIII) is carried out by customary methods known from the literature [see, for example, T. W. Greene and P. G. M. Wuts, *Protective Groups in Organic Synthesis*, Wiley, New York, 1999], for example with tert-butyldimethylchlorosilane and imidazole in dimethylformamide.

Compounds of general formula (XXX) as defined supra, can be prepared by a method comprising the step

[a] of allowing a compound of formula (XXIII):

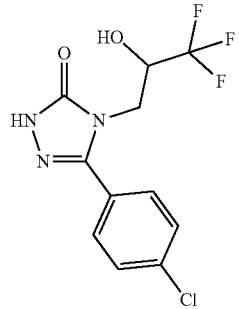

(XXIII)

to react with a nitrile compound of general formula (XXXIV):

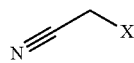

(XXXIV)

in which

X represents a leaving group, such as chloride, bromide, iodide, mesylate or tosylate, in particular chloride or bromide, thereby giving a compound of general formula (XXXV):

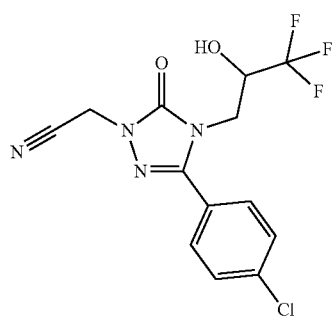

(XXXV)

followed by a subsequent step

[b] of allowing the compound of formula (XXXV) obtained in step [a] to react with a basic alcoholate, preferably sodium methanolate, thereby giving a compound of general formula (XXX),

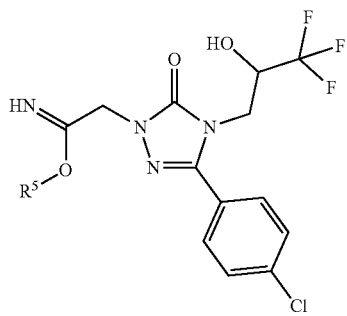

(XXX)

in which $R^5$ represents a $(C_1-C_4)$-alkyl group, in particular a methyl group.

The N-alkylation reaction (XXIII)+(XXXIV) 4 (XXXV) (step [a]) is typically carried out in the presence of a base. Typical and exemplary bases include sodium carbonate, potassium carbonate, cesium carbonate, N,N-diisopropylethylamine, triethylamine, sodium tert-butylate or potassium tert-butylate in acetonitrile, methylisobutylketone, dioxane, dimethylformamide, dimethylacetamide, N-methylpyrrolidinone, dimethylsulfoxide and sulfolane, preference is given to potassium carbonate in methylisobutylketone or acetonitrile. The reaction may optionally be carried out in an advantageous manner with addition of an alkylation catalyst such as, for example, lithium bromide, sodium iodide, lithium iodide, tetra-n-butylammoniumbromide, tetra-n-butyl-ammoniumiodide or benzyltriethylammoniumchloride. The reactions are generally carried out in a temperature range of from +40° C. to +120° C., preferably at from +60° C. to +80° C. The reactions can be carried out at atmospheric, at elevated or at reduced pressure (for example at from 0.5 to 5 bar); in general, the reactions are carried out at atmospheric pressure. It may be advantageous to slowly perform the addition of the alkylation agent (XXXIV) over a longer time span.

Conversion to the imidates of general formula (XXX) can be achieved via standard reaction protocols known to the person skilled in the art (step [b]: (XXXV)→(XXX)). The reaction is typically carried out under basic reactions conditions by reacting with a basic alcoholate. Typical bases, which may be used are sodium methanolate, sodium ethanolate, sodium propanolate, sodium isopropoxide, sodium tert-butylate or potassium tert-butylate in methanol, ethanol, n-propanol, isopropanol, n-butanol, isobutanol and tert-butanol. Preference is given to sodium methanolate in methanol. The reactions are generally carried out in a temperature range of from +20° C. to +80° C., preferably at from +20° C. to +60° C.

Alternatively, the nitrile compounds of general formula (XXXV) may optionally also be prepared as shown in the synthetic scheme 3 below:

Scheme 3

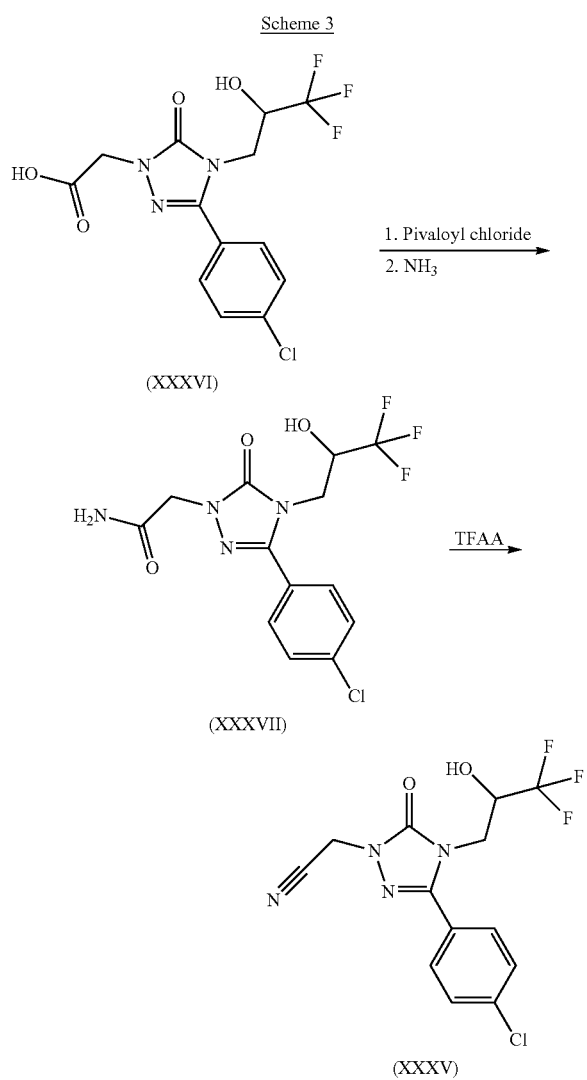

[TFAA = trifluoroacetic acid anhydride]

The amide coupling (XXXVI)→(XXXVII) can be carried out directly with the help of a condensing agent or activating agent in the presence of a base or over two steps via an acyl chloride or carboxylic acid imidazolide. Typical condensation and activating agents for the amide formation in process step (XXXVI)→(XXXVII) include, for example, carbodiimides such as N,N'-diethyl-, N,N'-dipropyl-, N,N'-diisopropyl-N,N'-dicyclohexylcarbodiimide (DCC) or N-(3-dimethylamino-isopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium-3-sulphate or 2-tert-butyl-5-methylisoxazolium perchlorate, acylamino compounds such as 2-ethoxy-1-ethoxycarbonyl-1,2-dihydroquinoline, or isobutyl chloroformate, propanephosphonic anhydride, diethyl cyanophosphonate, bis(2-oxo-3-oxazo-lidinyl)phosphoryl chloride, benzotriazol-1-yloxytris(dimethylamino) phosphonium hexafluorophosphate, benzotriazol-1-yloxy-tris(pyrrolidino)phosphonium hexafluorophosphate (PyBOP), O-(benzotriazol-1-yl)-N,N, N',N'-tetramethyluronium tetrafluoroborate (TBTU), O-(benzotriazol-1-yl)-N,N, N',N'-tetramethyl-uronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N', N'-tetramethyluroniumhexafluoro-phosphate (HATU) or O-(1H-6-chloro-benzotriazol-1-yl)-1,1,3,3-tetramethyluronium tetrafluoro-borate (TCTU), optionally in combination with other additives such as 1-hydroxybenzotriazole (HOBt) or N-hydroxysuccinimide (HOSu). The acyl chlorides are typically prepared with thionyl chloride or oxalyl chloride in an inert solvent like dichloromethane or N,N-dimethylformamide. It is also possible to use mixtures of the solvents mentioned.

The conversion to the nitrile (XXXVII)→(XXXV) can be carried out with the help of dehydrating agent. Typical dehydrating agents include, for example trifluoroacetic acid anhydride, phosphorous pentoxide ($P_4O_{10}$), phosphoryl chloride ($POCl_3$), phosphorous pentachloride ($PCl_5$), $CCl_4$—$PPh_3$ (Appel reagent), hexamethylphosphoramide (HMPA); methyl N-(triethylammoniumsulfonyl)carbamate (Burgess reagent), (Chloromethylene)dimethyliminium chloride (Vilsmeier reagent), oxalyl chloride/DMSO and thionylchloride ($SOCl_2$).

Typical and exemplary solvents for step (XXXVII)→(XXXV) include for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil, fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulfoxide, N,N-dimethylformamide, N,N'-dimethylpropyleneurea (DMPU) or N-methylpyrrolidone (NMP). It is also possible to use mixtures of the solvents mentioned.

In a typical and preferred procedure the carboxylic acid (XXXVI) is first reacted with pivaloyl chloride in the presence of pyridine to form an intermediate which is in a subsequent step reacted with ammonia. Typically the formed intermediate is not isolated and the reaction over the two steps is performed in one-pot. The conversion of carboxamide (XXXVII) into nitrile (XXXV) is then typically performed by reaction with trifluoroacetic anhydride in pyridine.

The compounds of formula (IX), (XXIII) and (XXXVI) can be synthesized by the procedures described in Int. Pat. Appl. WO 2010/105770 and WO 2011/104322 (see also synthesis schemes 4 and 5 below).

The compounds of the formula (III), (V), (VIII), (XI), (XI-A), (XI-B), (XII), (XII-A), (XII-B), (XIII), (XIV), (XVII), (XIX), (XXIV), (XXXI), (XXXII) and (XXXIV) are either commercially available, known from the literature, or can be prepared from readily available starting materials by adaptation of standard methods described in the literature. Detailed procedures and literature references for preparing the starting materials can also be found in the Experimental Part in the section on the preparation of the starting materials and intermediates.

Scheme 4

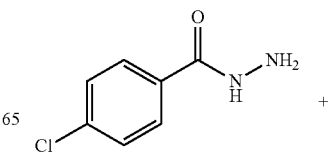

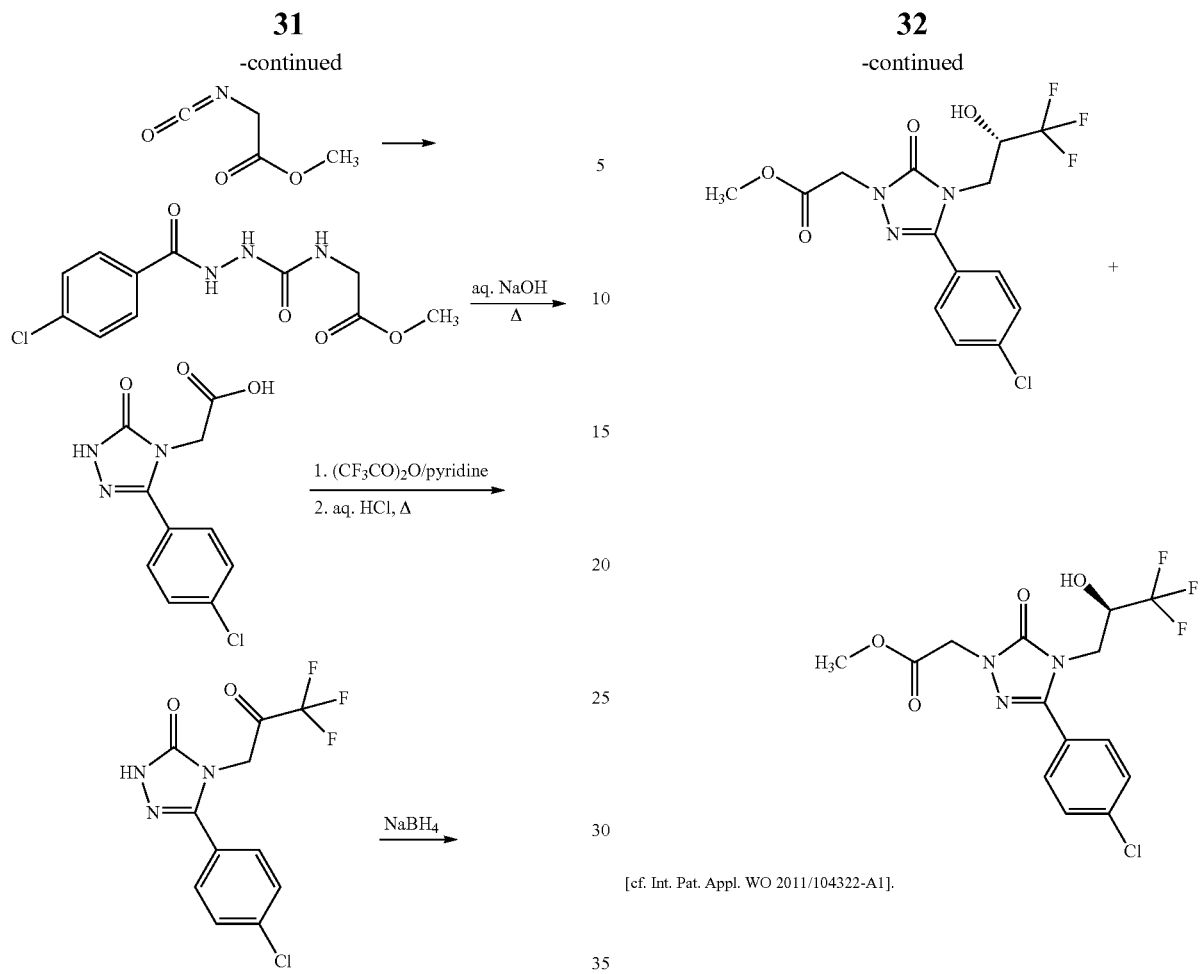
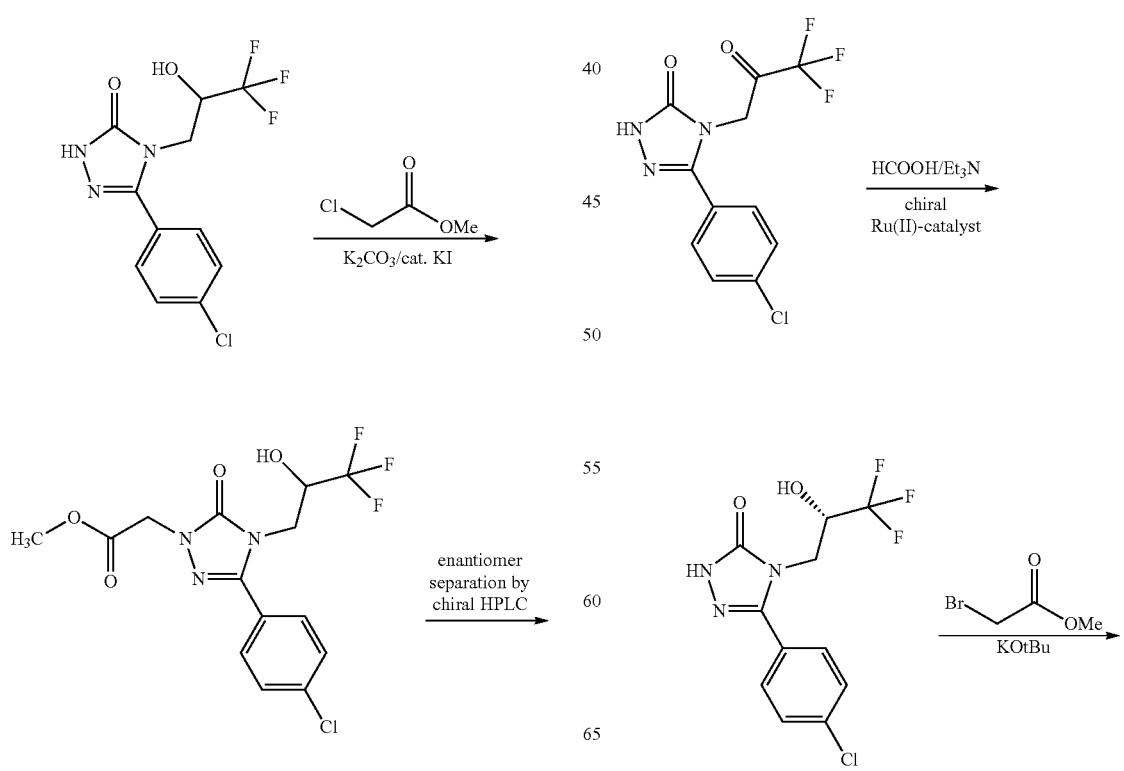
[cf. Int. Pat. Appl. WO 2011/104322-A1].
Scheme 5

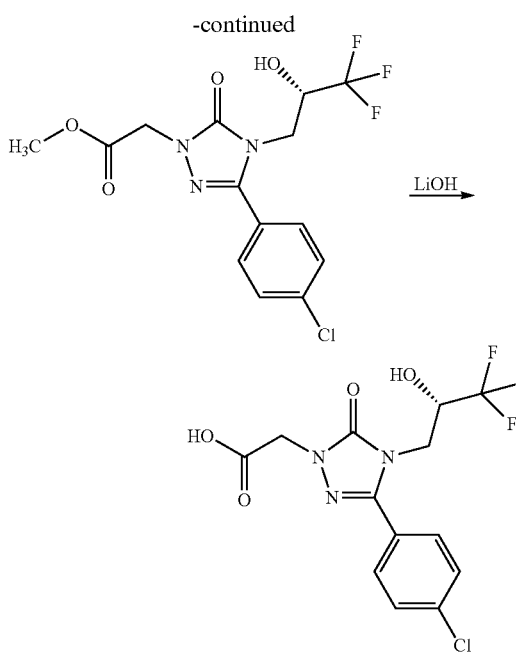

[cf. Int. Pat. Appl. WO 2011/104322-A1].

The compounds of the present invention have valuable pharmacological properties and can be used for the prevention and/or treatment of various diseases and disease-induced states in humans and other mammals.

In the context of the present invention, the term "treatment" or "treating" includes inhibiting, delaying, relieving, mitigating, arresting, reducing, or causing the regression of a disease, disorder, condition, or state, the development and/or progression thereof, and/or the symptoms thereof. The term "prevention" or "preventing" includes reducing the risk of having, contracting, or experiencing a disease, disorder, condition, or state, the development and/or progression thereof, and/or the symptoms thereof. The term prevention includes prophylaxis. Treatment or prevention of a disorder, disease, condition, or state may be partial or complete.

Throughout this document, for the sake of simplicity, the use of singular language is given preference over plural language, but is generally meant to include the plural language if not otherwise stated. For example, the expression "A method of treating a disease in a patient, comprising administering to a patient an effective amount of a compound of formula (I)" is meant to include the simultaneous treatment of more than one disease as well as the administration of more than one compound of formula (I).

In the context of the present invention, the term "treatment" or "treating" includes inhibiting, delaying, relieving, mitigating, arresting, reducing, or causing the regression of a disease, disorder, condition, or state, the development and/or progression thereof, and/or the symptoms thereof. The term "prevention" or "preventing" includes reducing the risk of having, contracting, or experiencing a disease, disorder, condition, or state, the development and/or progression thereof, and/or the symptoms thereof. The term prevention includes prophylaxis. Treatment or prevention of a disorder, disease, condition, or state may be partial or complete.

Throughout this document, for the sake of simplicity, the use of singular language is given preference over plural language, but is generally meant to include the plural language if not otherwise stated. For example, the expression "A method of treating a disease in a patient, comprising administering to a patient an effective amount of a compound of formula (I)" is meant to include the simultaneous treatment of more than one disease as well as the administration of more than one compound of formula (I).

The compounds of the present invention are potent selective or dual antagonists of vasopressin V1a and V2 receptors. The compounds of the invention are therefore expected to be highly valuable as therapeutic agents for the treatment and/or prevention of diseases, in particular for the treatment and/or prevention of cardiovascular and renal diseases.

The compounds according to the invention are suitable for the treatment and/or prevention of renal diseases, in particular of acute and chronic kidney diseases, diabetic kidney diseases, and of acute and chronic renal failure. The compounds according to the invention may further be used for the treatment and/or prevention of sequelae of acute kidney injury arising from multiple insults such as ischemia-reperfusion injury, radiocontrast administration, cardiopulmonary bypass surgery, shock and sepsis. In the sense of the present invention, the term renal failure or renal insufficiency comprises both acute and chronic manifestations of renal insufficiency, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, Alport syndrome, kidney inflammation, immunological kidney diseases such as kidney transplant rejection, immune complex-induced kidney diseases, nephropathy induced by toxic substances, contrast medium-induced nephropathy; minimal change glomerulonephritis (lipoid); Membranous glomerulonephritis; focal segmental glomerulosclerosis (FSGS); hemolytic uremic syndrome (HUS), amyloidosis, Goodpasture's syndrome, Wegener's granulomatosis, Purpura Schonlein-Henoch, diabetic and non-diabetic nephropathy, pyelonephritis, renal cysts, nephrosclerosis, hypertensive nephrosclerosis and nephrotic syndrome, which can be characterized diagnostically, for example, by abnormally reduced creatinine and/or water excretion, abnormally increased blood concentrations of urea, nitrogen, potassium and/or creatinine, altered activity of renal enzymes such as, for example, glutamyl synthetase, altered urine osmolarity or urine volume, increased microalbuminuria, macroalbuminuria, lesions of glomeruli and arterioles, tubular dilatation, hyperphosphataemia and/or the need for dialysis. The present invention also comprises the use of the compounds according to the invention for the treatment and/or prevention of sequelae of renal insufficiency, for example pulmonary edema, heart failure, uraemia, anaemia, electrolyte disturbances (e.g. hyperkalaemia, hyponatraemia) and disturbances in bone and carbohydrate metabolism. The compounds according to the invention are also suitable for the treatment and/or prevention of polycystic kidney disease (PCKD) and of the syndrome of inadequate ADH secretion (SIADH).

Cardiovascular diseases in this context that may be treated and/or prevented with the compounds of the invention include, but are not limited to, the following: acute and chronic heart failure including worsening chronic heart failure (or hospitalization for heart failure) and congestive heart failure, arterial hypertension, resistant hypertension, arterial pulmonary hypertension, coronary heart disease, stable and unstable angina pectoris, atrial and ventricular arrhythmias, disturbances of atrial and ventricular rhythm and conduction disturbances, for example atrioventricular blocks of degree I-III (AVB I-III), supraventricular tachyarrhythmia, atrial fibrillation, atrial flutter, ventricular fibrillation, ventricular flutter, ventricular tachyarrhythmia, torsade-de-pointes tachycardia, atrial and ventricular extrasystoles, AV-junction extrasystoles, sick-sinus syndrome, syncopes, AVnode re-entry tachycardia and Wolff-Parkinson-White syndrome, acute coronary syndrome (ACS), autoimmune heart diseases (pericarditis, endocarditis, valvulitis, aortitis, cardiomyopathies), shock such as cardiogenic shock, septic shock and anaphylactic shock, aneurysms, Boxer cardiomyopathy (premature ventricular contraction), furthermore thromboembolic diseases and ischaemias such as peripheral perfusion disturbances, reperfusion injury, arterial and venous thromboses, myocardial insufficiency, endothelial dysfunction, micro- and macrovascular damage (vasculitis) and for preventing restenoses such as after thrombolysis therapies, percutaneous transluminal angioplasty (PTA), percutaneous transluminal coronary angioplasty (PTCA), heart transplantation and bypass operations, arteriosclerosis, disturbances of lipid metabolism, hypolipoproteinaemias, dyslipidemias, hypertriglyceridemias, hyperlipidemias and combined hyperlipidemias, hypercholesterolaemias, abetalipoproteinaemia, sitosterolemia, xanthomatosis, Tangier disease, adipositas, obesity, metabolic syndrome, transitory and ischemic attacks, stroke, inflammatory cardiovascular diseases, peripheral and cardiac vascular diseases, peripheral circulation disorders, spasms of the coronary arteries and peripheral arteries, and edema such as, for example, pulmonary edema, cerebral edema, renal edema and heart failure-related edema.

In the sense of the present invention, the term heart failure also includes more specific or related disease forms such as right heart failure, left heart failure, global insufficiency, ischemic cardiomyopathy, dilatative cardiomyopathy, congenital heart defects, heart valve defects, heart failure with heart valve defects, mitral valve stenosis, mitral valve insufficiency, aortic valve stenosis, aortic valve insufficiency, tricuspidal stenosis, tricuspidal insufficiency, pulmonary valve stenosis, pulmonary valve insufficiency, combined heart valve defects, heart muscle inflammation (myocarditis), chronic myocarditis, acute myocarditis, viral myocarditis, diabetic heart failure, alcoholtoxic cardiomyopathy, cardiac storage diseases, heart failure with preserved ejection fraction (HFpEF or diastolic heart failure), and heart failure with reduced ejection fraction (HFrEF or systolic heart failure).

The compounds according to the invention are also suitable for the treatment and/or prevention of renal diseases, in particular of acute and chronic renal insufficiency, and of acute and chronic renal failure. In the sense of the present invention, the term renal insufficiency comprises both acute and chronic manifestations of renal insufficiency, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney transplant rejection, immune complex-induced kidney diseases, nephropathy induced by toxic substances, contrast medium-induced nephropathy, diabetic and non-diabetic nephropathy, pyelonephritis, renal cysts, nephrosclerosis, hypertensive nephrosclerosis and nephrotic syndrome, which can be characterized diagnostically, for example, by abnormally reduced creatinine and/or water excretion, abnormally increased blood concentrations of urea, nitrogen, potassium and/or creatinine, altered activity of renal enzymes such as, for example, glutamyl synthetase, altered urine osmolarity or urine volume, increased microalbuminuria, macroalbuminuria, lesions of glomeruli and arterioles, tubular dilatation, hyperphosphataemia and/or the need for dialysis. The present invention also comprises the use of the compounds according to the invention for the treatment and/or prevention of sequelae of renal insufficiency, for example pulmonary edema, heart failure, uraemia, anaemia, electrolyte disturbances (e.g. hyperkalaemia, hyponatraemia) and disturbances in bone and carbohydrate metabolism.

The compounds of the present invention may be particularly useful for the treatment and/or prevention of the cardiorenal syndrome (CRS) and its various subtypes. This term embraces certain disorders of the heart and kidneys whereby acute or chronic dysfunction in one organ may induce acute or chronic dysfunction of the other. CRS has been sub-classified into five types based upon the organ that initiated the insult as well as the acuity and chronicity of the disease (type 1: development of renal insufficiency resulting from acute decompensated heart failure; type 2: chronic congestive heart failure resulting in progressive renal dysfunction; type 3: acute cardiac dysfunction resulting from an abrupt fall in renal function; type 4: chronic kidney disease leading to cardiac remodeling; type 5: systemic disease involving both the heart and the kidneys) [see, for example, M. R. Kahn et al., *Nature Rev. Cardiol.* 10, 261-273 (2013)].

The compounds according to the invention are also suitable for the treatment and/or prevention of polycystic kidney disease (PCKD) and of the syndrome of inadequate ADH secretion (SIADH). Furthermore, the compounds of the invention are suitable for use as a diuretic for the treatment of edemas and in electrolyte disorders, in particular in hypervolemic and euvolemic hyponatremia.

Moreover, the compounds according to the invention may be used for the treatment and/or prevention of peripheral arterial disease (PAD) including claudication and critical limb ischemia as well as coronary microvascular dysfunction (CMD) including CMD type 1-4, primary and secondary Raynaud's phenomenon, microcirculation disturbances, claudication, peripheral and autonomic neuropathies, diabetic microangiopathies, diabetic retinopathy, diabetic limb ulcers, gangrene, CREST syndrome, erythematous disorders, onychomycosis, rheumatic diseases and for promoting wound healing.

Furthermore, the compounds of the invention are suitable for treating urological diseases and diseases of the male and female urogenital system such as, for example, benign prostatic syndrome (BPS), benign prostatic hyperplasia (BPH), benign prostatic enlargement (BPE), bladder outlet obstruction (BOO), lower urinary tract syndromes (LUTS), neurogenic overactive bladder (OAB), interstitial cystitis (IC), urinary incontinence (UI), for example mixed, urge, stress and overflow incontinence (MUI, UUI, SUI, OUI), pelvic pains, erectile dysfunction, dysmenorrhea and endometriosis.

The compounds according to the invention may also be used for the treatment and/or prevention of inflammatory diseases, asthmatic diseases, chronic obstructive pulmonary disease (COPD), acute respiratory distress syndrome (ARDS), acute lung injury (ALI), alpha-1-antitrypsin deficiency (AATD), pulmonary fibrosis, pulmonary emphysema (e.g. smoking-induced pulmonary emphysema) and cystic fibrosis (CF). In addition, the compounds of the invention may be used for the treatment and/or prevention of pulmonary arterial hypertension (PAH) and other forms of pulmonary hypertension (PH), including pulmonary hypertension associated with left ventricular disease, HIV infection, sickle cell anaemia, thromboembolism (CTEPH), sarcoidosis, chronic obstructive pulmonary disease (COPD) or pulmonary fibrosis.

Additionally, the compounds according to the invention may be used for the treatment and/or prevention of liver cirrhosis, ascites, diabetes mellitus and diabetic complications such as, for example, neuropathy and nephropathy.

Further, the compounds of the invention are suitable for the treatment and/or prevention of central nervous disorders such as anxiety states and depression, of glaucoma and of cancer, in particular of pulmonary tumors, and for the management of circadian rhythm misalignment such as jet lag and shift work.

Furthermore, the compounds according to the invention may be useful for the treatment and/or prevention of pain conditions, diseases of the adrenals such as, for example, pheochromocytoma and adrenal apoplexy, diseases of the intestine such as, for example, Crohn's disease and diarrhea, menstrual disorders such as, for example, dysmenorrhea, or of endometriosis, preterm labor and for tocolysis.

Due to their activity and selectivity profile, the compounds of the present invention are believed to be particularly suitable for the treatment and/or prevention of acute and chronic heart failure, cardiorenal syndrome (type 1-5), hypervolemic and euvolemic hyponatremia, liver cirrhosis, ascites, edema and the syndrome of inadequate ADH secretion (SIADH).kidney diseases including diabetic nephropathy, acute and chronic heart failure, preeclampsia, peripheral arterial disease (PAD) and coronary microvascular dysfunction (CMD), Raynaud's syndrome, dysmenorrhea.

The diseases mentioned above have been well characterized in humans, but also exist with a comparable etiology in other mammals, and may be treated in those with the compounds and methods of the present invention.

Thus, the present invention further relates to the use of the compounds according to the invention for the treatment and/or prevention of diseases, especially of the aforementioned diseases.

The present invention further relates to the use of the compounds according to the invention for preparing a pharmaceutical composition for the treatment and/or prevention of diseases, especially of the aforementioned diseases.

The present invention further relates to the use of the compounds according to the invention in a method for the treatment and/or prevention of diseases, especially of the aforementioned diseases.

The present invention further relates to a method for the treatment and/or prevention of diseases, especially of the aforementioned diseases, by using an effective amount of at least one of the compounds according to the invention.

Compounds of the present invention may be administered as the sole pharmaceutical agent or in combination with one or more additional therapeutic agents as long as this combination does not lead to undesirable and/or unacceptable side effects. Such combination therapy includes administration of a single pharmaceutical dosage formulation which contains a compound of formula (I), as defined above, and one or more additional therapeutic agents, as well as administration of a compound of formula (I) and each additional therapeutic agent in its own separate pharmaceutical dosage formulation. For example, a compound of formula (I) and a therapeutic agent may be administered to the patient together in a single (fixed) oral dosage composition such as a tablet or capsule, or each agent may be administered in separate dosage formulations.

Where separate dosage formulations are used, the compound of formula (I) and one or more additional therapeutic agents may be administered at essentially the same time (i.e., concurrently) or at separately staggered times (i.e., sequentially).

In particular, the compounds of the present invention may be used in fixed or separate combination with antithrombotic agents, for example and preferably from the group of platelet aggregation inhibitors, anticoagulants and profibrinolytic substances;

blood pressure lowering agents, for example and preferably from the group of calcium antagonists, angiotensin AII antagonists, ACE inhibitors, vasopeptidase inhibitors, endothelin antagonists, renin inhibitors, alpha-blockers, beta-blockers, mineralocorticoid receptor antagonists and diuretics;

antidiabetic agents (hypoglycemic or antihyperglycemic agents), such as for example and preferably insulin and derivatives, sulfonylureas, biguanides, thiazolidinediones, acarbose, DPP4 inhibitors, GLP-1 analogues, or SGLT inhibitors (gliflozins).

organic nitrates and NO-donors, for example sodium nitroprusside, nitroglycerin, isosorbide mononitrate, isosorbide dinitrate, molsidomine or SIN-1, and inhalational NO;

compounds that inhibit the degradation of cyclic guanosine monophosphate (cGMP), for example inhibitors of phosphodiesterases (PDE) 1, 2, 5 and/or 9, in particular PDE-5 inhibitors such as sildenafil, vardenafil, tadalafil, udenafil, dasantafil, avanafil, mirodenafil, lodenafil or PF-00489791;

positive-inotropic agents, such as for example cardiac glycosides (digoxin) and beta-adrenergic and dopaminergic agonists such as isoproterenol, adrenalin, noradrenalin, dopamine or dobutamine;

natriuretic peptides, such as for example atrial natriuretic peptide (ANP, anaritide), B-type natriuretic peptide or brain natriuretic peptide (BNP, nesiritide), C-type natriuretic peptide (CNP) or urodilatin;

calcium sensitizers, such as for example and preferably levosimendan;

NO- and heme-independent activators of soluble guanylate cyclase (sGC), such as in particular cinaciguat and also the compounds described in WO 01/19355, WO 01/19776, WO 01/19778, WO 01/19780, WO 02/070462 and WO 02/070510;

NO-independent, but heme-dependent stimulators of guanylate cyclase (sGC), such as in particular riociguat, vericiguat and also the compounds described in WO 00/06568, WO 00/06569, WO 02/42301, WO 03/095451, WO 2011/147809, WO 2012/004258, WO 2012/028647 and WO 2012/059549;

inhibitors of human neutrophil elastase (HNE), such as for example sivelestat or DX-890 (reltran);

compounds inhibiting the signal transduction cascade, in particular tyrosine and/or serine/threonine kinase inhibitors, such as for example nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;

compounds influencing the energy metabolism of the heart, such as for example and preferably etomoxir, dichloroacetate, ranolazine or trimetazidine, or full or partial adenosine A1 receptor agonists as GS-9667 (previously known as CVT-3619), capadenoson and BAY 1067197;

compounds influencing the heart rate, such as for example and preferably ivabradine;

cardiac myosin activators, such as for example and preferably omecamtiv mecarbil (CK1827452);

anti-inflammatory drugs such as non-steroidal anti-inflammatory drugs (NSAIDs) including acetylsalicylic acid (aspirin), ibuprofen and naproxen, glucocorticoids, 5-aminosalicylic acid derivatives, leukotriene antagonists, TNF-alpha inhibitors and chemokine receptor antagonists such as CCR1, 2 and/or 5 inhibitors;

fat metabolism altering agents, for example and preferably from the group of thyroid receptor agonists, cholesterol synthesis inhibitors, such as for example and preferably HMG-CoA-reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

Antithrombotic agents are preferably to be understood as compounds from the group of platelet aggregation inhibitors, anticoagulants and profibrinolytic substances.

In a preferred embodiment of the invention, the compounds according to the invention are administered in combination with a platelet aggregation inhibitor, for example and preferably aspirin, clopidogrel, ticlopidine or dipyridamole.

In a preferred embodiment of the invention, the compounds according to the invention are administered in combination with a thrombin inhibitor, for example and preferably ximelagatran, dabigatran, melagatran, bivalirudin or enoxaparin.

In a preferred embodiment of the invention, the compounds according to the invention are administered in combination with a GPIIb/IIIa antagonist, for example and preferably tirofiban or abciximab.

In a preferred embodiment of the invention, the compounds according to the invention are administered in combination with a factor Xa inhibitor, for example and preferably rivaroxaban, apixaban, otamixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, for example and preferably coumarin.

Blood pressure lowering agents are preferably to be understood as compounds from the group of calcium antagonists, angiotensin AII antagonists, ACE inhibitors, vasopeptidase inhibitors, endothelin antagonists, renin inhibitors, alpha-blockers, beta-blockers, mineralocorticoid receptor antagonists and diuretics.

In a preferred embodiment of the invention, the compounds according to the invention are administered in combination with a calcium antagonist, for example and preferably nifedipine, amlodipine, verapamil or diltiazem.

In a preferred embodiment of the invention, the compounds according to the invention are administered in combination with an alpha-1-receptor blocker, for example and preferably prazosin or tamsulosin.

In a preferred embodiment of the invention, the compounds according to the invention are administered in combination with a beta-blocker, for example and preferably propranolol, atenolol, timolol, pindolol, alprenolol, oxprenolol, penbutolol, bupranolol, metipranolol, nadolol, mepindolol, carazolol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII receptor antagonist, for example and preferably losartan, candesartan, valsartan, telmisartan, irbesartan, olmesartan, eprosartan or azilsartan.

In a preferred embodiment of the invention, the compounds according to the invention are administered in combination with a vasopeptidase inhibitor or inhibitor of neutral endopeptidase (NEP), such as for example and preferably sacubitril, omapatrilat or AVE-7688.

In a preferred embodiment of the invention, the compounds according to the invention are administered in combination with a dual angiotensin AII receptor antagonist/NEP inhibitor (ARNI), for example and preferably LCZ696.

In a preferred embodiment of the invention, the compounds according to the invention are administered in combination with an ACE inhibitor, for example and preferably enalapril, captopril, lisinopril, ramipril, delapril, fosinopril, quinopril, perindopril or trandopril.

In a preferred embodiment of the invention, the compounds according to the invention are administered in combination with an endothelin antagonist, for example and preferably bosentan, darusentan, ambrisentan, tezosentan, sitaxsentan or atrasentan.

In a preferred embodiment of the invention, the compounds according to the invention are administered in combination with a renin inhibitor, for example and preferably aliskiren, SPP-600 or SPP800.

In a preferred embodiment of the invention, the compounds according to the invention are administered in combination with a mineralocorticoid receptor antagonist, for example and preferably finerenone, spironolactone, canrenone, potassium canrenoate, eplerenone, CS-3150, or MT-3995.

In a preferred embodiment of the invention, the compounds according to the invention are administered in combination with a diuretic, such as for example and preferably furosemide, bumetanide, piretanide, torsemide, bendroflumethiazide, chlorothiazide, hydrochlorothiazide, xipamide, indapamide, hydroflumethiazide, methyclothiazide, polythiazide, trichloromethiazide, chlorothalidone, metolazone, quinethazone, acetazolamide, dichlorophenamide, methazolamide, glycerine, isosorbide, mannitol, amiloride or triamterene.

Fat metabolism altering agents are preferably to be understood as compounds from the group of CETP inhibitors, thyroid receptor agonists, cholesterol synthesis inhibitors such as HMG-CoA-reductase or squalene synthesis inhibitors, ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and lipoprotein(a) antagonists.

In a preferred embodiment of the invention, the compounds according to the invention are administered in combination with a CETP inhibitor, for example and preferably dalcetrapib, anacetrapib, BAY 60-5521 or CETP-vaccine (Avant).

In a preferred embodiment of the invention, the compounds according to the invention are administered in combination with a thyroid receptor agonist, for example and preferably D-thyroxin, 3,5,3'-triiodothyronin (T3), CGS 23425 or axitirome (CGS 26214).

In a preferred embodiment of the invention, the compounds according to the invention are administered in combination with an HMG-CoA-reductase inhibitor from the class of statins, for example and preferably lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, for example and preferably BMS-188494 or TAK-475.

In a preferred embodiment of the invention, the compounds according to the invention are administered in combination with an ACAT inhibitor, for example and preferably avasimibe, melinamide, pactimibe, eflucimibe or SMP-797.

In a preferred embodiment of the invention, the compounds according to the invention are administered in combination with an MTP inhibitor, for example and preferably implitapide, R-103757, BMS-201038 or JTT-130.

In a preferred embodiment of the invention, the compounds according to the invention are administered in combination with a PPAR-gamma agonist, for example and preferably pioglitazone or rosiglitazone.

In a preferred embodiment of the invention, the compounds according to the invention are administered in combination with a PPAR-delta agonist, for example and preferably GW 501516 or BAY 68-5042.

In a preferred embodiment of the invention, the compounds according to the invention are administered in combination with a cholesterol absorption inhibitor, for example and preferably ezetimibe, tiqueside or pamaqueside.

In a preferred embodiment of the invention, the compounds according to the invention are administered in combination with a lipase inhibitor, for example and preferably orlistat.

In a preferred embodiment of the invention, the compounds according to the invention are administered in combination with a polymeric bile acid adsorber, for example and preferably cholestyramine, colestipol, colesolvam, CholestaGel or colestimide.

In a preferred embodiment of the invention, the compounds according to the invention are administered in combination with a bile acid reabsorption inhibitor, for example and preferably ASBT (=IBAT) inhibitors such as AZD-7806, S-8921, AK-105, BARI-1741, SC-435 or SC-635.

In a preferred embodiment of the invention, the compounds according to the invention are administered in combination with a lipoprotein(a) antagonist, for example and preferably gemcabene calcium (CI-1027) or nicotinic acid.

In a preferred embodiment of the invention, the compounds according to the invention are administered in combination with antidiabetics (hypoglycemic or antihyperglycemic agents), such as for example and preferably insulin and derivatives, sulfonylureas such as tolbutamide, carbutamide, acetohexamide, chlorpropamide, glipizide, gliclazide, glibenclamide, glyburide, glibornuride, gliquidone, glisoxepide, glyclopyramide, glimepiride, JB253 and JB558, meglitinides such as repaglinide and nateglinide, biguanides such as metformin and buformin, thiazolidinediones such as rosiglitazone and pioglitazone, alpha-glucosidase inhibitors such as miglitol, acarbose and voglibose, DPP4 inhibitors such as vildagliptin, sitagliptin, saxagliptin, linagliptin, alogliptin, septagliptin and teneligliptin, GLP-1 analogues such as exenatide (also exendin-4, liraglutide, lixisenatide and taspoglutide, or SGLT inhibitors (gliflozins) such as canagliflozin, dapagliflozin and empagliflozin.

In a particularly preferred embodiment, the compounds of the present invention are administered in combination with one or more additional therapeutic agents selected from the group consisting of diuretics, angiotensin AII antagonists, ACE inhibitors, beta-receptor blockers, mineralocorticoid receptor antagonists, antidiabetics, organic nitrates and NO donors, activators and stimulators of the soluble guanylate cyclase (sGC), and positive-inotropic agents.

Thus, in a further embodiment, the present invention relates to pharmaceutical compositions comprising at least one of the compounds according to the invention and one or more additional therapeutic agents for the treatment and/or prevention of diseases, especially of the aforementioned diseases.

Furthermore, the compounds of the present invention may be utilized, as such or in compositions, in research and diagnostics, or as analytical reference standards and the like, which are well known in the art.

When the compounds of the present invention are administered as pharmaceuticals, to humans and other mammals, they can be given per se or as a pharmaceutical composition containing, for example, 0.1% to 99.5% (more preferably, 0.5% to 90%) of active ingredient in combination with one or more pharmaceutically acceptable excipients.

Thus, in another aspect, the present invention relates to pharmaceutical compositions comprising at least one of the compounds according to the invention, conventionally together with one or more inert, non-toxic, pharmaceutically suitable excipients, and to the use thereof for the treatment and/or prevention of diseases, especially of the aforementioned diseases.

The compounds according to the invention can act systemically and/or locally. For this purpose, they can be administered in a suitable way such as, for example, by the oral, parenteral, pulmonary, nasal, lingual, sublingual, buccal, rectal, dermal, transdermal, conjunctival, otic or topical route, or as an implant or stent.

For these administration routes, the compounds of the invention can be administered in suitable application forms.

Suitable for oral administration are application forms which function according to the state of the art and deliver the compounds according to the invention rapidly and/or in modified fashion, and which contain the compounds according to the invention in crystalline, amorphous and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilisates, capsules (e.g. hard or soft gelatin capsules), sugar-coated tablets, granules, pellets, powders, emulsions, suspensions, aerosols or solutions.

Parenteral application can be carried out with avoidance of an absorption step (intravenously, intra-arterially, intracardially, intraspinally or intralumbarly) or with inclusion of an absorption (intra-muscularly, subcutaneously, intracutaneously, percutaneously or intraperitoneally). Suitable parenteral application forms include injection and infusion preparations in the form of solutions, suspensions, emulsions, lyophilisates and sterile powders.

Forms suitable for other application routes include, for example, inhalatory pharmaceutical forms (e.g. powder inhalers, nebulizers), nasal drops, solutions or sprays, tablets or capsules to be administered lingually, sublingually or buccally (e.g. troches, lozenges), suppositories, ear and eye preparations (e.g. drops, ointments), vaginal capsules, aqueous suspensions (lotions, shaking mixtures), lipophilic suspensions, ointments, creams, milks, pastes, foams, dusting powders, transdermal therapeutic systems (e.g. patches), implants and stents.

In a preferred embodiment, the pharmaceutical composition comprising a compound of formula (I) as defined above is provided in a form suitable for oral administration. In another preferred embodiment, the pharmaceutical composition comprising a compound of formula (I) as defined above is provided in a form suitable for intravenous administration.

The compounds according to the invention can be converted into the recited application forms in a manner known per se by mixing with inert, non-toxic, pharmaceutically suitable excipients. These excipients include, inter alia, carriers (e.g. microcrystalline cellulose, lactose, mannitol), solvents (e.g. liquid polyethylene glycols), emulsifiers (e.g. sodium dodecyl sulfate), surfactants (e.g. polyoxysorbitan oleate), dispersants (e.g. polyvinylpyrrolidone), synthetic and natural polymers (e.g. albumin), stabilizers (e.g. antioxidants such as, for example, ascorbic acid), colorants (e.g. inorganic pigments such as, for example, iron oxides), and flavour and/or odour masking agents.

A preferred dose of the compound of the present invention is the maximum that a patient can tolerate and not develop serious side effects. Illustratively, the compound of the present invention may be administered parenterally at a dose of about 0.001 mg/kg to about 10 mg/kg, preferably of about 0.01 mg/kg to about 1 mg/kg of body weight. In oral administration, an exemplary dose range is about 0.01 to 100 mg/kg, preferably about 0.01 to 20 mg/kg, and more preferably about 0.1 to 10 mg/kg of body weight. Ranges intermediate to the above-recited values are also intended to be part of the invention.

Nevertheless, actual dosage levels and time course of administration of the active ingredients in the pharmaceutical compositions of the invention may be varied so as to obtain an amount of the active ingredient which is effective to achieve the desired therapeutic response for a particular patient, composition and mode of administration, without being toxic to the patient. It may therefore be necessary where appropriate to deviate from the stated amounts, in particular as a function of age, gender, body weight, diet and general health status of the patient, the bioavailability and pharmacodynamic characteristics of the particular compound and its mode and route of administration, the time or interval over which administration takes place, the dose regimen selected, the response of the individual patient to the active ingredient, the specific disease involved, the degree of or the involvement or severity of the disease, the kind of concurrent treatment (i.e., the interaction of the compound of the invention with other co-administered therapeutics), and other relevant circumstances.

Thus, it may be satisfactory in some cases to manage with less than the aforementioned minimum amount, whereas in other cases the stated upper limit must be exceeded. Treatment can be initiated with smaller dosages, which are less than the optimum dose of the compound. Thereafter, the dosage may be increased by small increments until the optimum effect under the circumstances is reached. For convenience, the total daily dosage may be divided and administered in individual portions spread over the day.

The following exemplary embodiments illustrate the invention. The invention is not restricted to the examples.

The percentages in the following tests and examples are, unless stated otherwise, by weight; parts are by weight. Solvent ratios, dilution ratios and concentrations reported for liquid/liquid solutions are each based on volume.

EXPERIMENTAL SECTION

The $^1$H-NMR data of selected compounds are listed in the form of $^1$H-NMR peaklists. Therein, for each signal peak the δ value in ppm is given, followed by the signal intensity, reported in round brackets. The δ value-signal intensity pairs from different peaks are separated by commas. Therefore, a peaklist is described by the general form: $δ_1$ (intensity$_1$), $δ_2$ (intensity$_2$), . . . , $δ_i$ (intensity$_1$), . . . , $δ_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of the particular target compound, peaks of impurities, $^{13}$C satellite peaks, and/or spinning sidebands. The peaks of stereoisomers, and/or peaks of impurities are typically displayed with a lower intensity compared to the peaks of the target compound (e.g., with a purity of >90%). Such stereoisomers and/or impurities may be typical for the particular manufacturing process, and therefore their peaks may help to identify a reproduction of the manufacturing process on the basis of "by-product fingerprints". An expert who calculates the peaks of the target compound by known methods (MestReC, ACD simulation, or by use of empirically evaluated expectation values), can isolate the peaks of the target compound as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. http://www.researchdisclosure.com/searching-disclosures, Research Disclosure Database Number 605005, 2014, 1 Aug. 2014). In the peak picking routine, as described in the Research Disclosure Database Number 605005, the parameter "MinimumHeight" can be adjusted between 1% and 4%. However, depending on the chemical structure and/or depending on the concentration of the measured compound it may be reasonable to set the parameter "MinimumHeight"<1%.

Chemical names were generated using the ACD/Name software from ACD/Labs. In some cases generally accepted names of commercially available reagents were used in place of ACD/Name generated names.

The following table 1 lists the abbreviations used in this paragraph and in the Examples section as far as they are not explained within the text body. Other abbreviations have their meanings customary per se to the skilled person.

TABLE 1

Abbreviations
The following table lists the abbreviations used herein.

| Abbreviation | Meaning |
| --- | --- |
| br | broad ($^1$H-NMR signal) |
| CI | chemical ionisation |
| d | doublet |
| DAD | diode array detector |
| DCM | dichloromethane |
| dd | double-doublet |
| d.e. | diastereomeric excess |
| DIPEA | N,N-diisopropylethylamine |
| DMF | N,N-dimethylformamide |
| DMAP | 4-Dimethylaminopyridine |
| DMSO | dimethylsulfoxide |
| dt | double-triplet |
| eq. | equivalent |
| ESI | electrospray (ES) ionisation |
| h | hour(s) |
| HPLC | high performance liquid chromatography |
| LC-MS | liquid chromatography mass spectrometry |
| min | minute(s) |
| MS | mass spectrometry |
| MTBE | methyl tert-butyl ether |
| NMR | nuclear magnetic resonance spectroscopy: chemical shifts (δ) are given in ppm. The chemical shifts were corrected by setting the DMSO signal to 2.50 ppm unless otherwise stated. |
| of th. | of theory |
| q | quartet |
| quin | quintet |
| r.t. or rt or RT | room temperature |
| $R_t$ | retention time (as measured either with HPLC or UPLC) in minutes |
| s | singlet |
| SFC | supercritical fluid chromatography |
| TBAF | tetra-n-butyl-ammonium fluoride |
| TBDMSCl | tert-butyldimethylsilylchloride |
| TBDMS | tert-butyldimethylsilyl |
| tBuOK | potassium tert-butoxide |
| td | triple-doublet |
| TFA | trifluoroacetic acid |
| TFAA | trifluoroacetic acid anhydride |
| THF | tetrahydrofuran |
| UPLC | ultra performance liquid chromatography |

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

UPLC-MS Standard Procedures

Method 1 (LC/MS):

Instrument: Waters ACQUITY SQD UPLC System; column: Waters Acquity UPLC HSS T3 1.8µ 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 208-400 nm.

Method 2 (LC/MS):

Instrument MS: Thermo Scientific FT-MS; Instrument type UHPLC+: Thermo Scientific UltiMate 3000; column: Waters, HSST3, 2.1×75 mm, C18 1.8 µm; eluent A: 1 l water+0.01% formic acid; eluent B: 1 l acetonitrile+0.01% formic acid; gradient: 0.0 min 10% B→2.5 min 95% B→3.5 min 95% B; oven: 50° C.; flow rate: 0.90 ml/min; UV detection: 210 nm/optimum integration path 210-300 nm.

Method 3 (LC/MS):

Instrument: Agilent MS Quad 6150; HPLC: Agilent 1290; column: Waters Acquity UPLC HSS T3 1.8µ 50×2.1 mm; eluent A: 1 l Water+0.25 ml 99% ige formic acid, eluent B: 1 l acetonitrile+0.25 ml 99% ige formic acid; gradient: 0.0 min 90% A→0.3 min 90% A→1.7 min 5% A→3.0 min 5% A oven: 50° C.; flow rate: 1.20 ml/min; UV detection: 205-305 nm.

Method 4 (LC/MS):

Instrument: Waters ACQUITY SQD UPLC System; column: Waters Acquity UPLC HSS T3 1.8µ 50×1 mm; eluent A: 1 l water+0.25 ml 99% formic acid, Eluent B: 1 l acetonitrile+0.25 ml 99% formic acid; gradient: 0.0 min 95% A→6.0 min 5% A→7.5 min 5% A; oven: 50° C.; flow rate: 0.35 ml/min; UV detection: 210-400 nm.

Method 5 (Preparative HPLC):

Column: Chromatorex C18 10 µm, 125 mm×30 mm; eluent A: water+0.05% TFA, eluent B: acetonitrile+0.05% TFA; gradient: 20% B→45% B, 45% B isocratic, 45% B→80% B; column temperature: room temperature; flow rate: 50 ml/min; UV detection: 210 nm.

Method 6 (LC-MS):

Instrument MS: Waters Synapt G2S; Instrument UPLC: Waters Acquity I-CLASS; column: Waters, HSST3, 2.1×50 mm, C18 1.8 µm; eluent A: 1 l water+0.01% formic acid; eluent B: 1 l acetonitrile+0.01% formic acid; gradient: 0.0 min 2% B→2.0 min 2% B→13.0 min 90% B→15.0 min 90% B; oven: 50° C.; flow rate: 1.20 ml/min; UV detection: 220-210 nm.

Method 6 (Preparative HPLC):

Column: Chromatorex C18 10 µm; 125×30 mm, Flow: 75 ml/min, detection at 210 nm, eluent A: water+0.1% formic acid, eluent B: acetonitrile+0.1% formic acid; 0-6 min 10% B; 6-27 min gradient to 95% B; 27-38 min 95% B; 38-39 min gradient to 10% B; 39-40 min 10% B.

Method 7 (Preparative HPLC):

Column: Chromatorex C18 10 µm; 125×30 mm, flow: 75 ml/min, detection at 210 nm, eluent A: water+0.1% formic acid, eluent B: methanol+0.1% formic acid; 0-7.2 min 5% B; 7.2-7.45 min gradient to 20% B; 7.45-14.5 min gradient to 40% B; 14.5-15 min gradient to 100% B; 15-24.3 min 100% B; 24.2-24.5 min gradient to 5% B; 24.5-27.3 min 5% B.

Method 8 (Preparative HPLC):

Column: Reprosil C18 10 µm; 250×40 mm, flow: 75 ml/min, detection at 210 nm, eluent A: water+0.1% formic acid, eluent B: acetonitrile+0.1% formic acid; 0-6 min 10% B; 6-27 min gradient to 95% B; 27-38 min 95% B; 38-39 min gradient to 10% B; 39-40 min 10% B.

EXPERIMENTAL SECTION—STARTING MATERIALS AND INTERMEDIATES

Example 1A

{3-(4-Chlorophenyl)-5-oxo-4-[(2S)-3,3,3-trifluoro-2-hydroxypropyl]-4,5-dihydro-1H-1,2,4-triazol-1-yl}acetonitrile

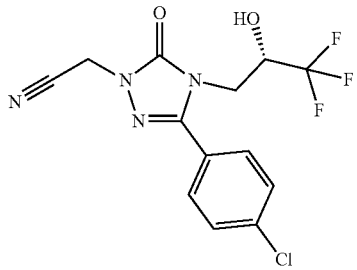 [SMILES: N#CCn1nc(-c2ccc(Cl)cc2)n(C[C@H](O)C(F)(F)F)c1=O]

In a 2 l reaction vessel, 100 g (273 mmol) of {3-(4-chlorophenyl)-5-oxo-4-[(2S)-3,3,3-trifluoro-2-hydroxypropyl]-4,5-dihydro-1H-1,2,4-triazol-1-yl}acetic acid (synthesis described as Example 8A in WO 2010/105770-A1), 43.3 g (547 mmol) of pyridine and 33 mg (0.3 mmol) of 4-dimethylaminopyridine were dissolved in 300 ml THF. The resulting solution was treated at 5° C. with 52.8 g (438 mmol) of 2,2-dimethylpropanoylchloride over 15 minutes and the resulting mixture was stirred at room temperature for 2.5 hours. After cooling to 0° C., 183 ml of 28% aqueous ammonia solution was added over 1 h while the solution temperature was kept between 10° C. and 20° C. and at the resulting mixture then stirred at 5° C. for an additional time period of 1 h. 500 ml methyl tert-butylether and 300 ml 20% aqueous citric acid were then added while keeping the internal temperature between 10° C. and 20° C. The phases were the separated and the organic phase was washed with 300 ml of 20% aqueous citric acid followed by 300 ml saturated aqueous sodium hydrogencarbonate solution and finally with 300 ml of 10% aqueous sodium chloride solution. The organic phase was evaporated at 60° C. under reduced pressure until an oily residue was obtained. 300 ml THF was then added and the solution was evaporated again until an oily solution was obtained. This operation was repeated a second time. The oil residue was retaken in 360 ml THF and treated with 172 g (820 mmol) trifluoroacetic acid anhydride over 20 min at a temperature between 10° C. and 20° C. The resulting solution was then stirred at room temperature for 1 h. 720 ml 4-methyl-2-pentanone and 650 ml 7.5% aqueous sodium hydroxide solution were added at a temperature between 10° C. and 20° C. Finally the pH-value was adjusted to pH=9.5 using 7.5% aqueous sodium hydroxide solution. After phase separation, the organic phase was washed twice with 450 ml 10% aqueous sodium chloride solution. The organic phase was evaporated at a temperature of 80° C. under reduced pressure while 1200 ml n-heptane was added. The formed suspension was cooled to 20° C. and a solid formed which was filtered off and washed with 200 ml n-heptane and then dried under reduced pressure (50° C., 30 mbar) affording 88 g (93% of th.) of {3-(4-chlorophenyl)-5-oxo-4-[(2S)-3,3,3-trifluoro-2-hydroxypropyl]-4,5-dihydro-1H-1,2,4-triazol-1-yl}acetonitrile as a solid.

$^1$H-NMR (400 MHz, DMSO-$d_6$): δ [ppm]=7.78 (d, 2H), 7.55 (d, 2H), 6.91 (d, 1H), 5.17 (s, 2H), 4.34-4.23 (m, 1H), 3.98 (dd, 1H), 3.81 (dd, 1H).

Example 2A

Methyl-2-{3-(4-chlorophenyl)-5-oxo-4-[(2S)-3,3,3-trifluor-2-hydroxypropyl]-4,5-dihydro-1H-1,2,4-triazol-1-yl}ethanimidate

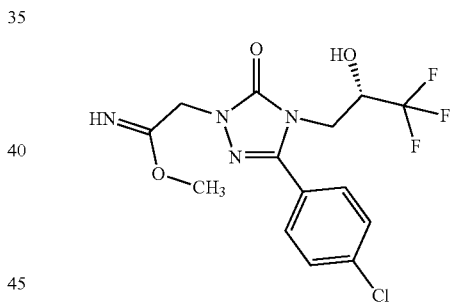

In a 4 l reaction vessel, 200 g (576.9 mmol) of {3-(4-chlorophenyl)-5-oxo-4-[(2S)-3,3,3-trifluoro-2-hydroxypropyl]-4,5-dihydro-1H-1,2,4-triazol-1-yl}acetonitrile (Example 1A) in 1600 ml methanol was treated with 5.2 g (28 mmol) sodium methanolate (30% in methanol) and the resulting mixture was stirred at 50° C. for 2.5 hours. The solution was then evaporated at 50° C. under reduced pressure until an oily solution was obtained. 2000 ml methyl tert-butylether was added and the solution was concentrated until a volume of 800 ml was achieved. 3000 ml n-heptane was then added and a suspension was formed. After cooling at 20° C., the solid was filtered and washed with 500 ml n-heptane and then dried under reduced pressure (50° C., 30 mbar) affording 175 g (80% of th.) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate as a solid.

$^1$H-NMR (400 MHz, DMSO-$d_6$): δ [ppm]=8.01 (s, 1H), 7.78 (d, 2H), 7.62 (d, 2H), 6.93 (br. s, 1H), 4.50 (s, 2H), 4.35-4.23 (m, 1H), 3.96 (dd, 1H), 3.81 (dd, 1H), 3.67 (s, 3H).

Example 3A

2-{3-(4-Chlorophenyl)-5-oxo-4-[(2S)-3,3,3-trifluoro-2-hydroxypropyl]-4,5-dihydro-1H-1,2,4-triazol-1-yl}acetohydrazide

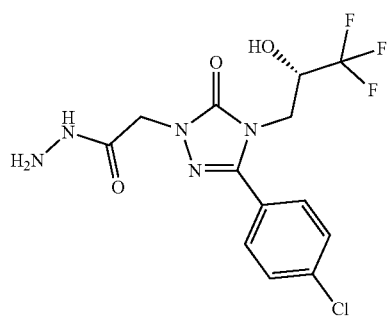 [SMILES: NNC(=O)Cn1nc(-c2ccc(Cl)cc2)n(C[C@H](O)C(F)(F)F)c1=O]

7.2 g (18.96 mmol) of methyl {3-(4-chlorophenyl)-5-oxo-4-[(2S)-3,3,3-trifluoro-2-hydroxypropyl]-4,5-dihydro-1H-1,2,4-triazol-1-yl}acetate (described as Example 7A in WO 2011/104322-A1) were dissolved in 60 ml of absolute ethanol. To this solution were added 2.088 g (41.71 mmol) of hydrazine hydrate, and the mixture was stirred under reflux for 5 h and then at room temperature overnight. The resulting mixture was partially concentrated in vacuo and then diluted with water and extracted with ethyl acetate. The combined organic phases were dried over sodium sulfate, filtered, and concentrated in vacuo. The residue was dissolved in dichloromethane, and after crystallization the solid was filtered off and dried under high vacuum. 7.02 g (18.49 mmol, 97.5% of th.) of the desired compound were obtained.

LC/MS [Method 1]: $R_t$=0.73 min; MS [ESIpos]: m/z=380 [M+H]$^+$ $^1$H NMR (400 MHz, DMSO-d$_6$): δ [ppm] 3.82 (dd, 1H), 3.96 (dd, 1H), 4.24-4.34 (m, 3H), 4.38 (d, 2H), 6.90 (d, 1H), 7.61-7.66 (m, 2H), 7.73-7.78 (m, 2H), 9.23 (t, 1H).

Example 4A 5-(4-Chlorophenyl)-2-{[5-(2-hydroxypropan-2-yl)-1H-1,2,4-triazol-3-yl]methyl}-4-[(2S)-3,3,3-trifluoro-2-hydroxypropyl]-2,4-dihydro-3H-1,2,4-triazol-3-one

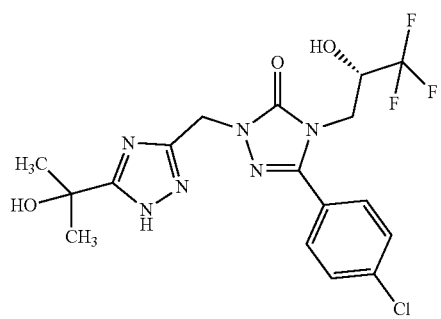 [SMILES: CC(C)(O)c1nc(Cn2nc(-c3ccc(Cl)cc3)n(C[C@H](O)C(F)(F)F)c2=O)n[nH]1]

Under argon atmosphere, sodium ethoxide (233.3 mg, 3.29 mmol, 96% purity) was added portionwise at room temperature to a solution of 2-{3-(4-chlorophenyl)-5-oxo-4-[(2S)-3,3,3-trifluoro-2-hydroxypropyl]-4,5-dihydro-1H-1,2,4-triazol-1-yl}acetohydrazide (Example 3A, 500 mg, 1.317 mmol) and 2-hydroxy-2-methylpropanimidamide hydrochloride (182.5 mg, 1.317 mmol) in DMF (13.7 ml). The reaction mixture was irradiated for 2 h at 140° C. under microwave irradiation. After cooling, the reaction mixture was partially concentrated in vacuo, then diluted with ethylacetate and washed with water. After phase separation, the aqueous phase was extracted twice with ethyl acetate. The combined organic phases were dried over sodium sulfate, filtered, and concentrated under reduced pressure. The resulting solid was dried under high vacuum to give 540 mg of the desired compound which was used without further purification.

LC/MS [Method 1]: $R_t$=0.80 min; MS [ESIpos]: m/z=447 [M+H]$^+$

Example 5A

Ethyl 1-(2-chlorophenyl)-1H-1,2,4-triazole-3-carboxylate

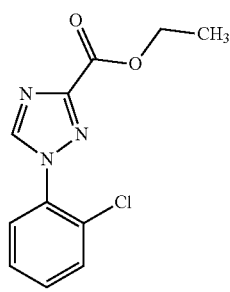 [SMILES: CCOC(=O)c1ncn(-c2ccccc2Cl)n1]

To a suspension of 2-chloroaniline (7 g, 54.9 mmol, 5.77 ml) in a mixture of water (30 ml) and concentrated hydrochloric acid (16.2 g, 164.6 mmol, 16.06 ml) at 0° C., was added dropwise a solution of sodium nitrite (3.79 g, 54.9 mmol) in water (6 ml), maintaining the temperature between 0° C. and 5° C. This reaction mixture was stirred for 5 min at 0° C. and was then added dropwise to a mixture of sodium acetate (29.3 g, 356.7 mmol) and ethyl 2-isocyanoacetate (6.207 g, 54.9 mmol, 6 ml) in a mixture of water (60 ml) and methanol (6 ml) at 0° C. The reaction mixture was stirred for 30 min at 0° C. and further stirred overnight at room temperature. The reaction mixture was then diluted with water and extracted with ethyl acetate. The combined organic phases were dried over sodium sulfate, filtered, and concentrated in vacuo. The crude product was purified by flash column chromatography (Biotage SNAP KP-Sil 340 g, 0-8 min isocratic ethylacetate/cyclohexane 70:30, 8-30 min gradient to ethylacetate/cyclohexane 45:55, 30-38 min isocratic ethylacetate/cyclohexane 45:55; flow: 100 ml/min) and 6.30 g of the desired compound (13.8 mmol, 45.6% of th.) were obtained.

LC/MS [Method 3]: $R_t$=1.06 min; MS [ESIpos]: m/z=252 [M+H]$^+$ $^1$H NMR (400 MHz, DMSO-d$_6$) δ [ppm] 1.33 (t, 3H), 4.37 (q, 2H), 7.56-7.68 (m, 2H), 7.72-7.81 (m, 2H), 9.15 (s, 1H).

Example 6A

[1-(2-Chlorophenyl)-1H-1,2,4-triazol-3-yl]methanol

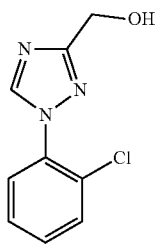 [SMILES: OCc1ncn(-c2ccccc2Cl)n1]

At 0° C. under an argon atmosphere, lithium chloride (5.22 g, 123.2 mmol) and sodium borohydride (4.66 g, 123.2 mmol) were added to a solution of ethyl 1-(2-chlorophenyl)-1H-1,2,4-triazole-3-carboxylate (Example 5A, 6.2 g, 24.63 mmol) in a mixture of tetrahydrofuran (140 ml) and ethanol (140 ml). The reaction mixture was stirred for 20 h at room temperature. The reaction mixture was diluted with ethyl acetate and then quenched with saturated aqueous ammonium chloride solution. After phase separation, the aqueous phase was extracted twice with ethylacetate. The combined organic phases were washed with brine, dried over sodium sulfate, filtered, and concentrated in vacuo.

The residue was stirred in a mixture of ethyl acetate and diethylether (1:1) with some methanol.

The resulting mixture was filtered and the filtrate concentrated in vacuo. 5.30 g of the desired compound were obtained and used without further purification.

LC/MS [Method 1]: $R_t$=0.53 min; MS [ESIpos]: m/z=210 [M+H]$^+$ $^1$H NMR (400 MHz, DMSO-d$_6$): δ [ppm] 4.53 (d, 2H), 5.39 (t, 1H), 7.54-7.66 (m, 3H), 7.71-7.76 (m, 1H), 8.88 (s, 1H).

Example 7A 3-({[Tert-butyl(dimethyl)silyl]oxy}methyl)-1-(2-chlorophenyl)-1H-1,2,4-triazole

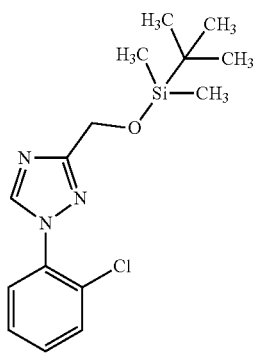 [SMILES: CC(C)(C)[Si](C)(C)OCc1ncn(-c2ccccc2Cl)n1]

To a solution of [1-(2-chlorophenyl)-1H-1,2,4-triazol-3-yl]methanol (Example 6A, 5.2 g, 24.8 mmol) in DMF were added tert-butylchlorodimethylsilane (4.67 g, 31 mmol) and imidazole (3.38 g, 49.6 mmol). The reaction mixture was stirred overnight at room temperature. The reaction mixture was diluted with ethyl acetate and then quenched with saturated aqueous sodium hydrogen carbonate. After phase separation, the aqueous phase was extracted twice with ethyl acetate. The combined organic phases were washed with brine, dried over sodium sulfate, filtered, and concentrated in vacuo. 7.6 g (23.4 mmol) of the desired compound were obtained and used without further purification.

LC/MS [Method 1]: $R_t$=1.25 min; MS [ESIpos]: m/z=324 [M+H]$^+$

Example 8A 3-({[Tert-butyl(dimethyl)silyl]oxy}methyl)-1-(2-chlorophenyl)-N-methoxy-N-methyl-1H-1,2,4-triazole-5-carboxamide

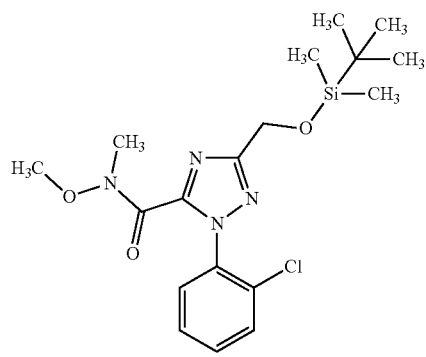 [SMILES: CON(C)C(=O)c1nc(CO[Si](C)(C)C(C)(C)C)nn1-c1ccccc1Cl]

Under argon atmosphere, n-butyl lithium (9.34 ml, 23.34 mmol, 2.5 M in hexane) was added dropwise to a solution of 3-({[tert-butyl(dimethyl)silyl]oxy}methyl)-1-(2-chlorophenyl)-1H-1,2,4-triazole (Example 7A) in tetrahydrofuran (200 ml) at −78° C. After 15 min of stirring at −78° C., N-methoxy-N-methylcarbamoyl chloride (2.64 g, 21.40 mmol) was added and the resulting mixture was stirred for 40 min at −78° C. and was then allowed to warm to room temperature. The reaction mixture was diluted with ethyl acetate and then quenched with saturated aqueous ammonium chloride. After phase separation, the aqueous phase was extracted twice with ethyl acetate. The combined organic phases were dried over sodium sulfate, filtered, and concentrated in vacuo. 8.01 g (13.06 mmol, 67% purity) of the desired compound were obtained and used without further purification.

LC/MS [Method 1]: $R_t$=1.33 min; MS [ESIpos]: m/z=411 [M+H]$^+$

Example 9A 1-(2-Chlorophenyl)-3-(hydroxymethyl)-N-methoxy-N-methyl-1H-1,2,4-triazole-5-carboxamide

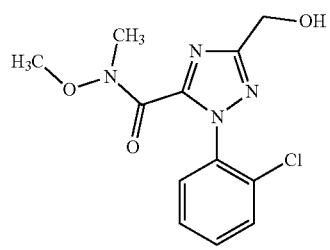 [SMILES: CON(C)C(=O)c1nc(CO)nn1-c1ccccc1Cl]

To a solution of 3-({[tert-butyl(dimethyl)silyl]oxy}methyl)-1-(2-chlorophenyl)-N-methoxy-N-methyl-1H-1,2,4-triazole-5-carboxamide (Example 8A; 8.0 g, 13.04 mmol, 67% purity) in dichloromethane (30 ml) was added trifluoroacetic acid (8 ml, 104.5 mmol) at room temperature. After stirring overnight at room temperature, additional portion of trifluoroacetic acid (5 ml) was added due to incomplete conversion. The reaction mixture was stirred for 30 min at room temperature and then concentrated in vacuo. The crude product was purified by preparative HPLC and 2.72 g of the desired compound (9.17 mmol, 70.3% of th.) were obtained.

LC/MS [method 1]: $R_t$=0.61 min; MS [ESIpos]: m/z=297 [M+H]$^+$

Example 10A 3-(Chloromethyl)-1-(2-chlorophenyl)-N-methoxy-N-methyl-1H-1,2,4-triazole-5-carboxamide

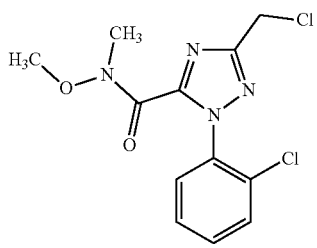 [SMILES: CON(C)C(=O)c1nc(CCl)nn1-c1ccccc1Cl]

To a solution of 1-(2-chlorophenyl)-3-(hydroxymethyl)-N-methoxy-N-methyl-1H-1,2,4-triazole-5-carboxamide (Example 9A, 2.60 g, 8.76 mmol) in dichloromethane (270 ml) was added phosphorus pentachloride (3.65 g, 17.52 mmol) at room temperature. The reaction mixture was stirred for 30 min at room temperature and then quenched with saturated aqueous sodium hydrogen carbonate. After phase separation, the aqueous phase was extracted with dichloromethane. The combined organic phases were dried over sodium sulfate, filtered, and concentrated in vacuo. 2.70 g (8.57 mmol) of the desired compound were obtained and used without further purification.

LC/MS [Method 1]: $R_t$=0.88 min; MS [ESIpos]: m/z=315 [M+H]$^+$

Example 11A 1-(2-Chlorophenyl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-N-methoxy-N-methyl-1H-1,2,4-triazole-5-carboxamide

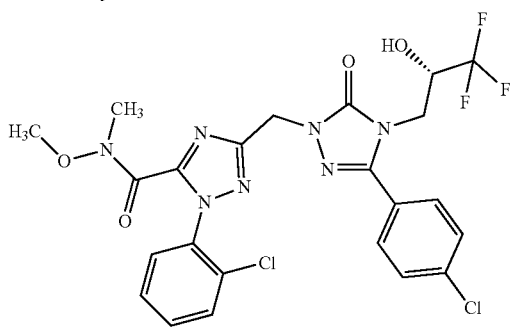

Under argon atmosphere, potassium tert-butoxide (2.255 g, 16.32 mmol) was added at room temperature to a solution of 5-(4-chlorophenyl)-4-[(2S)-3,3,3-trifluoro-2-hydroxypropyl]-2,4-dihydro-3H-1,2,4-triazol-3-one (for preparation, see Example 5A in WO 2011/104322-A1; 2.51 g, 8.16 mmol) and a catalytic amount of potassium iodide in acetonitrile (92 ml). To this solution was added 3-(chloromethyl)-1-(2-chlorophenyl)-N-methoxy-N-methyl-1H-1,2,4-triazole-5-carboxamide (Example 10 A, 2.70 g, 8.57 mmol), and the reaction mixture was stirred for 5 h at reflux. The reaction mixture was then concentrated in vacuo, diluted with ethyl acetate and water. After phase separation, the aqueous phase was extracted twice with ethyl acetate. The combined organic phases were dried over sodium sulfate, filtered, and concentrated in vacuo. The crude product was purified by preparative HPLC [Method 5] and 3.50 g of the desired compound (5.79 mmol, 97% purity, 71% of th.) were obtained.

LC/MS [Method 1]: $R_t$=1.03 min; MS [ESIpos]: m/z=586 [M+H]$^+$ $^1$H NMR (400 MHz, DMSO-d$_6$): δ [ppm] 3.16 (br. s., 2H), 3.71 (br. s., 3H), 3.85 (dd, 1H), 4.01 (dd, 1H), 4.30 (br. s., 1H), 5.14-5.25 (m, 2H), 6.89 (d, 1H), 7.49-7.66 (m, 5H), 7.69 (d, 1H), 7.75 (d, 2H).

Example 12A 5-(4-Chlorophenyl)-2-{[1-(2-chlorophenyl)-5-propionyl-1H-1,2,4-triazol-3-yl]methyl}-4-[(2S)-3,3,3-trifluoro-2-hydroxypropyl]-2,4-dihydro-3H-1,2,4-triazol-3-one

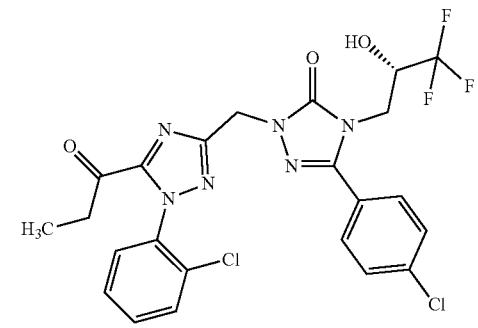 [SMILES: CCC(=O)c1nc(Cn2nc(-c3ccc(Cl)cc3)n(C[C@H](O)C(F)(F)F)c2=O)nn1-c1ccccc1Cl]

To a solution of 1-(2-chlorophenyl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-N-methoxy-N-methyl-1H-1,2,4-triazole-5-carboxamide (Example 11A, 250 mg, 0.426 mmol) in THF (7.5 ml) was added ethylmagnesium bromide (0.284 ml, 0.853 mmol, 3M solution in diethylether) at 0° C. The reaction mixture was stirred for 1 h at 0° C., then quenched with aqueous 1 N hydrochloric acid and extracted with ethyl acetate. The combined organic phases were dried over sodium sulfate, filtered, and concentrated in vacuo. The crude product was purified by preparative HPLC [Method 5] and 159.1 mg of the desired compound (0.29 mmol, 67% of th.) were obtained.

LC/MS [Method 4]: $R_t$=3.59 min; MS [ESIpos]: m/z=555 [M+H]$^+$ $^1$H NMR (400 MHz, DMSO-d$_6$): δ [ppm] 1.00 (t, 3H), 3.11 (q, 2H), 3.86 (dd, 1H), 4.01 (dd, 1H), 4.23-4.35 (m, 1H), 5.14-5.25 (m, 2H), 6.89 (d, 1H), 7.49-7.55 (m, 1H), 7.57-7.65 (m, 4H), 7.67-7.71 (m, 1H), 7.72-7.78 (m, 2H).

Example 13A 5-(4-Chlorophenyl)-2-{[1-(2-chlorophenyl)-5-isobu-tyryl-1H-1,2,4-triazol-3-yl]methyl}-4-[(2S)-3,3,3-trifluoro-2-hydroxypropyl]-2,4-dihydro-3H-1,2,4-triazol-3-one

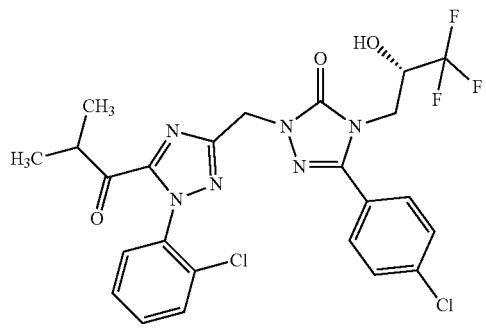 [SMILES: CC(C)C(=O)c1nc(Cn2nc(-c3ccc(Cl)cc3)n(C[C@H](O)C(F)(F)F)c2=O)nn1-c1ccccc1Cl]

To a solution of 1-(2-chlorophenyl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-N-methoxy-N-methyl-1H-1,2,4-triazole-5-carboxamide (Example 11A, 600 mg, 1.02 mmol) in THF (18 ml) was added isopropylmagnesium bromide (0.706 ml, 2.047 mmol, 2.9 M solution in 2-methyltetrahydrofuran) at 0° C. After stirring for 1 h at 0° C., extra portion of isopropylmagnesium bromide (0.706 ml, 2.047 mmol) was added portionwise over the day at 0° C., due to incomplete conversion. The reaction mixture was stirred overnight at room temperature, then quenched with aqueous 1 N hydrochloric acid and extracted with ethyl acetate. The combined organic phases were dried over sodium sulfate, filtered, and concentrated in vacuo. The crude product was purified by preparative HPLC [Method 5] and 54.2 mg of the desired compound (0.10 mmol, 9.3% of th.) were obtained.

LC/MS [Method 4]: $R_t$=3.78 min; MS [ESIpos]: m/z=569 [M+H]$^+$ $^1$H NMR (400 MHz, DMSO-d$_6$): δ [ppm] 1.11 (d, 6H), 3.64 (dt, 1H), 3.86 (dd, 1H), 4.01 (dd, 1H), 4.29 (br. s., 1H), 5.16-5.27 (m, 2H), 6.89 (d, 1H), 7.50-7.56 (m, 1H), 7.57-7.65 (m, 4H), 7.66-7.71 (m, 1H), 7.72-7.77 (m, 2H).

Example 14A 3,3,3-Trifluoro-2-hydroxypropanamide

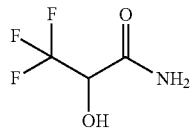

Methyl 3,3,3-trifluoro-2-hydroxypropanoate (2 g, 12.65 mmol) was diluted in a solution of ammonia in methanol (12 ml, 84 mmol, 7 N ammonia in methanol). The reaction mixture was irradiated for 3 h at 80° C. under microwave irradiation. After cooling, the reaction mixture was carefully concentrated in vacuo. The crude product was diluted with dichloromethane and carefully concentrated in vacuo (3 times). Finally, the desired compound (1.6 g, 11.2 mmol) was obtained and used without further purification.

$^1$H NMR (400 MHz, DMSO-d$_6$): δ [ppm] 4.36-4.48 (m, 1H), 6.97 (d, 1H), 7.60 (br. s., 2H).

Example 15A 3,3,3-Trifluoro-2-hydroxypropanimidamide hydrochloride

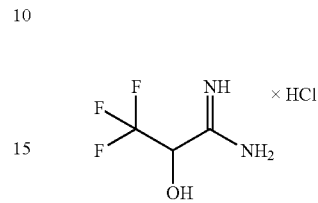

To a solution of 3,3,3-trifluoro-2-hydroxypropanamide (Example 14 A, 1.6 g, 11.184 mmol) in THF (8 ml) was added triethyloxonium tetrafluoroborate (2.34 g, 12.30 mmol) at room temperature. The resulting mixture was carefully kept at room temperature and stirred for 4 h. The resulting mixture was concentrated in vacuo, then diluted with methanol (5 ml) and cooled to 0° C. To the reaction mixture was added a solution of ammonia in methanol (7.32 ml, 51.29 mmol, 7 N ammonia in methanol) at 0° C. Once the reaction mixture had warmed to room temperature, it was concentrated in vacuo and then diluted with ethyl acetate. The resulting solution was cooled to 0° C. and after addition of a solution of hydrochloric acid in dioxane (4.89 ml, 19.54 mmol, 4 M hydrochloric acid in dioxane) at 0° C.; the reaction mixture was stirred overnight at room temperature. The reaction mixture was then diluted with MTBE and partially concentrated in vacuo. After crystallisation, the solid was filtered off and dried under high vacuum. 500 mg (2.80 mmol, 25% of th.) of the desired compound were obtained.

$^1$H NMR (400 MHz, DMSO-d$_6$): δ [ppm] 5.12 (quin, 1H), 8.11 (d, 1H), 9.32 (br. d, 4H).

Example 16A 5-(4-Chlorophenyl)-2-{[5-(2,2,2-trifluoro-1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one

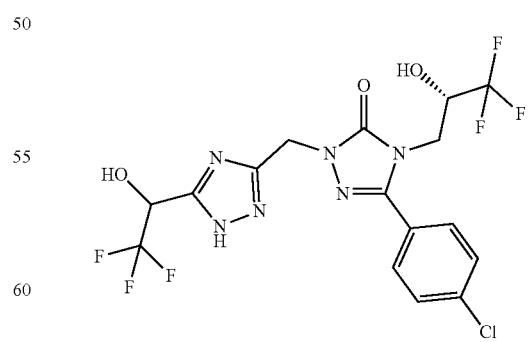

Under argon atmosphere, sodium ethoxide (238.2 mg, 3.36 mmol, 96% purity) was added portionwise at room temperature to a solution of 2-{3-(4-chlorophenyl)-5-oxo-4-[(2S)-3,3,3-trifluoro-2-hydroxypropyl]-4,5-dihydro-1H-1, 2,4-triazol-1-yl}acetohydrazide (Example 3A, 1.063 g, 2.24 mmol, 80% purity) and 3,3,3-trifluoro-2-hydroxypropanimidamide hydrochloride (Example 15 A, 400 mg, 2.24 mmol) in DMF (23 ml). The reaction mixture was stirred at 100° C. overnight. After cooling, the reaction mixture was diluted with MTBE and then quenched with aqueous hydrochloric acid (1M). After phase separation, the aqueous phase was extracted twice with MTBE and the combined organic phases were dried over sodium sulfate, filtered, and concentrated under reduced pressure. The crude product was purified by preparative HPLC [Method 5] and the desired compound (192 mg, 0.39 mmol, 17.6% of th.) was obtained.

LC/MS [Method 1]: $R_t$=0.85 min; MS [ESIpos]: m/z=487 [M+H]$^+$

Example 17A 5-(4-Chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (diastereomeric mixture)

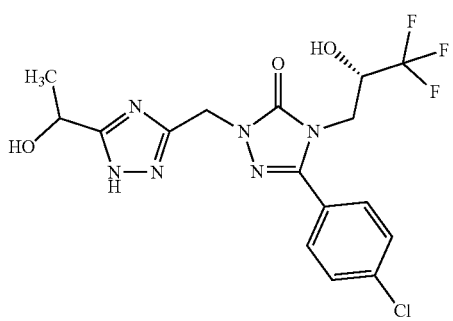 [SMILES: CC(O)c1nc(Cn2nc(-c3ccc(Cl)cc3)n(C[C@H](O)C(F)(F)F)c2=O)n[nH]1]

Under argon atmosphere, sodium ethoxide (1.531 g, 21.59 mmol, 96% purity) was added portionwise at room temperature to a solution of 2-{3-(4-chlorophenyl)-5-oxo-4-[(2S)-3,3,3-trifluoro-2-hydroxypropyl]-4,5-dihydro-1H-1,2,4-triazol-1-yl}acetohydrazide (Example 3A; 4.1 g, 10.80 mmol) and 2-hydroxypropanimidamide hydrochloride (1.480 g, 11.88 mmol) in DMF (110 ml). The reaction mixture was stirred at 120° C. for 4.5 h. Ater cooling, the reaction mixture was partially concentrated in vacuo and then diluted with ethyl acetate. The resulting mixture was washed with water, and after phase separation, the aqueous phase was extracted twice with ethyl acetate. The combined organic phases were dried over sodium sulfate, filtered, and concentrated under reduced pressure. The resulting solid was dried under high vacuum to give 4.90 g (92% purity, 10.42 mmol) of the desired compound as a mixture of diastereomers which was used without further purification.

LC/MS [Method 1]: $R_t$=0.82 min; MS [ESIpos]: m/z=433 [M+H]$^+$ $^1$H NMR (400 MHz, DMSO-d$_6$): δ [ppm] 1.39 (d, 3H), 3.79-3.88 (m, 1H), 3.93-4.02 (m, 1H), 4.24-4.36 (m, 1H), 4.80 (quin, 1H), 4.89-5.00 (m, 2H), 5.73 (m, 1H), 6.93 (d, 1H), 7.58-7.65 (m, 2H), 7.70-7.77 (d, 2H), 13.68 (s, 1H).

Example 18A 5-(4-Chlorophenyl)-2-({1-(2-chlorophenyl)-5-[(1RS)-1-hydroxyethyl]-1H-1,2,4-triazol-3-yl}-methyl)-4-[(2S)-3,3,3-trifluoro-2-hydroxypropyl]-2,4-dihydro-3H-1,2,4-triazol-3-one (diastereomeric mixture)

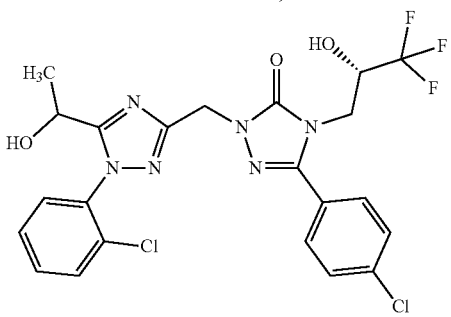

To a solution of 5-(4-chlorophenyl)-2-(({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (Example 17A; 2.10 g, 3.88 mmol, 80% purity) in pyridine (50 ml) were added (2-chlorophenyl)boronic acid (1.214 g, 7.76 mmol) and copper(II) acetate (1.410 g, 7.76 mmol). The reaction mixture was heated to 60° C. for 1 h and then stirred at room temperature for 5 days, after which extra boronic acid (303 mg, 1.94 mmol) was added due to incomplete conversion. After stirring at room temperature for two additional days, the resulting reaction mixture was concentrated in vacuo, then diluted with MTBE and quenched with aqueous hydrochloric acid (0.5 M). After phase separation, the aqueous phase was extracted twice with MTBE. The combined organic phases were dried over sodium sulfate, filtered, and concentrated in vacuo. The crude product was purified by preparative HPLC [method 5], and the desired compound (580 mg, 1.01 mmol, 95% purity, 26.1% of th.) was obtained as a mixture of diastereomers.

LC/MS [method 3]: $R_t$=1.24 min; MS [ESIpos]: m/z=543 [M+H]$^+$ $^1$H NMR (400 MHz, DMSO-d$_6$): δ [ppm] 1.38 (d, 3H), 3.85 (dd, 1H), 4.00 (dd, 1H), 4.30 (br. s, 1H), 4.55-4.64 (m, 1H), 5.01-5.13 (m, 2H), 6.85-6.94 (m, 1H), 7.50-7.65 (m, 5H), 7.67-7.78 (m, 3H).

The two diastereomers were separated by preparative chiral HPLC (SFC) [sample preparation: 575 mg dissolved in 35 ml methanol; injection volume: 0.4 ml; column: Daicel Chiralcel® OX-H 5 μm, 250×20 mm; eluent: carbon dioxide/methanol 70:30; flow rate: 80 ml/min; temperature: 40° C.; UV detection: 210 nm]. After separation, 206 mg of diastereomer 1 (Example 19A), which eluted first, and 189 mg of diastereomer 2 (Example 20A), which eluted later, were isolated.

Example 19A 5-(4-Chlorophenyl)-2-{[1-(2-chlorophenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 1)

LC/MS [method 3]: $R_t$=1.24 min; MS [ESIpos]: m/z=543 [M+H]$^+$

Analytical chiral HPLC: $R_t$=8.34 min, d.e.=100% [column: LUX Cellulose-4, 5 μm, 250×4.6 mm; eluent: isohexane/ethanol 70:30; flow rate: 1 ml/min; temperature: 40° C.; UV detection: 220 nm].

$^1$H NMR (400 MHz, DMSO-d$_6$): δ [ppm] 1.38 (d, 3H), 3.85 (dd, 1H), 4.00 (dd, 1H), 4.30 (br. s, 1H), 4.59 (q, 1H), 5.01-5.13 (m, 2H), 5.50 (br. s, 1H), 6.90 (d, 1H), 7.50-7.65 (m, 5H), 7.67-7.78 (m, 3H).

Example 20A 5-(4-Chlorophenyl)-2-{[1-(2-chlorophenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 2)

Analytical chiral HPLC: R$_t$=11.88 min, d.e.=98.1% [column: LUX Cellulose-4, 5 μm, 250×4.6 mm; eluent: isohexane/ethanol 70:30; flow rate: 1 ml/min; temperature: 40° C.; UV detection: 220 nm].

$^1$H NMR (400 MHz, DMSO-d$_6$): δ [ppm] 1.38 (d, 3H), 3.85 (dd, 1H), 4.00 (dd, 1H), 4.24-4.36 (m, 1H), 4.54-4.65 (m, 1H), 5.07 (s, 2H), 5.51 (br. s, 1H), 6.90 (d, 1H), 7.50-7.65 (m, 5H), 7.68-7.79 (m, 3H).

Example 21A

2-{[5-Acetyl-1-(2-chlorophenyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one

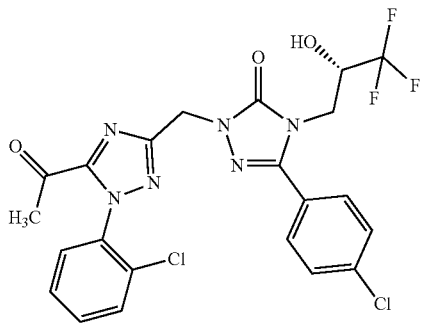 [SMILES: CC(=O)c1nc(Cn2nc(-c3ccc(Cl)cc3)n(C[C@H](O)C(F)(F)F)c2=O)nn1-c1ccccc1Cl]

To a solution of 5-(4-chlorophenyl)-2-{[1-(2-chlorophenyl)-5-(1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 2, Example 20A, 560 mg, 1.031 mmol) in dichloroethane (34 ml) was added manganese(IV) oxide (358.4 mg, 4.123 mmol) at room temperature. The reaction mixture was stirred for 5 h at 60° C. After overnight stirring at room temperature, extra portion of manganese(IV) oxide (358.4 mg, 4.12 mmol) was added, due to incomplete conversion. The reaction mixture was stirred for 9 h at 60° C. and then filtered through celite. After washing the celite with a mixture of dichloromethane and methanol, the combined organic phases were dried over sodium sulfate, filtered, and concentrated in vacuo. The crude product was first purified by preparative HPLC [Method 5]. A second purification by preparative chiral HPLC SFC [sample preparation: 450 mg dissolved in a mixture (20 ml) of ethanol, methanol and acetonitrile; injection volume: 0.3 ml; column: Daicel Chiralcel® OX-H 5 μm, 250×20 mm; eluent: carbon dioxide/methanol 85:15; flow rate: 90 ml/min; temperature: 40° C.; UV detection: 210 nm] gave 320 mg (0.59 mmol, 56.7% of th.) of the desired compound.

LC/MS [Method 6]: R$_t$=7.89 min; MS [ESIpos]: m/z=541 [M+H]$^+$ $^1$H NMR (400 MHz, DMSO-d$_6$): δ [ppm] 2.61 (s, 3H), 3.86 (dd, 1H), 4.01 (dd, 1H), 4.24-4.36 (m, 1H), 5.15-5.24 (m, 2H), 6.89 (d, 1H), 7.48-7.54 (m, 1H), 7.56-7.65 (m, 4H), 7.67-7.71 (m, 1H), 7.72-7.78 (m, 2H).

Example 22A

Methyl [1-(2-chlorophenyl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-5-yl] acetate

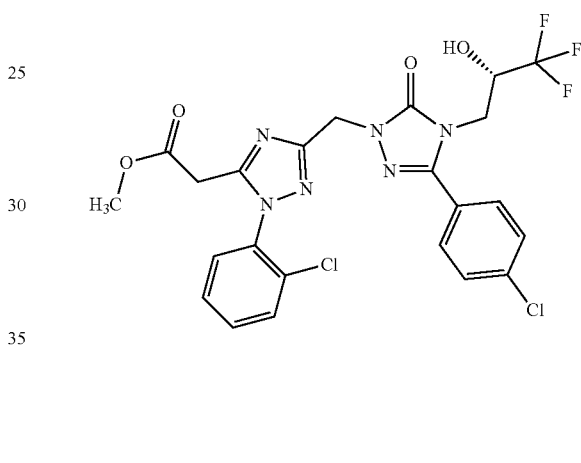

To a suspension of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (Example 2A, 4.00 g, 10.6 mmol) in dioxane (110 ml) at room temperature were added successively pyridine (1.8 ml; 23 mmol) and methyl 3-chloro-3-oxopropanoate (1.2 ml, 12 mmol). After stirring for 10 min at room temperature, (2-chlorophenyl)hydrazine hydrochloride (1:1) (2.08 g, 11.6 mmol) was added and the resulting mixture was heated to 100° C. for 4 h. The volatiles were removed at a rotary evaporator. The residue was dissolved in ethyl acetate. This organic phase was washed twice with hydrochloric acid 1M, then with a saturated aqueous solution of sodium bicarbonate and with brine, dried over sodium sulfate and evaporated at a rotary evaporator. The residue was dried in high vacuum, giving the title compound (2.26 g; 97% purity; 36% of th.).

LC-MS (Method 2): R$_t$=1.89 min; MS(ESIpos): m/z=571 [M+H]$^+$ $^1$H-NMR (400 MHz, DMSO-d6): δ [ppm]=3.49 (s, 3H), 3.80-3.90 (m, 3H), 3.97-4.04 (m, 1H), 4.22-4.38 (m, 1H), 5.08 (s, 2H), 6.90 (d, 1H), 7.52-7.66 (m, 5H), 7.71-7.79 (m, 3H).

Example 23A

Methyl [3-({4-[(2S)-2-{[tert-butyl(dimethyl)silyl]oxy}-3,3,3-trifluoropropyl]-3-(4-chlorophenyl)-5-oxo-4,5-dihydro-1H-1,2,4-triazol-1-yl}methyl)-1-(2-chlorophenyl)-1H-1,2,4-triazol-5-yl]acetate

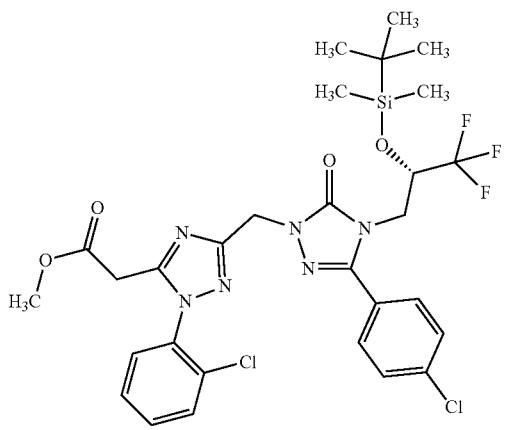 [SMILES: COC(=O)Cc1nc(Cn2nc(-c3ccc(Cl)cc3)n(C[C@H](O[Si](C)(C)C(C)(C)C)C(F)(F)F)c2=O)nn1-c1ccccc1Cl]

1H-Imidazole (387 mg; 5.69 mmol) and 4-dimethylaminopyridine (DMAP; 21.4 mg; 0.18 mmol) were added to a solution of methyl [1-(2-chlorophenyl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-5-yl]acetate (Example 22A, 1.00 g; 1.75 mmol) in dichloromethane (18 ml). A 1 M solution of tert-butyl(chloro)dimethylsilane in dichloromethane (5.43 ml; 5.43 mmol) was added and the reaction mixture was stirred overnight at room temperature. More DMAP (0.1 eq.) was added and, after further 24 h more imidazole (1.5 eq.) and tert-butyl(chloro)dimethylsilane (1.5 eq.) were added. The mixture was stirred for 8 days, then diluted with ethyl acetate and with a saturated aqueous ammonium chloride solution. The organic phase was separated, washed with a saturated aqueous sodium bicarbonate solution and with brine, dried over sodium sulfate and evaporated. The residue showed in analytical HPLC about 56% product and 44% starting material. This residue was dissolved in dichloromethane (13 ml) and submitted again to the same reaction conditions with 1H-imidazole (273 mg, 4.00 mmol), DMAP (15.1 mg; 123 µmol) and tert-butyl(chloro)dimethylsilane (3.8 ml, 1.0 M, 3.8 mmol) for 3 days. The resulting suspension was filtered and the filtrate concentrated at a rotary evaporator. The residue was diluted in a few ml DMSO and separated via preparative HPLC (Method 8) to give the title compound (927 mg; 69% of th.) as well as recovered starting material (196 mg; 19.6% of th.).

LC-MS (Method 2): $R_t$=2.70 min; MS(ESIpos): m/z=685 [M+H]$^+$ $^1$H-NMR (400 MHz, DMSO-d6): δ [ppm]=−0.23 (s, 3H), −0.03 (s, 3H), 0.71 (s, 9H), 3.50 (s, 3H), 3.83 (s, 2H), 3.96 (dd, 1H), 4.09 (dd, 1H), 4.52-4.64 (m, 1H), 5.03-5.15 (m, 2H), 7.51-7.67 (m, 5H), 7.70-7.77 (m, 3H).

Example 24A

2-[3-({4-[(2S)-2-{[Tert-butyl(dimethyl)silyl]oxy}-3,3,3-trifluoropropyl]-3-(4-chlorophenyl)-5-oxo-4,5-dihydro-1H-1,2,4-triazol-1-yl}methyl)-1-(2-chlorophenyl)-1H-1,2,4-triazol-5-yl]-2-hydroxypropanoic acid (Diastereomeric mixture)

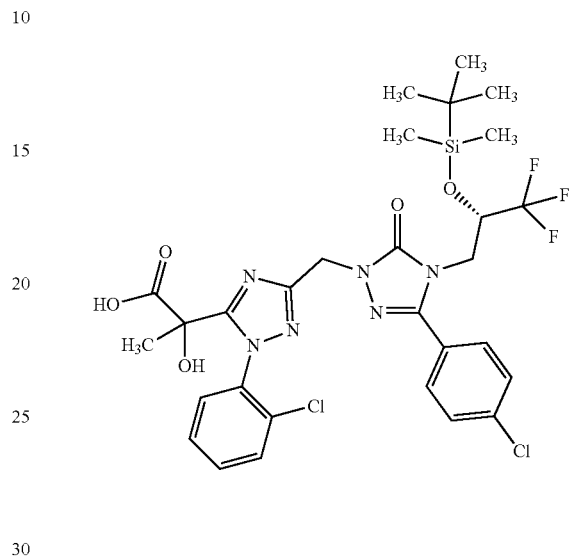

Methyl [3-({4-[(2S)-2-{[tert-butyl(dimethyl)silyl]oxy}-3,3,3-trifluoropropyl]-3-(4-chlorophenyl)-5-oxo-4,5-dihydro-1H-1,2,4-triazol-1-yl}methyl)-1-(2-chlorophenyl)-1H-1,2,4-triazol-5-yl]acetate (Example 23A; 724 mg; 1.06 mmol) was dissolved in THF (14 ml) under argon atmosphere and the solution cooled to 0° C. Sodium hydride (60% in mineral oil; 63 mg; 1.58 mmol) was added, the mixture was stirred for 30 min before methyliodide (99 µl; 1.6 mmol) was added. After 2 h at 0° C., additional sodium hydride (13 mg; 0.3 eq) was added, then after 10 min additional methyl iodide (20 µl; 0.3 eq). The mixture was stirred overnight at room temperature while allowing air to enter the vessel. The reaction was quenched with 10 ml of an ammonium chloride solution (10% in water) and diluted with ethylacetate. The organic phase was washed twice with an ammonium chloride solution, then with brine, dried over sodium sulfate and concentrated at a rotary evaporator. The residue was separated via preparative HPLC (method 6). Beside the expected products of mono- and dimethylation in the position alpha to the ester carbonyl group, the title compound was obtained (190 mg; 26% of th.).

LC-MS [Method 1]: $R_t$=1.29 min; MS(ESIpos): m/z=701 [M+H]$^+$

In a previous experiment on small scale (similar conditions but with 100 mg starting material), the same product was obtained, for which an NMR was measured:

$^1$H-NMR (400 MHz, DMSO-d$_6$): δ [ppm]=−0.26 (s, 3H), −0.04 (s, 3H), 0.70 (s, 9H), 1.66 (br. s, 3H), 3.90-3.99 (m, 1H), 4.03-4.11 (m, 1H), 4.53-4.63 (m, 1H), 5.01-5.13 (m, 2H), 5.92-6.02 (m, 1H), 7.40-7.47 (m, 2H), 7.49-7.56 (m, 1H), 7.58-7.66 (m, 3H), 7.70-7.76 (m, 2H), 13.10 (br. s, 1H).

Example 25A

Methyl [3-({3-(4-chlorophenyl)-5-oxo-4-[(2S)-3,3,3-trifluoro-2-hydroxypropyl]-4,5-dihydro-1H-1,2,4-triazol-1-yl}methyl)-1-(3-chloropyridin-2-yl)-1H-1,2,4-triazol-5-yl]acetate

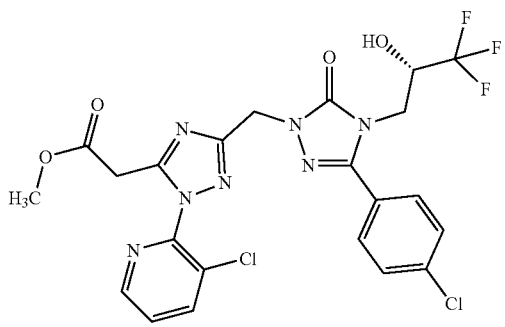 [SMILES: COC(=O)Cc1nc(Cn2nc(-c3ccc(Cl)cc3)n(C[C@H](O)C(F)(F)F)c2=O)nn1-c1ncccc1Cl]

To a suspension of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (Example 2A; 2.00 g, 5.28 mmol) in dioxane (53 ml) at room temperature were added successively pyridine (470 µl; 5.8 mmol) and methyl 3-chloro-3-oxopropanoate (620 µl, 5.8 mmol). After stirring for 10 min at room temperature, 3-chloro-2-hydrazinylpyridine (834 mg, 5.81 mmol) was added and the resulting mixture was heated to 100° C. for 2 h. The volatiles were removed at a rotary evaporator. The residue was dissolved in ethyl acetate. This organic phase was washed twice with hydrochloric acid 1 M, then with a saturated aqueous solution of sodium bicarbonate and with brine, dried over sodium sulfate and evaporated at a rotary evaporator. The residue crystallized partly at room temperature. It was suspended in acetonitrile (15 ml) and shuttled 10 sec in a sonication bath. The solid (side product) was removed by filtration and washed with little acetonitrile. The combined filtrates were concentrated in vacuo. The residue was dissolved in dichloromethane and purified via chromatography on silicagel (50 g) using ethylacetate as eluent to give the title compound in 94% purity (600 mg; 19% of th.).

LC-MS [Method 2]: $R_t$=1.79 min; MS(ESIpos): m/z=572 [M+H]$^+$ $^1$H-NMR (400 MHz, DMSO-d6): δ [ppm]: –0.008 (1.63), 0.008 (1.69), 1.157 (1.56), 1.175 (3.15), 1.192 (1.59), 1.988 (5.96), 3.287 (1.12), 3.488 (16.00), 3.814 (0.67), 3.838 (0.75), 3.851 (0.97), 3.874 (1.05), 3.978 (0.97), 3.987 (1.10), 4.015 (1.20), 4.024 (9.38), 4.038 (1.57), 5.105 (5.84), 6.898 (1.95), 6.914 (1.97), 7.610 (3.45), 7.615 (1.31), 7.626 (1.47), 7.631 (4.73), 7.665 (1.54), 7.676 (1.57), 7.685 (1.74), 7.697 (1.67), 7.742 (4.67), 7.747 (1.49), 7.759 (1.23), 7.764 (3.38), 8.283 (1.61), 8.287 (1.74), 8.303 (1.54), 8.307 (1.60), 8.543 (1.66), 8.547 (1.70), 8.555 (1.65), 8.559 (1.61).

Example 26A

Methyl [3-({4-[(2S)-2-{[tert-butyl(dimethyl)silyl]oxy}-3,3,3-trifluoropropyl]-3-(4-chlorophenyl)-5-oxo-4,5-dihydro-1H-1,2,4-triazol-1-yl}methyl)-1-(3-chloropyridin-2-yl)-1H-1,2,4-triazol-5-yl]acetate

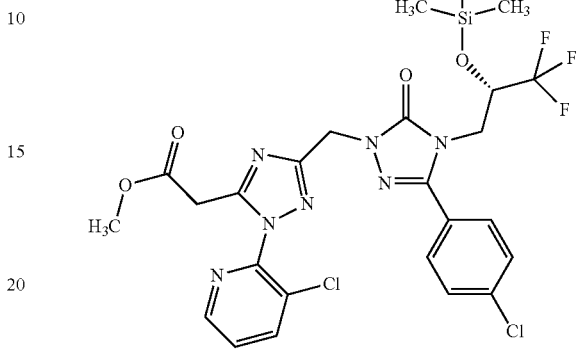

1H-Imidazole (184 mg; 2.70 mmol) and 4-dimethylaminopyridine (DMAP; 10.2 mg; 0.08 mmol) were added to a solution of methyl [3-({3-(4-chlorophenyl)-5-oxo-4-[(2S)-3,3,3-trifluoro-2-hydroxypropyl]-4,5-dihydro-1H-1,2,4-triazol-1-yl}methyl)-1-(3-chloropyridin-2-yl)-1H-1,2,4-triazol-5-yl]acetate (Example 25A; 476 mg; 0.83 mmol) in dichloromethane (8.6 ml). A 1 M solution of tert-butyl (chloro)dimethylsilane in dichloromethane (2.6 ml; 2.6 mmol) was added and the reaction mixture was stirred 4 days at room temperature. The resulting suspension was filtered and the filtrate concentrated at a rotary evaporator. The residue was diluted in a few ml DMSO and separated via preparative HPLC (Method 8) to give the title compound (370 mg; 65% of th.) as well as recovered starting material (102 mg; 21% of th.).

LC-MS [Method 2]: $R_t$=2.62 min; MS(ESIpos): m/z=686 [M+H]$^+$ $^1$H-NMR (400 MHz, DMSO-d$_6$): δ [ppm]=–0.24 (s, 3H), –0.02 (s, 3H), 0.71 (s, 9H), 3.48 (s, 3H), 3.91-3.99 (m, 1H), 4.00 (s, 2H), 4.05-4.13 (m, 1H), 4.52-4.65 (m, 1H), 5.04-5.16 (m, 2H), 7.61-7.66 (m, 2H), 7.66-7.70 (m, 1H), 7.71-7.76 (m, 2H), 8.29 (dd, 1H), 8.55 (dd, 1H).

Example 27A

2-[3-({4-[(2S)-2-{([Tert-butyl(dimethyl)silyl]oxy}-3,3,3-trifluoropropyl]-3-(4-chlorophenyl)-5-oxo-4,5-dihydro-1H-1,2,4-triazol-1-yl}methyl)-1-(3-chloropyridin-2-yl)-1H-1,2,4-triazol-5-yl]-2-hydroxypropanoic acid (diastereomeric mixture)

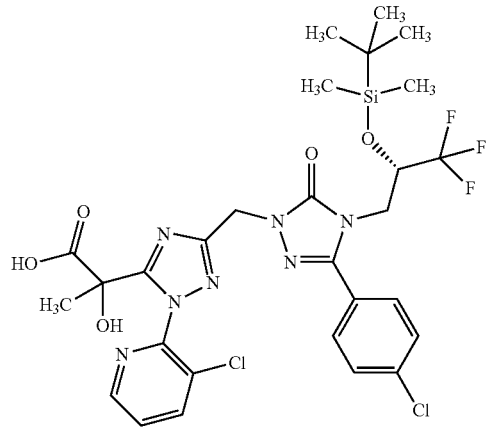 [SMILES: CC(O)(C(=O)O)c1nc(Cn2nc(-c3ccc(Cl)cc3)n(C[C@H](O[Si](C)(C)C(C)(C)C)C(F)(F)F)c2=O)nn1-c1ncccc1Cl]

Methyl [3-({4-[(2S)-2-{[tert-butyl(dimethyl)silyl]oxy}-3,3,3-trifluoropropyl]-3-(4-chlorophenyl)-5-oxo-4,5-dihydro-1H-1,2,4-triazol-1-yl}methyl)-1-(3-chloropyridin-2-yl)-1H-1,2,4-triazol-5-yl]acetate (Example 26A; 370 mg, 539 µmol) was dissolved in tetrahydrofuran (7.4 ml) under argon atmosphere. Sodium hydride (60% in mineral oil; 32 mg; 808 µmol) was added, the mixture was stirred for 30 min before methyliodide (10 µl, 160 µmol) was added. The reaction mixture was stirred 2 h at 0° C., then 3 days at room temperature while allowing air the enter the vessel. The reaction was quenched with 10 ml of an ammonium chloride solution (10% in water) then evaporated to dryness at a rotary evaporator. The residue was redissolved in some acetonitrile and DMSO, then submitted to preparative HPLC (Method 6). Beside the expected product of dimethylation in the position alpha to the ester carbonyl group, the title compound was obtained (82 mg; 22% of th.).

LC-MS [Method 2]: $R_t$=2.52 min; MS(ESIpos): m/z=702 [M+H]$^+$ $^1$H-NMR (400 MHz, DMSO-d$_6$): δ [ppm]=−0.25 (s, 3H), −0.03 (d, 3H), 0.71 (d, 9H), 1.70 (s, 3H), 3.90-4.01 (m, 1H), 4.04-4.12 (m, 1H), 4.52-4.63 (m, 1H), 5.01-5.17 (m, 2H), 5.76-5.87 (m, 1H), 7.63 (d, 3H), 7.70-7.76 (m, 2H), 8.16-8.21 (m, 1H), 8.39-8.46 (m, 1H), 13.04 (br. s, 1H). The observed doublets at −0.03 ppm and 0.71 ppm were interpreted each as a set of two singlets, one for each diastereomer of the mixture.

The structure was confirmed with NMR-2D correlation experiments.

Experimental Section—Examples

Example 1

5-(4-Chlorophenyl)-2-{[1-(3-fluorophenyl)-5-(2-hydroxypropan-2-yl)-1H-1,2,4-triazol-3-yl]methyl}-4-[(2S)-3,3,3-trifluoro-2-hydroxypropyl]-2,4-dihydro-3H-1,2,4-triazol-3-one

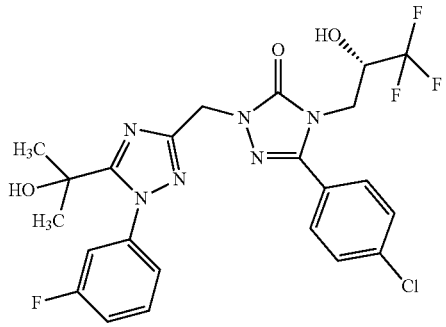 [SMILES: CC(C)(O)c1nc(Cn2nc(-c3ccc(Cl)cc3)n(C[C@H](O)C(F)(F)F)c2=O)nn1-c1cccc(F)c1]

To a solution of 5-(4-chlorophenyl)-2-{[5-(2-hydroxypropan-2-yl)-1H-1,2,4-triazol-3-yl]methyl}-4-[(2S)-3,3,3-trifluoro-2-hydroxypropyl]-2,4-dihydro-3H-1,2,4-triazol-3-one (Example 4A; 150 mg, 0.34 mmol) in pyridine (4.2 ml) were added (3-fluorophenyl)boronic acid (93.95 mg, 0.671 mmol) and copper(II) acetate (121.9 mg, 0.671 mmol). The reaction mixture was stirred for 5 days at room temperature, after which extra boronic acid (23.5 mg, 0.168 mmol) was added due to incomplete conversion. After 2 additional days of stirring, the reaction mixture was concentrated in vacuo, then diluted with MTBE and quenched with aqueous hydrochloric acid (0.5 M). After phase separation, the aqueous phase was extracted twice with MTBE. The combined organic phases were dried over sodium sulfate, filtered, and concentrated in vacuo. The crude product was first purified by preparative HPLC [Method 5]. A second purification by preparative chiral HPLC [sample preparation: 85 mg dissolved in 2 ml isopropanol; injection volume: 0.7 ml; column: Daicel Chiralcel® OX-H 5 µm, 250×20 mm; eluent: isohexane/isopropanol 60:40; flow rate: 15 ml/min; temperature: 30° C.; UV detection: 220 nm] gave 48 mg (0.09 mmol, 26.4% of th.) of the desired compound.

LC/MS [Method 3]: $R_t$=1.27 min; MS [ESIpos]: m/z=541 [M+H]$^+$ $^1$H NMR (400 MHz, DMSO-d$_6$): δ [ppm] 1.44 (s, 6H), 3.84 (dd, 1H), 4.00 (dd, 1H), 4.29 (br. s., 1H), 4.97-5.08 (m, 2H), 5.50 (br. s., 1H), 6.87 (d, 1H), 7.32-7.41 (m, 2H), 7.45 (dt, 1H), 7.53 (td, 1H), 7.59-7.65 (m, 2H), 7.72-7.78 (m, 2H).

Example 2

5-(4-Chlorophenyl)-2-{[1-(3-chlorophenyl)-5-(2-hydroxypropan-2-yl)-1H-1,2,4-triazol-3-yl]methyl}-4-[(2S)-3,3,3-trifluoro-2-hydroxypropyl]-2,4-dihydro-3H-1,2,4-triazol-3-one

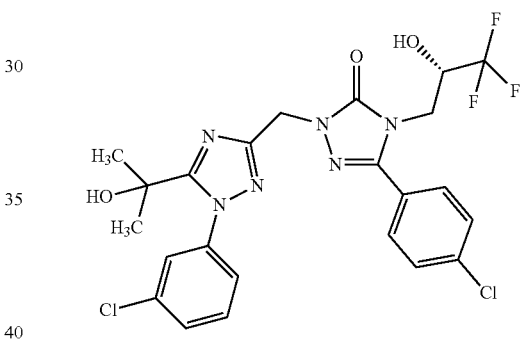

To a solution of 5-(4-chlorophenyl)-2-{[5-(2-hydroxypropan-2-yl)-1H-1,2,4-triazol-3-yl]methyl}-4-[(2S)-3,3,3-trifluoro-2-hydroxypropyl]-2,4-dihydro-3H-1,2,4-triazol-3-one (Example 4A; 375 mg, 0.84 mmol) in pyridine (10.5 ml) were added (3-chlorophenyl)boronic acid (263 mg, 1.68 mmol) and copper(II) acetate (304.9 mg, 1.68 mmol). The reaction mixture was heated to 60° C. for 2 h and then stirred at room temperature for 5 days. The reaction mixture was then diluted with MTBE and quenched with aqueous hydrochloric acid (0.5 M). After phase separation, the aqueous phase was extracted twice with ethyl acetate. The combined organic phases were dried over sodium sulfate, filtered, and concentrated in vacuo. The crude product was first purified by preparative HPLC [Method 5]. A second purification by preparative chiral HPLC [sample preparation: 62.3 mg dissolved in a mixture of 1 ml isohexane and 1 ml ethanol; injection volume: 1 ml; column: Daicel Chiralcel® OX-H 5 µm, 250×20 mm; eluent: isohexane/ethanol 75:25; flow rate: 15 ml/min; temperature: 30° C.; UV detection: 220 nm] gave 35 mg (0.06 mmol, 7.4% of th.) of the desired compound.

LC/MS [Method 1]: $R_t$=1.09 min; MS [ESIpos]: m/z=557 [M+H]$^+$ $^1$H NMR (400 MHz, DMSO-d$_6$): δ [ppm] 1.44 (s, 6H), 3.84 (dd, 1H), 4.00 (dd, 1H), 4.22-4.33 (m, 1H), 4.98-5.08 (m, 2H), 5.50 (s, 1H), 6.87 (d, 1H), 7.48-7.59 (m, 3H), 7.60-7.65 (m, 3H), 7.72-7.77 (m, 2H).

Example 3

5-(4-Chlorophenyl)-2-{[5-(2-hydroxypropan-2-yl)-1-(2-methoxyphenyl)-1H-1,2,4-triazol-3-yl]methyl}-4-[(2S)-3,3,3-trifluoro-2-hydroxypropyl]-2,4-dihydro-3H-1,2,4-triazol-3-one

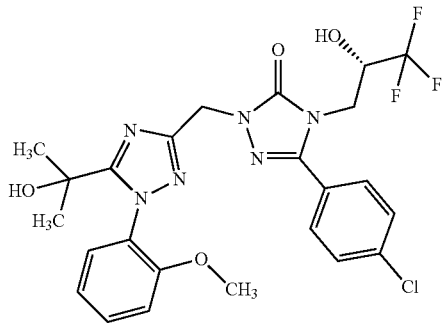 [SMILES: COc1ccccc1-n1nc(Cn2nc(-c3ccc(Cl)cc3)n(C[C@H](O)C(F)(F)F)c2=O)nc1C(C)(C)O]

To a solution of 5-(4-chlorophenyl)-2-{[5-(2-hydroxypropan-2-yl)-1H-1,2,4-triazol-3-yl]methyl}-4-[(2S)-3,3,3-trifluoro-2-hydroxypropyl]-2,4-dihydro-3H-1,2,4-triazol-3-one (Example 4A; 400 mg, 0.895 mmol) in pyridine (11.2 ml) were added (2-methoxyphenyl)boronic acid (272 mg, 1.79 mmol) and copper(II) acetate (325.2 mg, 1.79 mmol). The reaction mixture was heated to 60° C. for 2 h and then stirred at room temperature for 10 days. The reaction mixture was then diluted with MTBE and quenched with aqueous hydrochloric acid (0.5 M). After phase separation, the aqueous phase was extracted twice with ethyl acetate. The combined organic phases were dried over sodium sulfate, filtered, and concentrated in vacuo. The crude product was purified by preparative HPLC [Method 5] and the desired compound (21.4 mg, 0.04 mmol, 4.3% of th.) was obtained.

LC/MS [Method 4]: $R_t$=2.90 min; MS [ESIpos]: m/z=553 [M+H]$^+$ $^1$H NMR (600 MHz, DMSO-d$_6$): δ [ppm] 1.28 (br. s., 3H), 1.47 (br. s., 3H), 3.72 (s, 3H), 3.84 (dd, 1H), 3.99 (dd, 1H), 4.29 (br. s., 1H), 4.97-5.04 (m, 2H), 6.89 (d, 1H), 7.01 (td, 1H), 7.16 (d, 1H), 7.30 (dd, 1H), 7.47 (td, 1H), 7.61-7.64 (m, 2H), 7.73-7.77 (m, 2H).

Example 4

5-(4-Chlorophenyl)-2-{[1-(2-chlorophenyl)-5-(1-hydroxypropyl)-1H-1,2,4-triazol-3-yl]methyl}-4-[(2S)-3,3,3-trifluoro-2-hydroxypropyl]-2,4-dihydro-3H-1,2,4-triazol-3-one (diastereomeric mixture)

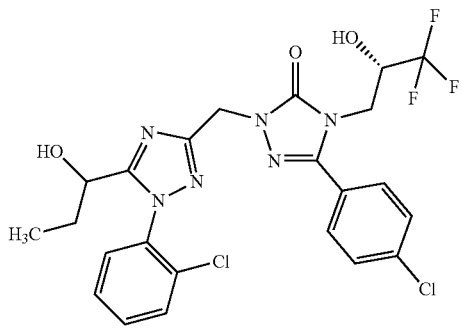 [SMILES: CCC(O)c1nc(Cn2nc(-c3ccc(Cl)cc3)n(C[C@H](O)C(F)(F)F)c2=O)nn1-c1ccccc1Cl]

To a solution of 5-(4-chlorophenyl)-2-{[1-(2-chlorophenyl)-5-propionyl-1H-1,2,4-triazol-3-yl]methyl}-4-[(2S)-3,3,3-trifluoro-2-hydroxypropyl]-2,4-dihydro-3H-1,2,4-triazol-3-one (Example 12 A, 103 mg, 0.185 mmol) in ethanol (5 ml) was added sodium borohydride (2.11 mg, 0.056 mmol) at 0° C. The reaction mixture was stirred for 1 h at 0° C., then quenched with aqueous hydrochloric acid 1N and extracted with dichloromethane. The combined organic phases were dried over sodium sulfate, filtered, and concentrated in vacuo. The crude product was purified by preparative HPLC [Method 5] and the desired compound (84.7 mg, 0.15 mmol, 81.9% of th.) was obtained as a mixture of diastereomers.

LC/MS [Method 4]: $R_t$=3.09 min; MS [ESIpos]: m/z=557 [M+H]$^+$ $^1$H NMR (400 MHz, DMSO-d$_6$): δ [ppm] 0.80 (t, 3H), 1.65-1.81 (m, 2H), 3.85 (dd, 1H), 4.01 (dd, 1H), 4.24-4.36 (m, 2H), 5.01-5.14 (m, 2H), 6.90 (br. s, 1H), 7.50-7.56 (m, 1H), 7.57-7.65 (m, 4H), 7.68-7.78 (m, 3H).

The two diastereomers were separated by preparative chiral HPLC [sample preparation: 84.7 mg dissolved in 5 ml ethanol; injection volume: 0.5 ml; column: Daicel Chiralcel® OX-H 5 μm, 250×20 mm; eluent: isohexane/ethanol 80:20; flow rate: 15 ml/min; temperature: 25° C.; UV detection: 220 nm]. After separation, 29.7 mg of diastereomer 1 (Example 5), which eluted first, and 26.6 mg of diastereomer 2 (Example 6), which eluted later, were isolated.

Example 5

5-(4-Chlorophenyl)-2-{[1-(2-chlorophenyl)-5-(1-hydroxypropyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 1)

Analytical chiral HPLC: $R_t$=2.34 min, d.e.=100% [column: Daicel Chiralpack OX-3 3 μm, 50×4.6 mm; eluent: isohexane/ethanol 80:20; flow rate: 1 ml/min; temperature: 30° C.; UV detection: 220 nm].

$^1$H NMR (400 MHz, DMSO-d$_6$): δ [ppm] 0.80 (t, 3H), 1.64-1.81 (m, 2H), 3.85 (dd, 1H), 4.01 (dd, 1H), 4.25-4.34 (m, 2H), 5.02-5.13 (m, 2H), 5.51 (br. s., 1H), 6.89 (d, 1H), 7.50-7.56 (m, 1H), 7.57-7.65 (m, 4H), 7.69-7.78 (m, 3H).

Example 6

5-(4-Chlorophenyl)-2-{[1-(2-chlorophenyl)-5-(1-hydroxypropyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 2)

Analytical chiral HPLC: $R_t$=3.42 min, d.e.=100% [column: Daicel Chiralpack OX-3 3 μm, 50×4.6 mm; eluent: isohexane/ethanol 80:20; flow rate: 1 ml/min; temperature: 30° C.; UV detection: 220 nm].

$^1$H NMR (400 MHz, DMSO-d$_6$): δ [ppm] 0.80 (t, 3H), 1.63-1.82 (m, 2H), 3.85 (dd, 1H), 4.00 (dd, 1H), 4.25-4.34 (m, 2H), 5.07 (s, 2H), 5.51 (br. s., 1H), 6.90 (d, 1H), 7.50-7.56 (m, 1H), 7.57-7.65 (m, 4H), 7.68-7.78 (m, 3H).

Example 7

5-(4-Chlorophenyl)-2-{[1-(2-chlorophenyl)-5-(1-hydroxy-2-methylpropyl)-1H-1,2,4-triazol-3-yl]methyl}-4-[(2S)-3,3,3-trifluoro-2-hydroxypropyl]-2,4-dihydro-3H-1,2,4-triazol-3-one (diastereomeric mixture)

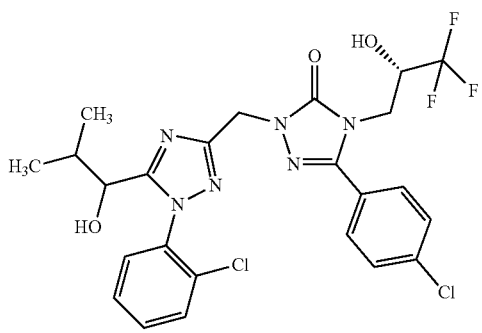 [SMILES: CC(C)C(O)c1nc(Cn2nc(-c3ccc(Cl)cc3)n(C[C@H](O)C(F)(F)F)c2=O)nn1-c1ccccc1Cl]

To a solution of 5-(4-chlorophenyl)-2-({[1-(2-chlorophenyl)-5-isobutyryl-1H-1,2,4-triazol-3-yl]methyl}-4-[(2S)-3,3,3-trifluoro-2-hydroxypropyl]-2,4-dihydro-3H-1,2,4-triazol-3-one (Example 13A; 49.7 mg, 0.087 mmol) in ethanol (2.4 ml) was added sodium borohydride (0.99 mg, 0.026 mmol) at 0° C. The reaction mixture was stirred for 1 h at 0° C., then quenched with aqueous 1 N hydrochloric acid and extracted with dichloromethane. The combined organic phases were dried over sodium sulfate, filtered, and concentrated in vacuo. The crude product was purified by preparative [Method 5] and the desired compound (43.2 mg, 0.08 mmol, 86.6% of th.) was obtained as a mixture of diastereomers.

LC/MS [Method 4]: $R_t$=3.31 min; MS [ESIpos]: m/z=571 [M+H]$^+$ $^1$H NMR (400 MHz, DMSO-d$_6$): δ [ppm] 0.69 (d, 3H), 0.88 (d, 3H), 1.99 (br. s., 1H), 3.85 (dd, 1H), 3.92-4.04 (m, 2H), 4.30 (br. s., 1H), 5.02-5.14 (m, 2H), 5.59 (br. s., 1H), 6.90 (t, 1H), 7.50-7.65 (m, 5H), 7.69-7.77 (m, 3H).

The two diastereomers were separated by preparative chiral HPLC [sample preparation: 38.2 mg dissolved in a mixture of 3.5 ml ethanol and 0.5 ml acetonitrile; injection volume: 0.5 ml; column: Daicel Chiralcel® OX-H 5 μm, 250×20 mm; eluent: isohexane/ethanol 70:30; flow rate: 15 ml/min; temperature: 25° C.; UV detection: 220 nm]. After separation, 13.5 mg of diastereomer 1 (Example 8), which eluted first, and 13.5 mg of diastereomer 2 (Example 9), which eluted later, were isolated.

Example 8

5-(4-Chlorophenyl)-2-{[1-(2-chlorophenyl)-5-(1-hydroxy-2-methylpropyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 1)

Analytical chiral HPLC: $R_t$=5.77 min, d.e.=100% [column: Daicel Chiralcel® OX-H 5 m, 250×4.6 mm; eluent: isohexane/ethanol 70:30+0.2% TFA+1% H$_2$O; flow rate: 1 ml/min; temperature: 30° C.; UV detection: 220 nm].

$^1$H NMR (400 MHz, DMSO-d$_6$): δ [ppm] 0.69 (d, 3H), 0.88 (d, 3H), 1.99 (br. s., 1H), 3.85 (dd, 1 EH), 3.93-4.03 (m, 2H), 4.29 (br. s., 1H), 5.02-5.14 (m, 2H), 5.58 (br. s., 1H), 6.89 (d, 1H), 7.50-7.65 (m, 5H), 7.68-7.77 (m, 3H).

Example 9

5-(4-Chlorophenyl)-2-{[1-(2-chlorophenyl)-5-(1-hydroxy-2-methylpropyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 2)

Analytical chiral HPLC: $R_t$=6.98 min, d.e.=100% [column: Daicel Chiralcel® OX-H 5 μm, 250×4.6 mm; eluent: isohexane/ethanol 70:30+0.2% TFA+1% H$_2$O; flow rate: 1 ml/min; temperature: 30° C.; UV detection: 220 nm].

$^1$H NMR (400 MHz, DMSO-d$_6$): δ [ppm] 0.69 (d, 3H), 0.88 (d, 3H), 2.00 (br. s., 1H), 3.85 (dd, 1H), 3.91-4.05 (m, 2H), 4.24-4.36 (m, 1H), 5.03-5.13 (m, 2H), 5.59 (br. s., 1H), 6.90 (d, 1H), 7.50-7.65 (m, 5H), 7.69-7.77 (m, 3H).

Example 10

5-(4-Chlorophenyl)-2-{[1-(3-chlorophenyl)-5-(2,2,2-trifluoro-1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomeric mixture)

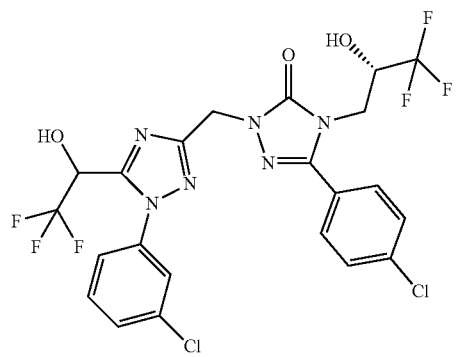 [SMILES: O=c1n(Cc2nc(C(O)C(F)(F)F)n(-c3cccc(Cl)c3)n2)nc(-c2ccc(Cl)cc2)n1C[C@H](O)C(F)(F)F]

To a solution of 5-(4-chlorophenyl)-2-{[5-(2,2,2-trifluoro-1-hydroxyethyl)-1H-1,2,4-triazol-3-yl]-methyl}-4-[(2S)-3,3,3-trifluoro-2-hydroxypropyl]-2,4-dihydro-3H-1,2,4-triazol-3-one (Example 16A; 205 mg, 0.42 mmol) in pyridine (5.2 ml) were added (3-chlorophenyl)boronic acid (131.7 mg, 0.84 mmol) and copper(II) acetate (153 mg, 0.842 mmol). The reaction mixture was stirred for 4 days at room temperature, after which extra boronic acid (100 mg, 0.76 mmol) was added due to incomplete conversion. The reaction mixture was heated to 60° C. for 5 h and then stirred at room temperature for 2 days. The reaction mixture was then diluted with MTBE and quenched with aqueous hydrochloric acid (0.5 M). After phase separation, the aqueous phase was extracted twice with MTBE. The combined organic phases were dried over sodium sulfate, filtered, and concentrated in vacuo. The crude product was first purified by preparative HPLC [Method 5]. A second purification by preparative chiral HPLC [sample preparation: 44 mg dissolved in a mixture of 1 ml isopropanol and 1 ml isohexane; injection volume: 0.5 ml; column: Daicel Chiralpak IC 5 μm, 250×20 mm; eluent: isohexane/isopropanol 93:7; flow rate: 15 ml/min; temperature: 25° C.; UV detection: 220 nm]

gave 18 mg of diastereomer 1 (example 11), which eluted first, and 11 mg of diastereomer 2 (Example 12), which eluted later.

Example 11

5-(4-Chlorophenyl)-2-{[1-(3-chlorophenyl)-5-(2,2,2-trifluoro-1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 1)

Analytical chiral HPLC: R$_t$=4.97 min, d.e.=99.3% [column: Daicel Chiralpak IC 5 µm, 250×4.6 mm; eluent: isohexane/isopropanol 90:10; flow rate: 1 ml/min; temperature: 25° C.; UV detection: 220 nm].

$^1$H NMR (500 MHz, DMSO-d$_6$): δ [ppm] 3.85 (dd, 1H), 4.00 (dd, 1H), 4.29 (br. s., 1H), 5.08-5.17 (m, 2H), 5.43-5.51 (m, 1H), 6.89 (d, 1H), 7.49 (br. d, 1H), 7.53-7.66 (m, 5H), 7.68-7.72 (m, 1H), 7.73-7.77 (m, 2H).

Example 12

5-(4-Chlorophenyl)-2-{[1-(3-chlorophenyl)-5-(2,2,2-trifluoro-1-hydroxyethyl)-1H-1,2,4-triazol-3-yl]methyl}-4-[(2S)-3,3,3-trifluoro-2-hydroxypropyl]-2,4-dihydro-3H-1,2,4-triazol-3-one (diastereomer 2)

Analytical chiral HPLC: R$_t$=5.37 min, d.e.=98% [column: Daicel Chiralpak IC 5 µm, 250×4.6 mm; eluent: isohexane/isopropanol 90:10; flow rate: 1 ml/min; temperature: 25° C.; UV detection: 220 nm].

$^1$H NMR (500 MHz, DMSO-d$_6$): δ [ppm] 3.85 (dd, 1H), 4.00 (dd, 1H), 4.30 (br. s., 1H), 5.13 (s, 2H), 5.44-5.51 (m, 1H), 6.90 (br. s., 1H), 7.49 (br. s., 1H), 7.54-7.66 (m, 5H), 7.71 (t, 1H), 7.72-7.77 (d, 2H).

Example 13

5-(4-Chlorophenyl)-2-{[1-(2-chlorophenyl)-5-(2-hydroxypropan-2-yl)-1H-1,2,4-triazol-3-yl]methyl}-4-[(2S)-3,3,3-trifluoro-2-hydroxypropyl]-2,4-dihydro-3H-1,2,4-triazol-3-one

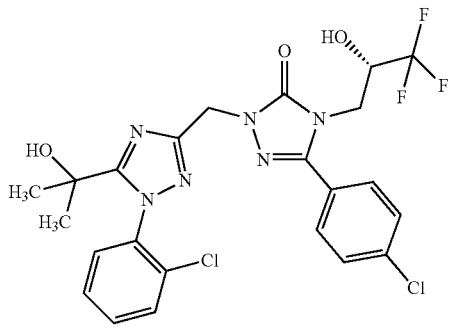 [SMILES: CC(C)(O)c1nc(Cn2nc(-c3ccc(Cl)cc3)n(C[C@H](O)C(F)(F)F)c2=O)nn1-c1ccccc1Cl]

Under argon atmosphere, to a solution of 2-{[5-acetyl-1-(2-chlorophenyl)-1H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one (Example 21A; 50 mg, 0.092 mmol) in THF (1.5 ml) was added dropwise methylmagnesium bromide (67.7 µL, 0.203 mmol, 3M solution in diethylether) at 0° C. After 20 min of stirring at 0° C., the reaction mixture stirred for 3 h at room temperature. The reaction mixture was then quenched with saturated aqueous ammonium chloride and diluted with water. After phase separation, the aqueous phase was extracted with ethylacetate. The combined organic phases were dried over sodium sulfate, filtered, and concentrated in vacuo. The crude product was purified by preparative HPLC [Method 5], and the desired compound (42 mg, 0.07 mmol, 97% purity, 79.1% of th.) was obtained.

LC/MS [Method 1]: R$_t$=1.01 min; MS [ESIpos]: m/z=557 [M+H]$^+$ $^1$H NMR (400 MHz, DMSO-d$_6$): δ [ppm] 1.35 (br. s., 3H), 1.51 (br. s., 3H), 3.84 (dd, 1H), 3.99 (dd, 1H), 4.28 (br. s., 1H), 4.98-5.09 (m, 2H), 5.28 (br. s., 1H), 6.88 (br. s., 1H), 7.46 (td, 1H), 7.49-7.65 (m, 5H), 7.70-7.78 (m, 2H).

Example 14

2-[1-(2-Chlorophenyl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-5-yl]-2-hydroxypropanoic acid (diastereomeric mixture)

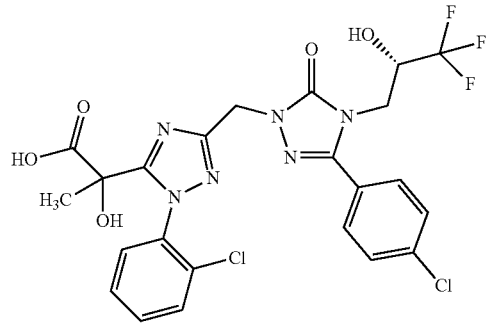 [SMILES: CC(O)(C(=O)O)c1nc(Cn2nc(-c3ccc(Cl)cc3)n(C[C@H](O)C(F)(F)F)c2=O)nn1-c1ccccc1Cl]

To a solution of 2-[3-({4-[(2S)-2-{[tert-butyl(dimethyl)silyl]oxy}-3,3,3-trifluoropropyl]-3-(4-chlorophenyl)-5-oxo-4,5-dihydro-1H-1,2,4-triazol-1-yl}methyl)-1-(2-chlorophenyl)-1,2,4-triazol-5-yl]-2-hydroxypropanoic acid (Example 24A; 200 mg, 285 µmol) in THF (18 ml) was added a solution of tetra-n-butyl-ammonium fluoride (1 M in THF; 1.4 ml; 1.4 mmol) and the mixture was stirred 1 h at room temperature. The solvent was removed at a rotary evaporator. The residue was dissolved in some DMSO, diluted with 1 M hydrochloric acid (1 ml) and purified twice by preparative HPLC (first with method 6 then with method 7) to give 140 mg (96% purity, 80% of th.) of the title compound.

LC-MS [Method 1]: R$_t$=0.92 min; MS(ESIpos): m/z=587 [M+H]$^+$ $^1$H-NMR (400 MHz, DMSO-d$_6$): δ [ppm]=1.64 (s, 3H), 3.83 (dd, 1H), 3.99 (dd, 1H), 4.23-4.36 (m, 1H), 4.99-5.14 (m, 2H), 6.02 (br. s, 1H), 6.90 (d, 1H), 7.38-7.57 (m, 3H), 7.58-7.67 (m, 3H), 7.70-7.79 (m, 2H), 13.10 (br. s, 1H).

In order to separate the diastereomers, 133 mg of the obtained product were submitted to preparative HPLC on a chiral stationary phase (Daicel Chiralpak IC 5 µM; 250 mm×20 mm; eluent isohexane/0.2% trifluoroacetic acid in ethanol 85:15; flow 15 ml/min; detection 220 nM). The first eluted diastereomer is described hereafter as example 15, whereas the later eluted diastereomer is described as example 16.

Example 15

2-[1-(2-Chlorophenyl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-5-yl]-2-hydroxypropanoic acid (diastereomer 1)

First eluted diastereomer after preparative chiral HPLC of 133 mg of the product obtained as example 13. The corresponding fractions were diluted with water, evaporated partially at a rotary evaporator at 35° C. The remaining solution was lyophilized. In order to remove some remaining impurities (probably from the solvents), this product was dissolved in a few ml DMSO and purified via preparative HPLC (Method 7). The product fraction was evaporated to dryness at a rotary evaporator, redissolved in acetonitrile and water and lyophilized, giving 42 mg (31% of th.) of the title compound (98% d.e.).

LC-MS [Method 2]: $R_t$=1.60 min; MS(ESIpos): m/z=587 [M+H]$^+$ $^1$H-NMR (400 MHz, DMSO-d$_6$): δ [ppm]=1.65 (s, 3H), 3.84 (dd, 1H), 4.00 (dd, 1H), 4.22-4.36 (m, 1H), 5.01-5.13 (m, 2H), 6.02 (br. s, 1H), 6.89 (d, 1H), 7.40-7.48 (m, 2H), 7.51-7.57 (m, 1H), 7.59-7.66 (m, 3H), 7.72-7.78 (m, 2H), 13.09 (br. s, 1H).

Example 16

2-[1-(2-Chlorophenyl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-5-yl]-2-hydroxypropanoic acid (diastereomer 2)

Later eluted diastereomer after preparative chiral HPLC of 133 mg of the product obtained as example 13. The corresponding fractions were diluted with water, evaporated partially at a rotary evaporator at 35° C. The remaining solution was lyophilized. In order to remove some remaining impurities (probably from the solvents), this product was dissolved in a few ml DMSO and purified via preparative HPLC (Method 7). The product fraction was evaporated to dryness at a rotary evaporator, redissolved in acetonitrile and water and lyophilized, giving 34 mg (25% of th.) of the title compound (99% d.e.).

LC-MS [Method 2]: $R_t$=1.60 min; MS(ESIpos): m/z=587 [M+H]$^+$ $^1$H-NMR (400 MHz, DMSO-d$_6$): δ [ppm]=1.65 (s, 3H), 3.84 (dd, 1H), 3.99 (dd, 1H), 4.22-4.36 (m, 1H), 5.01-5.13 (m, 2H), 6.02 (br. s, 1H), 6.89 (d, 1H), 7.40-7.57 (m, 3H), 7.59-7.66 (m, 3H), 7.72-7.78 (m, 2H), 13.12 (br. s, 1H).

Example 17

2-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-(3-chloropyridin-2-yl)-1H-1,2,4-triazol-5-yl]-2-hydroxypropanoic acid (diastereomeric mixture)

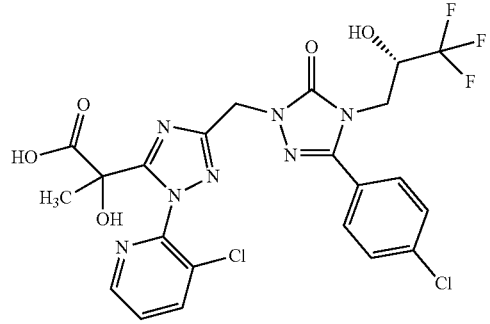 [SMILES: CC(O)(C(=O)O)c1nc(Cn2nc(-c3ccc(Cl)cc3)n(C[C@H](O)C(F)(F)F)c2=O)nn1-c1ncccc1Cl]

To a solution of 2-[3-({4-[(2S)-2-{[tert-butyl(dimethyl)silyl]oxy}-3,3,3-trifluoropropyl]-3-(4-chlorophenyl)-5-oxo-4,5-dihydro-1H-1,2,4-triazol-1-yl}methyl)-1-(3-chloropyridin-2-yl)-1,2,4-triazol-5-yl]-2-hydroxypropanoic acid (Example 27A; 81.0 mg, 115 µmol) in THF (7.2 ml) was added a solution of tetra-n-butyl-ammonium fluoride (1M in THF; 580 µl; 580 µmol) and the mixture was stirred 1 h at room temperature. The solvent was removed at a rotary evaporator. The residue was dissolved in some DMSO, diluted with 1 M hydrochloric acid (1 ml) and purified twice by preparative HPLC (first with method 6, then with method 7) to give 46.0 mg (98% purity, 66% of th.) of the title compound.

LC-MS [Method 1]: $R_t$=0.88 min; MS(ESIpos): m/z=588 [M+H]$^+$ $^1$H-NMR (400 MHz, DMSO-d$_6$): δ [ppm]: 1.70 (s, 3H), 3.84 (dd, 1H), 4.00 (dd, 1H), 4.30 (d, 1H), 5.03-5.15 (m, 2H), 5.85 (br. s, 1H), 6.90 (dd, 1H), 7.58-7.66 (m, 3H), 7.75 (d, 2H), 8.20 (dd, 1H), 8.43 (d, 1H), 13.07 (br. s, 1H). The observed dd at 6.90 ppm was interpreted as two doublets, one for each diastereomer of the mixture.

Experimental Section—Biological Assays

Abbreviations and Acronyms

Acc. No. accession number
AVP arginine vasopressin
$B_{max}$ maximal ligand binding capacity
BSA bovine serum albumin
cAMP cyclic adenosine monophosphate
Cat. No. catalogue number
cDNA complementary deoxyribonucleic acid
CHO chinese hamster ovary
CRE cAMP response element
Ct cycle threshold
DMEM/F12 Dulbecco's modified Eagle's medium/Ham's F12 medium (1:1)
DNA deoxyribonucleic acid
DMSO dimethylsulfoxide
DTT dithiothreitol
EC$_{50}$ half-maximal effective concentration
EDTA ethylenediamine-tetraacetic acid FAM carboxyfluorescein succinimidyl ester
f.c. final concentration
FCS fetal calf serum
HCl hydrochloric acid
HEPES 4-(2-hydroxyethyl)piperazine-1-ethanesulfonic acid
$IC_{50}$ half-maximal inhibitory concentration
$K_d$ dissociation constant
$K_i$ dissociation constant of an inhibitor
mRNA messenger ribonucleic acid
PBS phosphate buffered saline
PEG polyethylene glycol
p.o. per os, peroral
RNA ribonucleic acid
RTPCR real-time polymerase chain reaction
SPA scintillation proximity assay
TAMRA carboxytetramethylrhodamine
TRIS; Tris 2-amino-2-hydroxymethylpropane-1,3-diol Demonstration of the activity of the compounds of the present invention may be accomplished through in vitro, ex vivo, and in vivo assays that are well known in the art. For example, to demonstrate the activity of the compounds of the present invention, the following assays may be used.

B-1. Cellular In Vitro Assay for Determining Vasopressin Receptor Activity

The identification of agonists and antagonists of the V1a and V2 vasopressin receptors from humans, rats and dogs as well as the quantification of the activity of the compounds of the invention is carried out using recombinant cell lines. These cell lines originally derive from a hamster's ovary epithelial cell (Chinese Hamster Ovary, CHO K1, ATCC: American Type Culture Collection, Manassas, Va. 20108, USA). The test cell lines constitutively express the human, rat or dog V1a or V2 receptors. In case of the $G_{\alpha q}$-coupled V1a receptors, cells are also stably transfected with a modified form of the calcium-sensitive photoproteins aequorin (human and rat V1a) or obelin (dog V1a), which, after reconstitution with the cofactor coelenterazine, emit light when there are increases in free calcium concentrations [Rizzuto R, Simpson A W, Brini M, Pozzan T, *Nature* 358, 325-327 (1992); Illarionov B A, Bondar V S, Illarionova V A, Vysotski E S, Gene 153 (2), 273-274 (1995)]. The resulting vasopressin receptor cells react to stimulation of the recombinantly expressed V1a receptors by intracellular release of calcium ions, which can be quantified by the resulting photoprotein luminescence. The $G_s$-coupled V2 receptors are stably transfected into cell lines expressing the gene for firefly luciferase under control of a CRE-responsible promoter. Activation of V2 receptors induces the activation of the CRE-responsive promoter via cAMP increase, thereby inducing the expression of firefly luciferase. The light emitted by photoproteins of V1a cell lines as well as the light emitted by firefly luciferase of V2 cell lines corresponds to the activation or inhibition of the respective vasopressin receptor. The bioluminescence of the cell lines is detected using a suitable luminometer [Milligan G, Marshall F, Rees S, *Trends in Pharmacological Sciences* 17, 235-237 (1996)].

Test Procedure:

Vasopressin V1a Receptor Cell Lines:

On the day before the assay, the cells are plated out in culture medium (DMEM/F12, 2% FCS, 2 mM glutamine, 10 mM HEPES, 5 μg/ml coelenterazine) in 384-well microtiter plates and kept in a cell incubator (96% humidity, 5% v/v $CO_2$, 37° C.). On the day of the assay, test compounds in various concentrations are placed for 10 minutes in the wells of the microtiter plate before the agonist [$Arg^8$]-vasopressin at $EC_{50}$ concentration is added. The resulting light signal is measured immediately in a luminometer.

Vasopressin V2 Receptor Cell Lines:

On the day before the assay, the cells are plated out in culture medium (DMEM/F12, 2% FCS, 2 mM glutamine, 10 mM HEPES) in 384-well microtiter plates and kept in a cell incubator (96% humidity, 5% v/v $CO_2$, 37° C.). On the day of the assay, test compounds in various concentrations and the agonist [$Arg^8$]-vasopressin at $EC_{50}$ concentration are added together to the wells, and plates are incubated for 3 hours in a cell incubator. Upon addition of the cell lysis reagent Triton™ and the substrate luciferin, luminescence of firefly luciferase is measured in a luminometer.

Table 1A below lists individual $IC_{50}$ values for the compounds of the invention (including racemic mixtures as well as separated enantiomers) that were obtained from cell lines transfected with the human V1a or V2 receptor:

TABLE 1A

| Example No. | $IC_{50}$ hV1a [μM] | $IC_{50}$ hV2 [μM] | ratio $IC_{50}$ hV2/hV1a |
|---|---|---|---|
| 1 | 0.0066 | 0.0249 | 3.8 |
| 2 | 0.0219 | 0.0033 | 0.2 |
| 3 | 0.0008 | 0.0019 | 2.4 |
| 4 | 0.0007 | 0.0047 | 6.7 |
| 5 | 0.0016 | 0.0042 | 2.6 |
| 6 | 0.0007 | 0.0084 | 12.0 |
| 7 | 0.0008 | 0.0051 | 6.4 |
| 8 | 0.0006 | 0.0022 | 3.7 |
| 9 | 0.0009 | 0.0254 | 28.2 |
| 10 | 0.0135 | 0.0021 | 0.2 |
| 11 | 0.0149 | 0.0018 | 0.1 |
| 12 | 0.0022 | 0.0348 | 15.8 |
| 13 | 0.0021 | 0.0069 | 3.3 |
| 14 | 0.0165 | 0.0760 | 4.6 |
| 15 | 0.0035 | 0.0265 | 7.6 |
| 16 | 0.0055 | 0.2520 | 45.8 |

B-2. Radioactive Binding Assay $IC_{50}$ and $K_i$ values can be determined in radioactive binding assays using membrane fractions of recombinant human embryonic kidney cell line 293 (HEK293) or CHO-K1 cell lines expressing the respective human vasopressin V1a and V2 receptors.

Human recombinant vasopressin V1a receptors expressed in HEK293 cells are used in 50 mM Tris-HCl buffer, pH 7.4, 5 mM $MgCl_2$, 0.1% BSA using standard techniques. Aliquots of prepared membranes are incubated with test compounds in various concentrations in duplicates and 0.03 nM [$^{125}$I]Phenylacetyl-D-Tyr(Me)-Phe-Gln-Asn-Arg-Pro-Arg-Tyr-$NH_2$ for 120 minutes at 25° C. Non-specific binding is estimated in the presence of 1 μM [$Arg^8$]Vasopressin. Receptors are filtered and washed, the filters are then counted to determine [$^{125}$I]Phenylacetyl-D-Tyr(Me)-Phe-Gln-Asn-Arg-Pro-Arg-Tyr-$NH_2$ specifically bound.

CHO-K1 cells stably transfected with a plasmid encoding human vasopressin V2 receptor are used to prepare membranes in 50 mM Tris-HCl buffer, pH 7.4, 10 mM $MgCl_2$, 0.1% BSA using standard techniques. Aliquots of prepared membrane are incubated with test compounds in various concentrations in duplicates and 4 nM [$^3$H]($Arg^8$)-Vasopressin for 120 minutes at 25° C. Non-specific binding is estimated in the presence of 1 mM ($Arg^8$)-vasopressin. Membranes are filtered and washed 3 times and the filters are counted to determine [$^3$H]($Arg_8$)-Vasopressin specifically bound.

$IC_{50}$ values are determined by a non-linear, least squares regression analysis using MathIQ™ (ID Business Solutions Ltd., UK). The inhibition constant $K_i$ is calculated using the equation of Cheng and Prusoff (Cheng, Y., Prusoff, W. H., Biochem. Pharmacol. 22:3099-3108, 1973).

B-3. Cellular In Vitro Assay for Detecting the Action of Vasopressin V1a Receptor Antagonists on the Regulation of Pro-Fibrotic Genes The cell line H9C2 (American Type Culture Collection ATCC No. CRL-1446), described as a cardiomyocyte type isolated from rat cardiac tissue, endogenously expresses the vasopressin V1a receptor AVPR1A in high copy number, whereas AVPR2 expression cannot be detected. Likewise, the cell line NRK49F (ATCC No. CRL1570) isolated from rat kidney tissue, shows similar expression pattern of high AVPR1A mRNA expression and diminishing AVPR2 expression. For cell assays detecting the inhibition of AVPR1A receptor-dependent regulation of gene expression by receptor antagonists, the procedure is as follows:

H9C2 cells or NRK49F cells are seeded in 6-well microtiter plates for cell culture at a cell density of 50 000 cells/well in 2.0 ml of Opti-MEM medium (Invitrogen Corp., Carlsbad, Calif., USA, Cat. No. 11058-021) and held in a cell incubator (96% humidity, 8% v/v $CO_2$, 37° C.). After 24 hours, sets of three wells (triplicate) are charged with vehicle solution (negative control) and vasopressin solution ([Arg8]-vasopressin acetate, Sigma, Cat. No. V9879), or test compound (dissolved in vehicle: water with 20% v/v ethanol) and vasopressin solution. In the cell culture, the final vasopressin concentration is 1 nM. The test compound solution is added to the cell culture in small volumes, so that a final concentration of 0.03% of ethanol in the cell assay is not exceeded. After an incubation time of 5 hours, the culture supernatant is drawn off under suction, the adherent cells are lysed in 350 μl of RLT buffer (Qiagen, Cat. No. 79216), and the RNA is isolated from the lysate using the RNeasy kit (Qiagen, Cat. No. 74104). This is followed by DNAse digestion (Invitrogen, Cat. No. 18068-015), cDNA synthesis (Promaga, ImProm-II Reverse Transcription System, Cat. No. A3800) and Reverse Transcription Polymerase Chain Reaction (RTPCR) (pPCR MasterMix RT-QP2X-03-075, Eurogentec, Seraing, Belgium). All procedures take place in accordance with the working protocols of the test reagents' manufacturers. The primer sets for the RTPCR are selected on the basis of the mRNA gene sequences (NCBI GenBank Entrez Nucleotide Data Base) using the Primer3Plus program with 6-FAM TAMRA-labelled probes. The RTPCR for determining the relative mRNA expression in the cells of the various assay batches is carried out using the Applied Biosystems ABI Prism 7700 Sequence Detector in 384-well microtiter plate format in accordance with the instrument operating instructions. The relative gene expression is represented by the delta-delta Ct value [Applied Biosystems, User Bulletin No. 2 ABI Prism 7700 SDS, Dec. 11, 1997 (updated October 2001)] with reference to the level of expression of the ribosomal protein L-32 gene (GenBank Acc. No. NM_013226) and the threshold Ct value of Ct=35.

B-4. Inhibition of Vasopressin Induced Aggregation of Human Platelets

Human platelets endogenously express the V1a receptor. It was found that relatively high vasopressin concentrations (ca. 50-100 nM) stimulate platelet aggregation ex vivo. Therefore, platelets enriched from human blood may serve as a V1a expressing tissue for pharmacological studies with corresponding high concentrations of vasopressin antagonists.

Human blood is collected in a 10 mM trisodium citrate solution by venous puncture from nonsmoking healthy volunteers (n=4-8) who were drug free for at least 1 week. Platelet-rich plasma (PRP) is obtained by centrifuging the blood sample at 140 g for 20 min at 4° C. The resulting pellet is further centrifuged (15.000 rpm, 2 min) to produce platelet-poor plasma (PPP). Platelet aggregation is measured turbidimetrically using an aggregometer (APACT 4). The reaction is followed by monitoring changes in light transmission on 178 μL PRP aliquots, under continuous stirring at 37° C., against PPP control. Various concentrations of vasopressin antagonists (in 2 μL) are added to PRP 5 min before the addition of 20 μL Arg-vasopressin (final concentration 100 nM. The inhibitory effects of the compounds are determined by measuring the height of the aggregation wave from the bottom of the shape change compared with the control response. IC50 values are calculated a dose-response inhibition curve by an iterative nonlinear regression program.

B-5. Effects on the Contraction of Isolated Rat Vessel Rings

Isolated Aorta

Test compounds can be investigated on isolated aortic rings from male Wistar rats endogenously expressing the V1a receptor. Male Wistar rats are euthanized using carbon dioxide. The aorta is removed and placed in ice-cold Krebs-Henseleit buffer of following composition (in mmol/l): NaCl 112, KCl 5.9, $CaCl_2$ 2.0, $MgCl_2$ 1.2, $NaH_2PO_4$ 1.2, $NaHCO_3$ 25, glucose 11.5. The aorta is cut into 3 mm rings and transferred to 20 ml organ baths containing Krebs-Henseleit solution equilibrated with 95% $O_2$, 5% $CO_2$ at 37° C. For recording of isometric tension the rings are mounted between two hooks. The resting tension is adjusted to 3 g. After an equilibration period, each experiment is started by exposing the preparation to K+ (50 mM) Krebs-Henseleit solution. The aortic rings are than pre-contracted using 1 nmol/l Arg-vasopressin. After a stable contraction is established, a cumulative dose response curve of the test compound is constructed. The stabilized contraction induced by Arg-vasopressin is defined as 100% tension. The relaxation is expressed as percentage tension.

Isolated A. Renalis

Male Wistar rats (200-250 g) are euthanized using carbon dioxide. The A. renalis is removed and placed in ice-cold Krebs-Henseleit buffer of following composition (in mmol/l): NaCl 112, KCl 5.9, $CaCl_2$ 2.0, $MgCl_2$ 1.2, $NaH_2PO_4$ 1.2, $NaHCO_3$ 25, glucose 11.5. For measurement of isometric tension, ring segments, 2 mm in length, are mounted in a small vessel chamber myograph (Danish Myo Technology A/S, Denmark) using two tungsten wires fixed to mounting jaws. One mounting jaw is attached to a micrometer, allowing control of vessel circumference. The other mounting jaw is attached to a force transducer for measurement of tension development. The whole preparation is kept in a chamber with physiological salt solution at 37° C., bubbled with oxygen. After a 30 min equilibration period, the vessels are stretched to their optimal lumen diameter for active tension development which is determined based on the internal circumference-wall tension ratio. The internal circumference is set to 90% of what the vessels would have if they are exposed to a passive tension equivalent to that produced by a transmural pressure of 100 mmHg.

Afterwards, the vessels are washed three times with Krebs-Henseleit buffer and left to equilibrate for 30 min. The contractility is then tested by a twofold exposure to a high $K^+$ solution (50 mmol/l KCl). After washing with Krebs-Henseleit buffer the vessels are then pre-contracted using 1 nmol/l Arg-vasopressin. After a stable contraction is established, a cumulative dose response curve of the test compound is constructed. The stabilized contraction induced by Arg-vasopressin is defined as 100% tension. The relaxation is expressed as percentage tension.

B-6. In Vivo Assay for Detecting Cardiovascular Effects: Blood Pressure Measurement in Anaesthetized Rats (Vasopressin 'Challenge' Model)

Male Sprague-Dawley rats (250-350 g body weight) are used under ketamine/xylazine/pentobarbital injection anaesthesia. Polyethylene tubes (PE-50, Intramedic®), prefilled with heparin-containing (500 IU/ml) isotonic sodium chloride solution, are introduced into the jugular vein and the femoral vein and then tied in. Arg-vasopressin (SIGMA) is injected via one venous access, with the aid of a syringe; the test substance is administered via the second venous access. For determination of the systolic blood pressure, a pressure catheter (Millar SPR-320 2F) is tied into the carotid artery. The arterial catheter is connected to a pressure transducer which feeds its signals to a recording computer equipped with suitable recording software. In a typical experiment, the experimental animal is administered 3-4 successive bolus injections at intervals of 10-15 min with a defined amount of Arg-vasopressin (30 ng/kg) in isotonic sodium chloride solution. When the blood pressure has reached initial levels again, the test substance is administered as a bolus, with subsequent continuous infusion, in a suitable solvent. After this, at defined intervals (10-15 min), the same amount of Arg-vasopressin as at the start is administered again. On the basis of the blood pressure values, a determination is made of the extent to which the test substance counteracts the hypertensive effect of Arg-vasopressin. Control animals only receive solvent instead of the test substance.

Following intravenous administration, the compounds of the invention, in comparison to the solvent controls, bring about an inhibition of the blood pressure increase caused by Arg-vasopressin.

B-7. In Vivo Assay for Detecting Cardiovascular Effects: Diuresis Investigations in Conscious Rats Kept in Metabolism Cages Wistar rats (220-450 g body weight) are kept with free access to feed (Altromin) and drinking water. During the experiment, the animals are kept with free access to drinking water for 4 to 8 or up to 24 hours individually in metabolism cages suitable for rats of this weight class (Tecniplast Deutschland GmbH, D-82383 Hohenpeißenberg). At the beginning of the experiment, the animals are administered the test substance in a volume of 1 to 3 ml/kg body weight of a suitable solvent by means of gavage into the stomach. Control animals only receive solvent. Controls and substance tests are carried out in parallel on the same day. Control groups and substance-dose groups each consist of 4 to 8 animals. During the experiment, the urine excreted by the animals is collected continuously in a receiver at the base of the cage. The volume of urine per time unit is determined separately for each animal, and the concentration of urinary electrolytes is measured by standard methods of flame photometry. Before the beginning of the experiment, the body weight of the individual animals is determined.

B-8. In Vivo Assay for Detecting Protective Renal Effects: Acute Ischemia/Reperfusion Injury Model in Rodents Laboratory bred male C57Bl/6J mice 6-8 weeks old are obtained from Taconic Biosciences, male 6-8 weeks old Sprague Dawley® rat are obtained from Charles River. Both rats and mice are maintained under standard laboratory conditions, 12 hour light-dark cycles with access to normal chow and drinking water at libitum. For the ischemia reperfusion injury model a total of 10-12 rats or mice is used in each control and experimental group.

Animals are anesthetized with continuous inhaled isoflurane. A right nephrectomy is performed through a right flank incision 7 days before the ischemic procedures in the contralateral kidneys. For renal ischemia a left flank incision is made. Renal vessels are exposed by dissection of the left renal pedicle. Non-traumatic vascular clamps are used to stop blood flow (artery and vein) during 45 min (rats) or 25 min (mice) of ischemia. Reperfusion is established by removing the clamps. The abdominal wall (muscular layer and skin) is closed with 5.0 polypropylene sutures. Temgesic® (Buprenorphin, 0.025 mg/kg s.c.) is applied as an analgesic.

Urine of each animal is collected in metabolic cages over night before sacrifice at 24 h post ischemia. Upon sacrifice, blood samples are obtained under terminal anesthesia. After centrifugation of the blood samples, serum is isolated. Both serum creatinine and serum urea are measured via clinical biochemistry analyzer (Pentra 400). For the assessment of serum and urinary kidney injury biomarkers (Neutrophil gelatinase-associated lipocalin [NGAL], kidney injury molecule-1 [KIM-1] and Osteopontin) ELISA's are performed according to the manufacturers protocol. Both urinary creatinine and albumin are measured to determine the albumin/creatinine ratio.

Total RNA is isolated from kidneys. Left kidneys are snap-frozen in liquid nitrogen at sacrifice. Kidney tissue is then homogenized and RNA is obtained. Total RNA is transcribed to cDNA. Using TaqMan real-time PCR renal NGAL, Osteopontin, KIM-1, Nephrin and Podocin mRNA expression is analyzed in whole kidney tissue.

Differences between groups are analyzed by one-way ANOVA with Dunnett's corrections for multiple comparisons. Statistical significance is defined as $p<0.05$. All statistical analyses are done using GraphPad Prism 6.

B-9. In Vivo Assay for Detecting Cardiovascular Effects: Hemodynamic Investigations in Anaesthetized Dogs Male beagle dogs (Beagle, Marshall BioResources, USA) with a weight of between 10 and 15 kg are anesthetized with pentobarbital (30 mg/kg iv, Narcoren®, Merial, Germany) for the surgical interventions and the hemodynamic and functional investigation termini. Pancuroniumbromide (Pancuronium Inresa, Inresa, Germany, 2-4 mg/animal i.v.) serves additionally as a muscle relaxant. The dogs are intubated and ventilated with an oxygen/ambient air mixture (30/70%), about 2.5-4 L/min. Ventilation takes place using a ventilator from GE Healthcare (Avance, Germany) and is monitored using a carbon dioxide analyzer (-Datex Ohmeda). The anesthesia is maintained by continual infusion of pentobarbital (50 µg/kg/min); fentanyl is used as an analgesic (10 µg/kg/h).

In preparatory interventions, the dogs are fitted with a cardiac pacemaker. At start of experiment, a cardiac pacemaker from Biotronik (Logos®, Germany) is implanted into a subcutaneous skin pocket and is contacted with the heart via a pacemaker electrode (Siello S60®, Biotronik, Germany) which is advanced through the external jugular vein, with illumination, into the right ventricle.

Thereafter accesses are removed and the dog wakes spontaneously from the anesthesia. After a further 7 days, the above-described pacemaker is activated and the heart is stimulated at a frequency of 220 beats per minute.

The actual drug testing experiments take place 28 days after the beginning of pacemaker stimulation, using the following instrumentation:

Introduction of a bladder catheter for bladder relief and for measuring the flow of urine Attachment of electrocardiography (ECG) leads to the extremities for ECG measurement Introduction of a sheath introducer filled with sodium chloride solution into the femoral artery. This tube is connected to a pressure sensor (Braun Melsungen, Melsungen, Germany) for measuring the systemic blood pressure Introduction of a Millar Tip catheter (type 350 PC, Millar Instruments, Houston, USA) through a port secured in the carotid artery, for measuring cardiac hemodynamics.

Introduction of a Swan-Ganz catheter (CCOmbo 7.5F, Edwards, Irvine, USA) via the jugular vein into the pulmonary artery, for measuring the cardiac output, oxygen saturation, pulmonary arterial pressures and central venous pressure Siting of a venous catheter in the cephalic vein, for infusing pentobarbital, for liquid replacement and for blood sampling (determination of the plasma levels of substance or other clinical blood values)

Siting of a venous catheter in the saphenous vein, for infusing fentanyl and for administration of substance Infusion of vasopressin (Sigma) in increasing dosage, up to a dose of 4 mU/kg/min. The pharmacological substances are then tested with this dosage.

The primary signals are amplified if necessary (ACQ7700, Data Sciences International, USA or Edwards-Vigilance-Monitor, Edwards, Irvine, USA) and subsequently fed into the Ponemah system (Data Sciences International, USA) for evaluation. The signals are recorded continuously throughout the experimental period, and are further processed digitally by said software, and averaged over 30 seconds.

The invention claimed is:

1. A compound of formula (I)

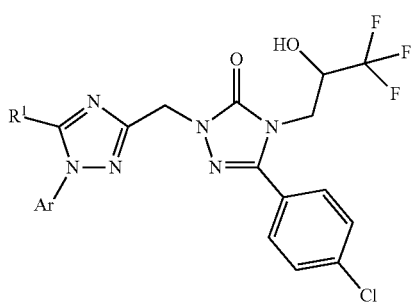

in which
R$^1$ represents a group of the formula

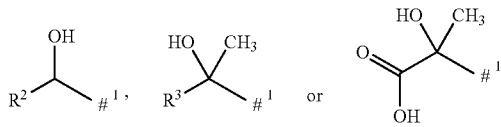

in which
$^1$ represents the point of attachment to the rest of the molecule,
R$^2$ represents a group selected from trifluoromethyl and (C$_2$-C$_4$)-alkyl,
wherein any (C$_2$-C$_4$)-alkyl group is optionally substituted with up to three fluorine atoms,
R$^3$ represents (C$_1$-C$_4$)-alkyl,
wherein any (C$_1$-C$_4$)-alkyl group is optionally substituted with up to three fluorine atoms,
Ar represents a phenyl group or a 5- or 6-membered heteroaryl group attached via a ring carbon atom having one, two or three ring heteroatoms selected from N, O and S,
wherein any phenyl group and any 5- or 6-membered heteroaryl group are each optionally substituted, identically or differently, with one or two groups selected from halogen, nitro, cyano, (C$_1$-C$_4$)-alkyl, (C$_1$-C$_4$)-alkoxy, (C$_1$-C$_4$)-alkylsulfanyl, (C$_1$-C$_4$)-alkoxycarbonyl, aminocarbonyl and —S(=O)$_2$NH$_2$,
wherein said (C$_1$-C$_4$)-alkyl group, said (C$_1$-C$_4$)-alkoxy group and said (C$_1$-C$_4$)-alkylsulfanyl group are each optionally substituted with up to three fluorine atoms
and/or a pharmaceutically acceptable salt, hydrate and/or solvate thereof.

2. A compound of formula (I) according to claim 1, wherein
R$^1$ represents a group of the formula

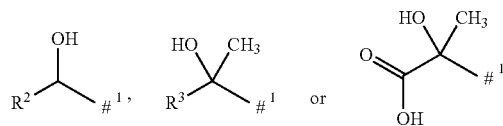

in which
$^1$ represents the point of attachment to the rest of the molecule,
R$^2$ represents a group selected from trifluoromethyl and (C$_2$-C$_4$)-alkyl,
wherein any (C$_2$-C$_4$)-alkyl group is optionally substituted with up to three fluorine atoms,
R$^3$ represents (C$_1$-C$_4$)-alkyl,
wherein any (C$_1$-C$_4$)-alkyl group is optionally substituted with up to three fluorine atoms,
Ar represents a group selected from phenyl or pyridyl,
wherein any phenyl group and any pyridyl group is each optionally substituted, identically or differently, with one or two groups selected from halogen, cyano, (C$_1$-C$_4$)-alkyl, (C$_1$-C$_4$)-alkoxy and aminocarbonyl,
wherein said (C$_1$-C$_4$)-alkyl group or said (C$_1$-C$_4$)-alkoxy group are each optionally substituted with up to three fluorine atoms,
and/or a pharmaceutically acceptable salt, hydrate and/or solvate thereof.

3. A compound of formula (I) according to claim 1, wherein
R$^1$ represents a group of the formula

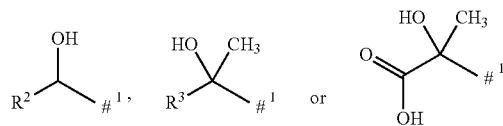

in which
$^1$ represents the point of attachment to the rest of the molecule,

R² represents an ethyl group,
R³ represents a methyl group,
Ar represents a group of the formula

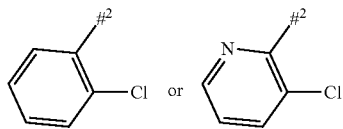

in which
² represents the point of attachment to the nitrogen atom,
and/or a pharmaceutically acceptable salt, hydrate and/or solvate thereof.

4. A compound of formula (I) according to claim 1, wherein
R¹ represents a group of the formula

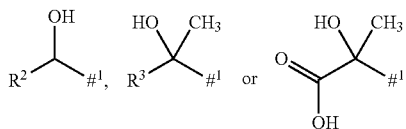

in which
¹ represents the point of attachment to the rest of the molecule,
R² represents a group selected from trifluoromethyl and ethyl,
R³ represents a methyl group,
Ar represents a group of the formula

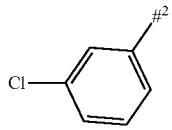

in which
² represents the point of attachment to the nitrogen atom,
and/or a pharmaceutically acceptable salt, hydrate and/or solvate thereof.

5. A method of preparing a compound of formula (I) according to claim 1 said method comprising
[A] allowing an intermediate compound of formula (II):

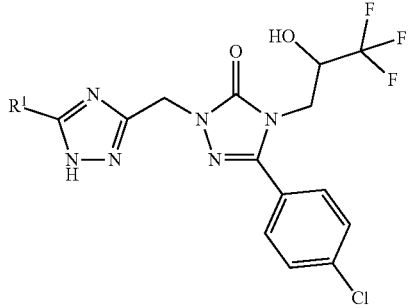

in which
R¹ represents a group of the formula

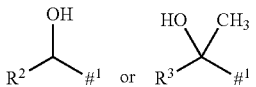

in which
¹, R² and R³ are as defined for the compound of formula (I),
to react with a compound of formula (III):

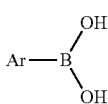

in which
Ar is as defined for the compound of formula (I),
in the presence of a copper catalyst and an amine base thereby giving a compound of formula (I-A):

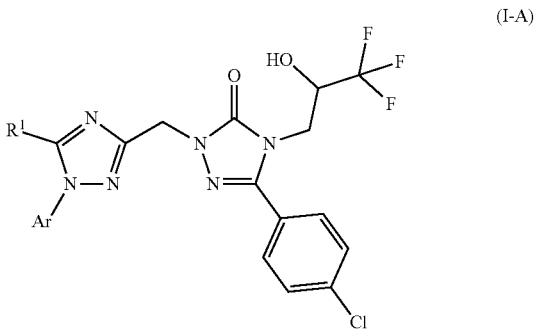

in which
R¹ represents a group of the formula

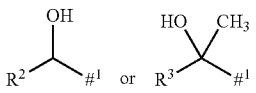

in which
¹, R² and R³ are as defined for the compound of formula (I),
Ar is as defined for the compound of formula (I), or

[B] allowing an intermediate compound of formula (IV):

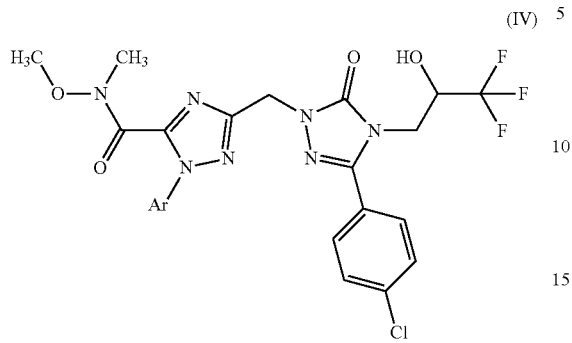

(IV)

in which
Ar is as defined for the compound of formula (I),
to react with a compound of formula (V):

$R^2-MgX$ (V)

in which
$R^2$ is as defined for the compound of formula (I),
X represents chloride, bromide or iodide, to give an intermediate compound of formula (VI):

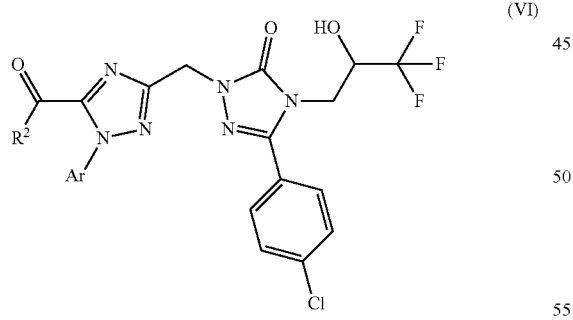

(VI)

in which
$R^2$ and Ar are as defined for the compound of formula (I),
which is then allowed to react with a suitable reduction reagent, optionally sodium borohydride, thereby giving a compound of formula (I-B):

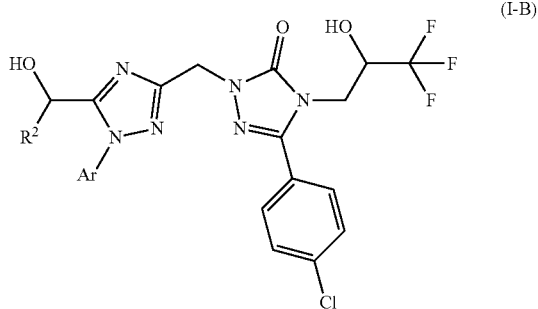

(I-B)

in which
$R^2$ and Ar are as defined for the compound of formula (I), or

[C] allowing an intermediate compound of formula (VII):

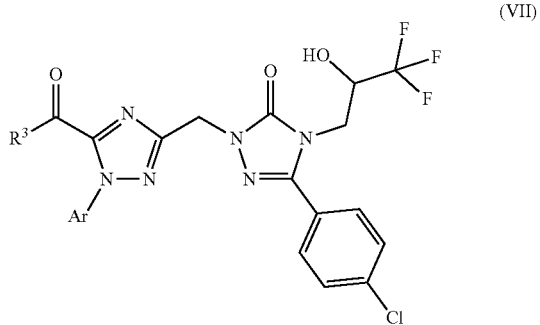

(VII)

in which
$R^3$ and Ar are as defined for the compound of formula (I),
to react with a compound of formula (VIII):

$H_3C-MgX$, (VIII)

in which
X represents chloride, bromide or iodide,
thereby giving a compound of formula (I-C):

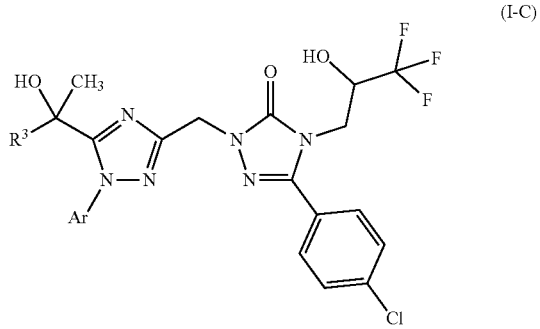

(I-C)

in which
$R^3$ and Ar are as defined for the compound of formula (I)

each [A], [B] and [C] optionally followed, where appropriate, by (i) separating the compounds of formula (I) thus obtained into their respective enantiomers or diastereomers, and/or (ii) converting the compounds of formula (I) into their respective hydrates, solvates, salts and/or hydrates or solvates of the salts by treatment with the corresponding solvents and/or acids or bases.

6. Compound as defined in claim 1 for use in a method for treatment of acute and chronic kidney diseases and acute and chronic heart failure.

7. A compound as defined in claim 1 for manufacture of a pharmaceutical composition for the treatment of acute and chronic kidney diseases and acute and chronic heart failure.

8. The pharmaceutical composition comprising a compound as defined in claim 1 and one or more pharmaceutically acceptable excipients.

9. The pharmaceutical composition of claim 8 further comprising one or more additional therapeutic agents selected from the group consisting of diuretics, angiotensin AII antagonists, ACE inhibitors, beta-receptor blockers, mineralocorticoid receptor antagonists, organic nitrates, NO donors, activators and stimulators of the soluble guanylate cyclase, and positive-inotropic agents.

10. The pharmaceutical composition as defined in claim 8 for treatment of acute and chronic kidney diseases and acute and chronic heart failure.

11. Method for treatment of acute and chronic kidney diseases and acute and chronic heart failure comprising administering to a human or other mammal in need thereof a therapeutically effective amount of one or more compounds as defined in claim 1, or of a pharmaceutical composition thereof.

* * * * *